US009593155B2

(12) United States Patent
Carrington et al.

(10) Patent No.: US 9,593,155 B2
(45) Date of Patent: Mar. 14, 2017

(54) OXYNTOMODULIN ANALOGS

(71) Applicants: MERCK SHARP & DOHME CORP., Rahway, NJ (US); ISTITUTO DI RICERCHE DI BIOLOGIA P. ANGELETTI S.R.L., Rome (IT); INDIANA UNIVERSITY RESEARCH AND TECHNOLOGY CORPORATION, Indianapolis, IN (US)

(72) Inventors: Paul E. Carrington, Rahway, NJ (US); George J. Eiermann, Rahway, NJ (US); Donald J. Marsh, Rahway, NJ (US); Joseph M. Metzger, Rahway, NJ (US); Alessandro Pocai, Rahway, NJ (US); Ranabir Sinha Roy, Rahway, NJ (US); Elisabetta Bianchi, Pommezia (IT); Paolo Ingallinella, Pommezia (IT); Antonello Pessi, Pommezia (IT); Alessia Santoprete, Pommezia (IT); Elena Capito, Pommezia (IT); Richard Dimarchi, Indianapolis, IN (US); Brian Ward, Bloomington, IN (US)

(73) Assignees: MERCK SHARP & DOHME CORP., Rahway, NJ (US); MSD ITALIA S.R.L., Rome (IT); INDIANA UNIVERSITY RESEARCH AND TECHNOLOGY CORPORATION, Indianapolis, IN (US)

(*) Notice: Subject to any disclaimer, the term of this patent is extended or adjusted under 35 U.S.C. 154(b) by 0 days.

(21) Appl. No.: 14/686,760

(22) Filed: Apr. 14, 2015

(65) Prior Publication Data
US 2015/0307580 A1 Oct. 29, 2015

Related U.S. Application Data

(63) Continuation of application No. 13/202,524, filed on Mar. 2, 2012, now abandoned, which is a continuation-in-part of application No. PCT/US2009/034448, filed on Feb. 19, 2009.

(51) Int. Cl.
*C07K 14/605* (2006.01)
*A61K 38/00* (2006.01)
*C07K 14/575* (2006.01)

(52) U.S. Cl.
CPC .......... *C07K 14/605* (2013.01); *C07K 14/575* (2013.01); *A61K 38/00* (2013.01)

(58) Field of Classification Search
CPC ............... C07K 14/605; A61K 38/00
See application file for complete search history.

(56) References Cited

U.S. PATENT DOCUMENTS

| 4,275,152 | A  | 6/1981  | Esders et al.    |
|-----------|----|---------|------------------|
| 7,125,979 | B2 | 10/2006 | Low et al.       |
| 7,238,663 | B2 | 7/2007  | DeFelippis et al.|
| 2004/0235710 | A1 | 11/2004 | DeFelippis et al. |
| 2005/0095679 | A1 | 5/2005  | Prescott et al.  |
| 2006/0252916 | A1 | 11/2006 | DiMarchi et al.  |
| 2008/0101017 | A1 | 5/2008  | Hata et al.      |
| 2008/0125574 | A1 | 5/2008  | Sheffer et al.   |
| 2008/0318837 | A1 | 12/2008 | Quay et al.      |

FOREIGN PATENT DOCUMENTS

| CA | 2638800 A1 | 9/2007 |
| JP | 2005-508895 A | 4/2005 |
| JP | 2005-519059 A | 6/2005 |
| WO | 2007/100535 A2 | 9/2007 |
| WO | 2008/101017 A2 | 8/2008 |
| WO | 2009/155258 A2 | 12/2009 |
| WO | 2010/071807 A1 | 6/2010 |
| WO | 2010/096142 A1 | 8/2010 |

OTHER PUBLICATIONS

Notification of the Fourth Office Action Chinese Patent Application No. 200980158734.X dated Jun. 11, 2015 with English translation.
Extended European Search Report for Application No. 09840594.7-1212/2398483 dated Feb. 4, 2013.
Notice of Intent to Grant issued in European Application No. 09840594.7 mailed Nov. 12, 2013, 8 pages.
Chinese Office Action issued in Chinese Application No. 200980158734.X issued on Feb. 24, 2014, with English Translation.
Russian Office Action issued in Russian Application No. 2011134596 dated Apr. 29, 2014, w/Partial English translation.
Communication Under Rule 71(3) EPC EP Application No. 09 840 594.7 dated Jun. 3, 2014.
Official Communication Mexican Patent Application No. MX/a/2011/008717 dated Apr. 30, 2014.
Notification of Reasons for Refusal JP Patent Application No. 2011-551052 dated May 27, 2014 w/English translation.
Office Action issued in Chinese Application No. 200980158734.X dated Sep. 16, 2014, w/English translation.
Philippine Office Action issued in Philippines Application No. 1/2011/501665 dated Nov. 28, 2014.
Carrington et al, "Human Ozyntomodulin analog peptide,MM127, SEQ ID 120," XP-002732869, website: http://ibis.internal.epo.org/exam/dbfetch.jsp?id=GSP:AYH46107.
Partial Supplementary European Search report issued in European Application No. 12803439.1-1406 dated Dec. 15, 2014.

(Continued)

*Primary Examiner* — Prema Mertz
(74) *Attorney, Agent, or Firm* — McDermott Will & Emery LLP

(57) ABSTRACT

Peptide analogs of oxyntomodulin (OXM, glucagon-37), which have been modified to be resistant to cleavage and inactivation by dipeptidyl peptidase IV (DPP-IV) and to increase in vivo half-life of the peptide analog while enabling the peptide analog to act as a dual GLP-1/glucagon receptor (GCGR) agonist are described. The peptide analogs are useful for treatment of metabolic disorders such as diabetes and obesity.

10 Claims, 27 Drawing Sheets

(56) References Cited

OTHER PUBLICATIONS

Glucagon Superfamily peptide SEQ:1718. Retrieved from EBI accession No. GSP: AYI45428, Database accession No. AYI45428, sequence & Database Geneseq.
Glucagon Superfamily peptide SEQ:1728. Retrieved from EBI accession No. GSP: AYI45438, Database accession No. AYI45438, sequence & Database Geneseq.
Glucagon Superfamily peptide SEQ:1720. Retrieved from EBI accession No. GSP: AYI45430, Database accession No. AYI45430, sequence & Database Geneseq.
Human Ozyntomodulin analog peptide, MM127, SEQ ID 120, XP-002732869, retrieved from EBI accession No. GSP: AYH46107, Database accession No. AYH46107. website: http://ibis.internal.epo.org/exam/dbfetch.jsp?id=GSP: AYH46107.
Chilean Office Action issued in Chilean Application No. 2036-2011 dated Jul. 9, 2014.
Pan et al. (2007). Synthesis of cetuximab-immunoliposomes via a cholesterol-based membrane anchor for targeting of EGFR. Bioconjub Chem, 18(1), 101-108.
International Search Report and Written Opinion issued in International Patent Application No. PCT/US09/34448, dated Jun. 4, 2010.
International Search Report and Written Opinion issued in International Patent Application No. PCT/US09/68678, dated May 5, 2010.
Notice of Allowance issued in U.S. Appl. No. 13/202,524 dated Jan. 14, 2015.
United States Office Action issued in U.S. Appl. No. 13/202,524 dated Jul. 1, 2014.
United States Office Action issued in U.S. Appl. No. 13/202,524 dated Nov. 27, 2013.
Kundsen, L.B. et al, "Potent derivatives of glucagon-like peptide-1 with pharmacokinetic properties suitable for once daily administration", J Med Chem., 43 pp. 1664-1669, 2000.
Hinke, S.A. et al, "Dipeptidyl peptidase IV (DPIV/CD26) degradation of glucagon. Characterization of glucagon degradation products and DPIV-resistant analogs", J Biol Chem., 275, pp. 3827-3834, 2000.
Canadian Office Action dated Jan. 22, 2016, issued in Canadian Patent Application No. 2,754,350.
Chilean Rejection Resolution dated Sep. 2, 2016, issued in Chilean Patent Application No. 2036-2011.
Office Action Peruvian Patent Application No. 1525-2011 dated Jul. 7, 2015.

SEQUENCE LISTING

```
<160> NUMBER OF SEQ ID NOS: 127

<210> SEQ ID NO 1
<211> LENGTH: 37
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide

<400> SEQUENCE: 2

His Ser Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide

<400> SEQUENCE: 3

His Ser Asp Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```

<210> SEQ ID NO 4
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<223> OTHER INFORMATION: C-term CONH2

<400> SEQUENCE: 4

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: Cys(mPEG)5kDa
<220> FEATURE:
<223> OTHER INFORMATION: C-term CONH2

<400> SEQUENCE: 5

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 6
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: Cys(mPEG)20kDa
<220> FEATURE:
<223> OTHER INFORMATION: C-term CONH2

<400> SEQUENCE: 6

His Ser Gln Gly Thr Phe Thr Ser Asp Tyr Ser Lys Tyr Leu Asp Ser

```
1               5                   10                  15
Arg Arg Ala Gln Asp Phe Val Gln Trp Leu Met Asn Thr Lys Arg Asn
            20                  25                  30

Arg Asn Asn Ile Ala Cys
            35

<210> SEQ ID NO 7
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: Cys(mPEG)240kDa
<220> FEATURE:
<223> OTHER INFORMATION: C-term CONH2

<400> SEQUENCE: 7

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
            35

<210> SEQ ID NO 8
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION:
      Cys(cholest-5-en-3-yl {[(2R)-3-amino-2-(amino)-3-
      oxopropyl]thio }acetate)
<220> FEATURE:
<223> OTHER INFORMATION: C-term CONH2

<400> SEQUENCE: 8

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
            35

<210> SEQ ID NO 9
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
```

```
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: Cys(mPEG)5kDa
<220> FEATURE:
<223> OTHER INFORMATION: C-term CONH2

<400> SEQUENCE: 9

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: Cys(mPEG)20kDa
<220> FEATURE:
<223> OTHER INFORMATION: C-term CONH2

<400> SEQUENCE: 10

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 11
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: Cys(mPEG)240kDa
<220> FEATURE:
<223> OTHER INFORMATION: C-term CONH2

<400> SEQUENCE: 11

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
```

```
<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION:
      Cys(cholest-5-en-3-yl {[(2R)-3-amino-2-(amino)-3-
      oxopropyl]thio }acetate)
<220> FEATURE:
<223> OTHER INFORMATION: C-term CONH2

<400> SEQUENCE: 12

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 13
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (27)..(27)
<223> OTHER INFORMATION: Methionine sulfoxide
<220> FEATURE:
<221> NAME/KEY: MOD_RES
<222> LOCATION: (38)..(38)
<223> OTHER INFORMATION: Cys(mPEG)240kDa
<220> FEATURE:
<223> OTHER INFORMATION: C-term CONH2

<400> SEQUENCE: 13

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 14
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
```

<223> OTHER INFORMATION: Alpha-aminoisobutyric acid
<220> FEATURE:
<221> NAME/KEY: MOD_RES
<222> LOCATION: (27)..(27)
<223> OTHER INFORMATION: Methionine sulfoxide
<220> FEATURE:
<221> NAME/KEY: MOD_RES
<222> LOCATION: (38)..(38)
<223> OTHER INFORMATION: Cys(mPEG)260kDa
<220> FEATURE:
<223> OTHER INFORMATION: C-term CONH2

<400> SEQUENCE: 14

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (20)..(20)
<223> OTHER INFORMATION: Cys(mPEG)240kDa
<220> FEATURE:
<223> OTHER INFORMATION: C-term CONH2

<400> SEQUENCE: 15

His Xaa Gln Gly Thr Phe Thr Ser Asp Tyr Ser Lys Tyr Leu Asp Ser
1               5                   10                  15

Arg Arg Ala Cys Asp Phe Val Gln Trp Leu Met Asn Thr Lys Arg Asn
            20                  25                  30

Arg Asn Asn Ile Ala
        35

<210> SEQ ID NO 16
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (21)..(21)
<223> OTHER INFORMATION: Cys(mPEG)240kDa
<220> FEATURE:
<223> OTHER INFORMATION: C-term CONH2

<400> SEQUENCE: 16

His Xaa Gln Gly Thr Phe Thr Ser Asp Tyr Ser Lys Tyr Leu Asp Ser
1               5                   10                  15

Arg Arg Ala Gln Cys Phe Val Gln Trp Leu Met Asn Thr Lys Arg Asn
            20                  25                  30

-continued

```
Arg Asn Asn Ile Ala
        35

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (24)..(24)
<223> OTHER INFORMATION: Cys(mPEG)240kDa
<220> FEATURE:
<221> NAME/KEY: MOD_RES
<222> LOCATION: (27)..(27)
<223> OTHER INFORMATION: Methionine sulfoxide
<220> FEATURE:
<223> OTHER INFORMATION: C-term CONH2

<400> SEQUENCE: 17

His Xaa Gln Gly Thr Phe Thr Ser Asp Tyr Ser Lys Tyr Leu Asp Ser
1               5                   10                  15

Arg Arg Ala Gln Asp Phe Val Cys Trp Leu Met Asn Thr Lys Arg Asn
            20                  25                  30

Arg Asn Asn Ile Ala
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (28)..(28)
<223> OTHER INFORMATION: Cys(mPEG)240kDa
<220> FEATURE:
<223> OTHER INFORMATION: C-term CONH2

<400> SEQUENCE: 18

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Cys Thr Lys Arg Asn
            20                  25                  30

Arg Asn Asn Ile Ala
        35

<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
```

```
<223> OTHER INFORMATION: D-Ser
<220> FEATURE:
<221> NAME/KEY: MOD_RES
<222> LOCATION: (38)..(38)
<223> OTHER INFORMATION: Lys(palmitoyl)
<220> FEATURE:
<223> OTHER INFORMATION: C-term CONH2

<400> SEQUENCE: 19

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Lys
        35

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (1)..(1)
<223> OTHER INFORMATION: Desamino-His
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (27)..(27)
<223> OTHER INFORMATION: Methionine sulfoxide
<220> FEATURE:
<221> NAME/KEY: MOD_RES
<222> LOCATION: (38)..(38)
<223> OTHER INFORMATION: Cys(mPEG)240kDa
<220> FEATURE:
<223> OTHER INFORMATION: C-term CONH2

<400> SEQUENCE: 20

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 21
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2
```

-continued

<400> SEQUENCE: 21

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 22
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (11)..(11)
<223> OTHER INFORMATION: Cys(mPEG)240kDa
<220> FEATURE:
<221> NAME/KEY: MOD_RES
<222> LOCATION: (27)..(27)
<223> OTHER INFORMATION: Methionine sulfoxide
<220> FEATURE:
<223> OTHER INFORMATION: C-term CONH2

<400> SEQUENCE: 22

His Xaa Gln Gly Thr Phe Thr Ser Asp Tyr Cys Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 23
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (12)..(12)
<223> OTHER INFORMATION: Cys(mPEG)240kDa
<220> FEATURE:
<221> NAME/KEY: MOD_RES
<222> LOCATION: (27)..(27)
<223> OTHER INFORMATION: Methionine sulfoxide
<220> FEATURE:
<223> OTHER INFORMATION: C-term CONH2

<400> SEQUENCE: 23

His Xaa Gln Gly Thr Phe Thr Ser Asp Tyr Ser Cys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: Lys(palmitoyl)
<220> FEATURE:
<223> OTHER INFORMATION: C-term CONH2

<400> SEQUENCE: 24

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Lys
        35

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (27)..(27)
<223> OTHER INFORMATION: L-norleucine
<220> FEATURE:
<223> OTHER INFORMATION: C-term CONH2

<400> SEQUENCE: 25

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Leu Asn Thr Lys Arg Asn
            20                  25                  30

Arg Asn Asn Ile Ala Cys
        35

<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (27)..(27)
<223> OTHER INFORMATION: O-methyl-homoserine
<220> FEATURE:
<223> OTHER INFORMATION: C-term CONH2

<400> SEQUENCE: 26

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Ser Asn Thr Lys Arg Asn
            20                  25                  30

Arg Asn Asn Ile Ala Cys
        35

<210> SEQ ID NO 27
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (27)..(27)
<223> OTHER INFORMATION: L-norleucine
<220> FEATURE:
<221> NAME/KEY: MOD_RES
<222> LOCATION: (38)..(38)
<223> OTHER INFORMATION:
      Cys(cholest-5-en-3-yl {[(2R)-3-amino-2-(amino)-3-
      oxopropyl]thio }acetate)
<220> FEATURE:
<223> OTHER INFORMATION: C-term CONH2

<400> SEQUENCE: 27

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Leu Asn Thr Lys Arg Asn
            20                  25                  30

Arg Asn Asn Ile Ala Cys
        35

<210> SEQ ID NO 28
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (27)..(27)
<223> OTHER INFORMATION: O-methyl-homoserine
<220> FEATURE:
<221> NAME/KEY: MOD_RES
<222> LOCATION: (38)..(38)
<223> OTHER INFORMATION:
      Cys(cholest-5-en-3-yl {[(2R)-3-amino-2-(amino)-3-
      oxopropyl]thio }acetate)
<220> FEATURE:
<223> OTHER INFORMATION: C-term CONH2

<400> SEQUENCE: 28

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Ser Asn Thr Lys Arg Asn
            20                  25                  30

Arg Asn Asn Ile Ala Cys
        35

<210> SEQ ID NO 29
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (38)..(38)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2

<400> SEQUENCE: 29

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 30
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<223> OTHER INFORMATION: C-term CONH2

<400> SEQUENCE: 30

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
        35

<210> SEQ ID NO 31
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (27)..(27)
<223> OTHER INFORMATION: Methionine sulfoxide

```
<220> FEATURE:
<221> NAME/KEY: MOD_RES
<222> LOCATION: (38)..(38)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2

<400> SEQUENCE: 31

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
            35

<210> SEQ ID NO 32
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (27)..(27)
<223> OTHER INFORMATION: Methionine sulfoxide
<220> FEATURE:
<221> NAME/KEY: MOD_RES
<222> LOCATION: (38)..(38)
<223> OTHER INFORMATION: Cys(CH2CONH2)
<220> FEATURE:
<223> OTHER INFORMATION: C-term CONH2

<400> SEQUENCE: 32

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala Cys
            35

<210> SEQ ID NO 33
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: 1-Amino-1-cyclohexane carboxylic acid
<220> FEATURE:
<223> OTHER INFORMATION: C-term CONH2

<400> SEQUENCE: 33

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
```

```
<210> SEQ ID NO 34
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminobutyric acid
<220> FEATURE:
<223> OTHER INFORMATION: C-term CONH2

<400> SEQUENCE: 34

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 35
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-alpha-aminobutyric acid
<220> FEATURE:
<223> OTHER INFORMATION: C-term CONH2

<400> SEQUENCE: 35

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 36
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Aminovaleric acid
<220> FEATURE:
<223> OTHER INFORMATION: C-term CONH2

<400> SEQUENCE: 36

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35
```

<210> SEQ ID NO 37
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Beta-cyclopropyl-alanine
<220> FEATURE:
<223> OTHER INFORMATION: C-term CONH2

<400> SEQUENCE: 37

His Ala Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 38
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Propargylglycine
<220> FEATURE:
<223> OTHER INFORMATION: C-term CONH2

<400> SEQUENCE: 38

His Gly Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 39
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Allylglycine
<220> FEATURE:
<223> OTHER INFORMATION: C-term CONH2

<400> SEQUENCE: 39

His Gly Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 40
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: 2-Amino-2-cyclohexyl-propanoic acid
<220> FEATURE:
<223> OTHER INFORMATION: C-term CONH2

<400> SEQUENCE: 40

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 41
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-tertbutylglycine
<220> FEATURE:
<223> OTHER INFORMATION: C-term CONH2

<400> SEQUENCE: 41

His Gly Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 42
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Vinylglycine
<220> FEATURE:
<223> OTHER INFORMATION: C-term CONH2

<400> SEQUENCE: 42

His Gly Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

```
<210> SEQ ID NO 43
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: 1-Amino-1-cyclopropane carboxylic acid
<220> FEATURE:
<223> OTHER INFORMATION: C-term CONH2

<400> SEQUENCE: 43

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 44
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: 1-Amino-1-cyclobutane carboxylic acid
<220> FEATURE:
<223> OTHER INFORMATION: C-term CONH2

<400> SEQUENCE: 44

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 45
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: 1-Amino-1-cyclopentane carboxylic acid
<220> FEATURE:
<223> OTHER INFORMATION: C-term CONH2

<400> SEQUENCE: 45

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 46
```

```
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<223> OTHER INFORMATION: C-term CONH2

<400> SEQUENCE: 46

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Arg Asn
            20                  25                  30

Arg Asn Asn Ile Ala Cys
        35

<210> SEQ ID NO 47
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<223> OTHER INFORMATION: C-term CONH2

<400> SEQUENCE: 47

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Cys
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<223> OTHER INFORMATION: C-term CONH2

<400> SEQUENCE: 48

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Cys
            20                  25                  30

<210> SEQ ID NO 49
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
```

```
<221> NAME/KEY: MOD_RES
<222> LOCATION: (2)..(2)
<223> OTHER INFORMATION: D-Ser
<220> FEATURE:
<223> OTHER INFORMATION: C-term CONH2

<400> SEQUENCE: 49

His Ser Gln Gly Thr Phe Thr Ser Asp Tyr Ser Lys Tyr Leu Asp Ser
1               5                   10                  15

Glu Arg Ala Gln Asp Phe Val Gln Trp Leu Met Asn Thr Lys Cys
            20                  25                  30

<210> SEQ ID NO 50
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<223> OTHER INFORMATION: C-term CONH2

<400> SEQUENCE: 50

His Ser Gln Gly Thr Phe Thr Ser Asp Tyr Ser Lys Tyr Leu Asp Ser
1               5                   10                  15

Arg Ala Ala Gln Asp Phe Val Gln Trp Leu Met Asn Thr Lys Cys
            20                  25                  30

<210> SEQ ID NO 51
<211> LENGTH: 38
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2

<400> SEQUENCE: 51

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Arg Asn
            20                  25                  30

Arg Asn Asn Ile Ala Cys
        35

<210> SEQ ID NO 52
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
```

```
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2

<400> SEQUENCE: 52

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Cys
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2

<400> SEQUENCE: 53

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Cys
            20                  25                  30

<210> SEQ ID NO 54
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2

<400> SEQUENCE: 54

His Ser Gln Gly Thr Phe Thr Ser Asp Tyr Ser Lys Tyr Leu Asp Ser
1               5                   10                  15

Glu Arg Ala Gln Asp Phe Val Gln Trp Leu Met Asn Thr Lys Cys
```

```
                    20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2

<400> SEQUENCE: 55

His Ser Gln Gly Thr Phe Thr Ser Asp Tyr Ser Lys Tyr Leu Asp Ser
1               5                   10                  15

Arg Ala Ala Gln Asp Phe Val Gln Trp Leu Met Asn Thr Lys Cys
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Lys(Palmitoyl)
<220> FEATURE:
<223> OTHER INFORMATION: C-term CONH2

<400> SEQUENCE: 56

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Lys
            20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Lys(Palmitoyl)
<220> FEATURE:
<223> OTHER INFORMATION: C-term CONH2

<400> SEQUENCE: 57
```

```
His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Lys
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: 1-amino-4,7,10-trioxa-13-tridecanamine
      succinimic acid
<220> FEATURE:
<221> NAME/KEY: MOD_RES
<222> LOCATION: (32)..(32)
<223> OTHER INFORMATION: Lys(Palmitoyl)
<220> FEATURE:
<223> OTHER INFORMATION: C-term CONH2

<400> SEQUENCE: 58

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Xaa Lys
            20                  25                  30

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: 1-amino-4,7,10-trioxa-13-tridecanamine
      succinimic acid
<220> FEATURE:
<221> NAME/KEY: MOD_RES
<222> LOCATION: (32)..(32)
<223> OTHER INFORMATION: Lys(Palmitoyl)
<220> FEATURE:
<223> OTHER INFORMATION: C-term CONH2

<400> SEQUENCE: 59

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Xaa Lys
            20                  25                  30

<210> SEQ ID NO 60
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
```

```
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION:
      Cys(cholest-5-en-3-yl {[(2R)-3-amino-2-(amino)-3-
      oxopropyl]thio }acetate)
<220> FEATURE:
<223> OTHER INFORMATION: C-term CONH2

<400> SEQUENCE: 60

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Cys
            20                  25                  30

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION:
      Cys(cholest-5-en-3-yl {[(2R)-3-amino-2-(amino)-3-
      oxopropyl]thio }acetate)
<220> FEATURE:
<223> OTHER INFORMATION: C-term CONH2

<400> SEQUENCE: 61

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Glu Cys
            20                  25                  30

<210> SEQ ID NO 62
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (31)..(31)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2
```

<400> SEQUENCE: 62

His Xaa Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Cys
            20                  25                  30

<210> SEQ ID NO 63
<211> LENGTH: 39
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: Gamma-Glu
<220> FEATURE:
<221> NAME/KEY: MOD_RES
<222> LOCATION: (39)..(39)
<223> OTHER INFORMATION:
      Cys(cholest-5-en-3-yl {[(2R)-3-amino-2-(amino)-3-
      oxopropyl]thio }acetate)
<220> FEATURE:
<223> OTHER INFORMATION: C-term CONH2

<400> SEQUENCE: 63

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Arg Asn
            20                  25                  30

Arg Asn Asn Ile Ala Glu Cys
        35

<210> SEQ ID NO 64
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (32)..(32)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2

<400> SEQUENCE: 64

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Arg Cys
            20                  25                  30

<210> SEQ ID NO 65
<211> LENGTH: 38
<212> TYPE: PRT

```
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)

<400> SEQUENCE: 65

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Arg Asn
            20                  25                  30

Arg Asn Asn Ile Ala Cys
            35

<210> SEQ ID NO 66
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (31)..(31)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)
<220> FEATURE:
<223> OTHER INFORMATION: C-term CONH2

<400> SEQUENCE: 66

His Xaa Gln Gly Thr Phe Thr Ser Asp Tyr Ser Lys Tyr Leu Asp Ser
1               5                   10                  15

Glu Arg Ala Gln Asp Phe Val Gln Trp Leu Met Asn Thr Lys Cys
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION:
      Cys(cholest-5-en-3-yl {[(2R)-3-amino-2-(amino)-3-
      oxopropyl]thio }acetate)
```

<400> SEQUENCE: 67

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Cys
            20                  25                  30

<210> SEQ ID NO 68
<211> LENGTH: 39
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (38)..(38)
<223> OTHER INFORMATION: Gamma-Glu
<220> FEATURE:
<221> NAME/KEY: MOD_RES
<222> LOCATION: (39)..(39)
<223> OTHER INFORMATION: Lys(Palmitoyl)
<220> FEATURE:
<223> OTHER INFORMATION: C-term CONH2

<400> SEQUENCE: 68

His Ser Gln Gly Thr Phe Thr Ser Asp Tyr Ser Lys Tyr Leu Asp Ser
1               5                   10                  15

Glu Ala Ala Gln Asp Phe Val Gln Trp Leu Met Asn Thr Lys Arg Asn
            20                  25                  30

Arg Asn Asn Ile Ala Glu Lys
        35

<210> SEQ ID NO 69
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION:
      Cys(cholest-5-en-3-yl {[(2R)-3-amino-2-(amino)-3-
      oxopropyl]thio }acetate)

<400> SEQUENCE: 69

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Cys

<210> SEQ ID NO 70
<211> LENGTH: 32

```
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION:
      Cys(cholest-5-en-3-yl {[(2R)-3-amino-2-(amino)-3-
      oxopropyl]thio }acetate)

<400> SEQUENCE: 70

His Ser Gln Gly Thr Phe Thr Ser Asp Tyr Ser Ser Tyr Leu Asp Ser
1               5                   10                  15

Arg Arg Ala Gln Asp Phe Val Gln Trp Leu Met Asn Thr Lys Glu Cys
            20                  25                  30

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION:
      Cys(cholest-5-en-3-yl {[(2R)-3-amino-2-(amino)-3-
      oxopropyl]thio }acetate)

<400> SEQUENCE: 71

His Ser Gln Gly Thr Phe Thr Ser Asp Tyr Ser Lys Tyr Leu Asp Ser
1               5                   10                  15

Arg Ala Ala Gln Asp Phe Val Gln Trp Leu Met Asn Thr Lys Glu Cys
            20                  25                  30

<210> SEQ ID NO 72
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION: Cys(cholest-5-en-3-yl
```

-continued

1-{[(2R)-3-amino-2-(amino)-3-
oxopropyl]thio }-2-oxo-6,9,12,15-tetraoxa-3-azaoctadecan
-18-oate]) or Cys(Oxa4-cholesterol)

<400> SEQUENCE: 72

His Ser Gln Gly Thr Phe Thr Ser Asp Tyr Ser Ser Tyr Leu Asp Ser
1               5                   10                  15

Arg Arg Ala Gln Asp Phe Val Gln Trp Leu Met Asn Thr Lys Glu Cys
            20                  25                  30

<210> SEQ ID NO 73
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION: Cys(cholest-5-en-3-yl
      1-{[(2R)-3-amino-2-(amino)-3-
      oxopropyl]thio }-2-oxo-6,9,12,15-tetraoxa-3-azaoctadecan
      -18-oate]) or Cys(Oxa4-cholesterol)

<400> SEQUENCE: 73

His Ser Gln Gly Thr Phe Thr Ser Asp Tyr Ser Lys Tyr Leu Asp Ser
1               5                   10                  15

Arg Ala Ala Gln Asp Phe Val Gln Trp Leu Met Asn Thr Lys Glu Cys
            20                  25                  30

<210> SEQ ID NO 74
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION:
      Cys(cholest-5-en-3-yl {[(2R)-3-amino-2-(amino)-3-
      oxopropyl]thio }acetate)

<400> SEQUENCE: 74

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr Lys Glu Cys
            20                  25                  30

<210> SEQ ID NO 75
<211> LENGTH: 32
<212> TYPE: PRT

```
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)

<400> SEQUENCE: 75

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr Lys Glu Cys
            20                  25                  30

<210> SEQ ID NO 76
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION: Cys(cholest-5-en-3-yl
      1- {[(2R)-3-amino-2-(amino)-3-
      oxopropyl]thio }-2-oxo-6,9,12,15-tetraoxa-3-azaoctadecan
      -18-oate]) or Cys(Oxa4-cholesterol)

<400> SEQUENCE: 76

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Cys

<210> SEQ ID NO 77
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(32)
<223> OTHER INFORMATION: Gamma-Glu
<220> FEATURE:
```

<220> FEATURE:
<221> NAME/KEY: MOD_RES
<222> LOCATION: (33)..(33)
<223> OTHER INFORMATION:
    S-{1-[46-(cholest-5-en-3-yloxy)-3,43,46-trioxo-7,10,13,
    16,19,22,25,28,31,34,37,40-dodecaoxa-4,44-diazahexatetracont-
    1-yl]-2,5-dioxopyrrolidin-3-yl }-L-cysteine or Cys (mal-oxa12-
    cholesterol)

<400> SEQUENCE: 77

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Cys

<210> SEQ ID NO 78
<211> LENGTH: 33
<212> TYPE: PRT
<213> ORGANISM: Artificial Sequence
<220> FEATURE:
<223> OTHER INFORMATION: Description of Artificial Sequence: Synthetic
    OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION: Cys(cholest-5-en-3-yl
    1- {[(2R)-3-amino-2-(amino)-3-
    oxopropyl]thio }-2-oxo-6,9,12,15-tetraoxa-3-azaoctadecan
    -18-oate]) or Cys(Oxa4-cholesterol)

<400> SEQUENCE: 78

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Cys

<210> SEQ ID NO 79
<211> LENGTH: 33
<212> TYPE: PRT
<213> ORGANISM: Artificial Sequence
<220> FEATURE:
<223> OTHER INFORMATION: Description of Artificial Sequence: Synthetic
    OXM analog polypeptide
<220> FEATURE:
<221> NAME/KEY: MOD_RES
<222> LOCATION: (2)..(2)
<223> OTHER INFORMATION: 1-Amino-1-cyclobutane carboxylic acid
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION: Cys(cholest-5-en-3-yl
    1- {[(2R)-3-amino-2-(amino)-3-
    oxopropyl]thio }-2-oxo-6,9,12,15-tetraoxa-3-azaoctadecan
    -18-oate]) or Cys(Oxa4-cholesterol)

<400> SEQUENCE: 79

His Xaa Gln Gly Thr Phe Thr Ser Asp Tyr Ser Lys Tyr Leu Asp Ser

```
                            1               5                  10                  15
Arg Arg Ala Gln Asp Phe Val Gln Trp Leu Met Asn Thr Lys Glu Glu
            20                  25                  30

Cys

<210> SEQ ID NO 80
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: misc_feature
<222> LOCATION: (16)..(16)
<223> OTHER INFORMATION: Lactam bridge between side chains at positions
      16 and 20
<220> FEATURE:
<221> NAME/KEY: misc_feature
<222> LOCATION: (20)..(20)
<223> OTHER INFORMATION: Lactam bridge between side chains at positions
      16 and 20
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION:
      S-[42-(cholest-5-en-3-yloxy)-2,42-dioxo-6,9,12,15,18,21,24,
      27,30,33,36,39-dodecaoxa-3-azadotetracont-1-yl]-L-cysteine
      or Cys (oxa12-cholesterol)

<400> SEQUENCE: 80

His Ser Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr Lys Glu Glu
            20                  25                  30

Cys

<210> SEQ ID NO 81
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: misc_feature
<222> LOCATION: (16)..(16)
<223> OTHER INFORMATION: Lactam bridge between side chains at positions
      16 and 20
<220> FEATURE:
<221> NAME/KEY: misc_feature
<222> LOCATION: (20)..(20)
<223> OTHER INFORMATION: Lactam bridge between side chains at positions
      16 and 20
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
```

```
<222> LOCATION: (33)..(33)
<223> OTHER INFORMATION:
      S-[42-(cholest-5-en-3-yloxy)-2,42-dioxo-6,9,12,15,18,
      21,24,27,30,33,36,39-dodecaoxa-3-azadotetracont-1-yl]
      -L-cysteine or Cys (oxa12-cholesterol)

<400> SEQUENCE: 81

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr Lys Glu Glu
            20                  25                  30

Cys

<210> SEQ ID NO 82
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: 1-Amino-1-cyclobutane carboxylic acid
<220> FEATURE:
<221> NAME/KEY: misc_feature
<222> LOCATION: (16)..(16)
<223> OTHER INFORMATION: Lactam bridge between side chains at positions
      16 and 20
<220> FEATURE:
<221> NAME/KEY: misc_feature
<222> LOCATION: (20)..(20)
<223> OTHER INFORMATION: Lactam bridge between side chains at positions
      16 and 20
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION:
      S-[42-(cholest-5-en-3-yloxy)-2,42-dioxo-6,9,12,15,18,
      21,24,27,30,33,36,39-dodecaoxa-3-azadotetracont-1-yl]
      -L-cysteine or Cys (oxa12-cholesterol)

<400> SEQUENCE: 82

His Xaa Gln Gly Thr Phe Thr Ser Asp Tyr Ser Lys Tyr Leu Asp Glu
1               5                   10                  15

Arg Arg Ala Lys Asp Phe Val Gln Trp Leu Met Asn Thr Lys Glu Glu
            20                  25                  30

Cys

<210> SEQ ID NO 83
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
```

```
<223> OTHER INFORMATION:
      S-[42-(cholest-5-en-3-yloxy)-2,42-dioxo-6,9,12,15,18,
      21,24,27,30,33,36,39-dodecaoxa-3-azadotetracont-1-yl]
      -L-cysteine or Cys (oxa12-cholesterol)

<400> SEQUENCE: 83

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Cys

<210> SEQ ID NO 84
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION:
      S-[42-(cholest-5-en-3-yloxy)-2,42-dioxo-6,9,12,15,18,
      21,24,27,30,33,36,39-dodecaoxa-3-azadotetracont-1-yl]
      -L-cysteine or Cys (oxa12-cholesterol)

<400> SEQUENCE: 84

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Cys

<210> SEQ ID NO 85
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: 1-Amino-1-cyclobutane carboxylic acid
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION:
      S-[42-(cholest-5-en-3-yloxy)-2,42-dioxo-6,9,12,15,18,
      21,24,27,30,33,36,39-dodecaoxa-3-azadotetracont-1-yl]
      -L-cysteine or Cys (oxa12-cholesterol)

<400> SEQUENCE: 85

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
```

```
                    20                  25                  30

Cys

<210> SEQ ID NO 86
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION: Lys(Gamma-Glu-palmitoyl)
<220> FEATURE:
<223> OTHER INFORMATION: C-term CONH2

<400> SEQUENCE: 86

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Lys

<210> SEQ ID NO 87
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION:
      S-[42-(cholest-5-en-3-yloxy)-2,42-dioxo-6,9,12,15,18,
      21,24,27,30,33,36,39-dodecaoxa-3-azadotetracont-1-yl]
      -L-cysteine or Cys (oxa12-cholesterol)
<220> FEATURE:
<223> OTHER INFORMATION: C-term CONH2

<400> SEQUENCE: 87

His Ser Gln Gly Thr Phe Thr Ser Asp Tyr Ser Lys Tyr Leu Asp Glu
1               5                   10                  15

Arg Arg Ala Gln Asp Phe Val Gln Trp Leu Met Asn Thr Lys Glu Glu
            20                  25                  30

Cys

<210> SEQ ID NO 88
<211> LENGTH: 32
<212> TYPE: PRT
<213> ORGANISM: Artificial Sequence
<220> FEATURE:
```

<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (20)..(20)
<223> OTHER INFORMATION: Lys(Gamma-Glu-palmitoyl)
<220> FEATURE:
<221> NAME/KEY: MOD_RES
<222> LOCATION: (31)..(32)
<223> OTHER INFORMATION: Gamma-Glu
<220> FEATURE:
<223> OTHER INFORMATION: C-term CONH2

<400> SEQUENCE: 88

His Ser Gln Gly Thr Phe Thr Ser Asp Tyr Ser Lys Tyr Leu Asp Ser
1               5                   10                  15
Arg Arg Ala Lys Asp Phe Val Gln Trp Leu Met Asn Thr Lys Glu Glu
            20                  25                  30

<210> SEQ ID NO 89
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (20)..(20)
<223> OTHER INFORMATION: Lys(Gamma-Glu-Gamma-Glu-palmitoyl)
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 89

His Ser Gln Gly Thr Phe Thr Ser Asp Tyr Ser Lys Tyr Leu Asp Ser
1               5                   10                  15
Arg Arg Ala Lys Asp Phe Val Gln Trp Leu Met Asn Thr Lys Glu
            20                  25                  30

<210> SEQ ID NO 90
<211> LENGTH: 30
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<223> OTHER INFORMATION: C-term CONH2

<400> SEQUENCE: 90

His Ser Gln Gly Thr Phe Thr Ser Asp Lys Ser Lys Tyr Leu Asp Ser
1               5                   10                  15

Arg Arg Ala Gln Asp Phe Val Gln Trp Leu Met Asn Thr Lys
            20                  25                  30

<210> SEQ ID NO 91
<211> LENGTH: 30
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (20)..(20)
<223> OTHER INFORMATION: Lys(Gamma-Glu-Gamma-Glu-palmitoyl)
<220> FEATURE:
<223> OTHER INFORMATION: C-term CONH2

<400> SEQUENCE: 91

His Ser Gln Gly Thr Phe Thr Ser Asp Tyr Ser Lys Tyr Leu Asp Glu
1               5                   10                  15
Arg Arg Ala Lys Asp Phe Val Gln Trp Leu Met Asn Thr Lys
            20                  25                  30

<210> SEQ ID NO 92
<211> LENGTH: 30
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<223> OTHER INFORMATION: C-term CONH2

<400> SEQUENCE: 92

His Ser Gln Gly Thr Phe Thr Ser Asp Lys Ser Lys Tyr Leu Asp Glu
1               5                   10                  15
Arg Arg Ala Gln Asp Phe Val Gln Trp Leu Met Asn Thr Lys
            20                  25                  30

<210> SEQ ID NO 93
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION:
      S-[78-(cholest-5-en-3-yloxy)-2,78-dioxo-6,9,12,15,

```
       18,21,24,27,30,33,36,39,42,45,48,51,54,57,60,63,66,
       69,72,75-tetracosaoxa-3-azaoctaheptacont-1-yl]-L-cysteine
       or Cys (oxa24-cholesterol)

<400> SEQUENCE: 93

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Cys

<210> SEQ ID NO 94
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (24)..(24)
<223> OTHER INFORMATION: Lys(DOTA)
<220> FEATURE:
<221> NAME/KEY: MOD_RES
<222> LOCATION: (27)..(27)
<223> OTHER INFORMATION: Methionine sulfoxide
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION:
       S-[42-(cholest-5-en-3-yloxy)-2,42-dioxo-6,9,12,15,18,
       21,24,27,30,33,36,39-dodecaoxa-3-azadotetracont-1-yl]
       -L-cysteine or Cys (oxa12-cholesterol)
<220> FEATURE:
<223> OTHER INFORMATION: C-term CONH2

<400> SEQUENCE: 94

His Xaa Asp Gly Thr Phe Thr Ser Asp Tyr Ser Lys Tyr Leu Asp Ser
1               5                   10                  15

Arg Arg Ala Gln Asp Phe Val Lys Trp Leu Met Asn Thr Lys Glu Glu
            20                  25                  30

Cys

<210> SEQ ID NO 95
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-palmitoyl)
<220> FEATURE:
<221> NAME/KEY: MOD_RES
<222> LOCATION: (31)..(31)
<223> OTHER INFORMATION: Gamma-Glu
<220> FEATURE:
```

<223> OTHER INFORMATION: C-term CONH2

<400> SEQUENCE: 95

His Ser Gln Gly Thr Phe Thr Ser Asp Lys Ser Lys Tyr Leu Asp Glu
1               5                   10                  15

Arg Arg Ala Gln Asp Phe Val Gln Trp Leu Met Asn Thr Lys Glu
            20                  25                  30

<210> SEQ ID NO 96
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(palmitoyl)
<220> FEATURE:
<221> NAME/KEY: MOD_RES
<222> LOCATION: (31)..(32)
<223> OTHER INFORMATION: Gamma-Glu
<220> FEATURE:
<223> OTHER INFORMATION: C-term CONH2

<400> SEQUENCE: 96

His Ser Gln Gly Thr Phe Thr Ser Asp Lys Ser Lys Tyr Leu Asp Glu
1               5                   10                  15

Arg Arg Ala Gln Asp Phe Val Gln Trp Leu Met Asn Thr Lys Glu Glu
            20                  25                  30

<210> SEQ ID NO 97
<211> LENGTH: 30
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<223> OTHER INFORMATION: C-term CONH2

<400> SEQUENCE: 97

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Met Asn Thr Lys
            20                  25                  30

<210> SEQ ID NO 98
<211> LENGTH: 30
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)

```
<223> OTHER INFORMATION: 1-Amino-1-cyclobutane carboxylic acid
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<223> OTHER INFORMATION: C-term CONH2

<400> SEQUENCE: 98

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Met Asn Thr Lys
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 99

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Lys Glu
            20                  25                  30

<210> SEQ ID NO 100
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION: Lys(Gamma-Glu-palmitoyl)
<220> FEATURE:
<223> OTHER INFORMATION: C-term CONH2

<400> SEQUENCE: 100

His Xaa Gln Gly Thr Phe Thr Ser Asp Tyr Ser Lys Tyr Leu Asp Ser
1               5                   10                  15
```

```
Arg Arg Ala Gln Asp Phe Val Gln Trp Leu Met Asn Thr Lys Glu Glu
            20                  25                  30

Lys

<210> SEQ ID NO 101
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: 1-Amino-1-cyclobutane carboxylic acid
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION: Lys(Gamma-Glu-palmitoyl)
<220> FEATURE:
<223> OTHER INFORMATION: C-term CONH2

<400> SEQUENCE: 101

His Xaa Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Lys

<210> SEQ ID NO 102
<211> LENGTH: 33
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (31)..(32)
<223> OTHER INFORMATION: Gamma-Glu
<220> FEATURE:
<221> NAME/KEY: MOD_RES
<222> LOCATION: (33)..(33)
<223> OTHER INFORMATION:
      S-[38-(cholest-5-en-3-yloxy)-2-oxo-6,9,12,15,18,21,24,27,30,
      33,36-undecaoxa-3-azaoctatriacont-1-yl]-L-cysteine or Cys
      (oxa12-O-cholesterol)

<400> SEQUENCE: 102

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Cys

<210> SEQ ID NO 103
<211> LENGTH: 30
<212> TYPE: PRT
<213> ORGANISM: Artificial Sequence
<220> FEATURE:
<223> OTHER INFORMATION: Description of Artificial Sequence: Synthetic
```

```
        OXM analog polypeptide
<220> FEATURE:
<221> NAME/KEY: MOD_RES
<222> LOCATION: (2)..(2)
<223> OTHER INFORMATION: D-Ser or alpha-aminoisobutyric acid
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (27)..(27)
<223> OTHER INFORMATION: Met, norleucine, or O-methyl-L-homoserine
<220> FEATURE:
<223> OTHER INFORMATION: see specification as filed for detailed
      description of substitutions and preferred embodiments

<400> SEQUENCE: 103

His Xaa Gln Gly Thr Phe Thr Ser Asp Tyr Ser Lys Tyr Leu Asp Ser
1               5                   10                  15

Xaa Xaa Ala Gln Asp Phe Val Gln Trp Leu Xaa Asn Thr Lys
            20                  25                  30

<210> SEQ ID NO 104
<211> LENGTH: 7
<212> TYPE: PRT
<213> ORGANISM: Artificial Sequence
<220> FEATURE:
<223> OTHER INFORMATION: Description of Artificial Sequence: Synthetic
      OXM peptide

<400> SEQUENCE: 104

Arg Asn Arg Asn Asn Ile Ala
1               5

<210> SEQ ID NO 105
<211> LENGTH: 37
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser, alpha-aminoisobutyric acid,
      1-Amino-1-cyclobutane carboxylic acid residue,
      1-Amino-1-cyclohexane carboxylic acid; alpha-aminobutyric acid;
      D-alpha-aminobutyric acid; Aminovaleric acid;
      beta-cyclopropyl-alanine; propargylglycine;
<220> FEATURE:
<221> NAME/KEY: MOD_RES
<222> LOCATION: (2)..(2)
<223> OTHER INFORMATION: cont from above; Allylglycine;
      2-Amino-2-cyclohexyl-propanoic acid; D-tertbutylglycine;
      Vinylglycine; 1-Amino-1-cyclopropane carboxylic acid; or
      1-Amino-1-cyclopentane carboxylic acid
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (27)..(27)
<223> OTHER INFORMATION: Met, norleucine, or O-methyl-L-homoserine
<220> FEATURE:
```

```
<223>  OTHER INFORMATION: see specification as filed for detailed
       description of substitutions and preferred embodiments

<400>  SEQUENCE: 105

His Xaa Gln Gly Thr Phe Thr Ser Asp Tyr Ser Lys Tyr Leu Asp Ser
1               5                   10                  15

Xaa Xaa Ala Gln Asp Phe Val Gln Trp Leu Xaa Asn Thr Lys Arg Asn
            20                  25                  30

Arg Asn Asn Ile Ala
        35

<210>  SEQ ID NO 106
<211>  LENGTH: 30
<212>  TYPE: PRT
<213>  ORGANISM: Artificial Sequence
<220>  FEATURE:
<223>  OTHER INFORMATION: Description of Artificial Sequence: Synthetic
       OXM analog polypeptide
<220>  FEATURE:
<221>  NAME/KEY: MOD_RES
<222>  LOCATION: (2)..(2)
<223>  OTHER INFORMATION: D-Ser, alpha-aminoisobutyric acid,
       1-Amino-1-cyclobutane carboxylic acid residue,
       1-Amino-1-cyclohexane carboxylic acid; alpha-aminobutyric acid;
       D-alpha-aminobutyric acid; Aminovaleric acid;
       beta-cyclopropyl-alanine; propargylglycine;
<220>  FEATURE:
<221>  NAME/KEY: MOD_RES
<222>  LOCATION: (2)..(2)
<223>  OTHER INFORMATION: cont from above; Allylglycine;
       2-Amino-2-cyclohexyl-propanoic acid; D-tertbutylglycine;
       Vinylglycine; 1-Amino-1-cyclopropane carboxylic acid; or
       1-Amino-1-cyclopentane carboxylic acid
<220>  FEATURE:
<221>  NAME/KEY: MOD_RES
<222>  LOCATION: (12)..(12)
<223>  OTHER INFORMATION: Ser or Lys
<220>  FEATURE:
<221>  NAME/KEY: MOD_RES
<222>  LOCATION: (16)..(16)
<223>  OTHER INFORMATION: Ser or Glu
<220>  FEATURE:
<221>  NAME/KEY: MOD_RES
<222>  LOCATION: (17)..(17)
<223>  OTHER INFORMATION: Arg or Glu
<220>  FEATURE:
<221>  NAME/KEY: MOD_RES
<222>  LOCATION: (18)..(18)
<223>  OTHER INFORMATION: Arg or Ala
<220>  FEATURE:
<221>  NAME/KEY: MOD_RES
<222>  LOCATION: (20)..(20)
<223>  OTHER INFORMATION: Gln or Lys
<220>  FEATURE:
<221>  NAME/KEY: MOD_RES
<222>  LOCATION: (27)..(27)
<223>  OTHER INFORMATION: Met, norleucine, methionine sulfoxide, or
       O-methyl-L-homoserine
<220>  FEATURE:
<223>  OTHER INFORMATION: see specification as filed for detailed
       description of substitutions and preferred embodiments

<400>  SEQUENCE: 106

His Xaa Gln Gly Thr Phe Thr Ser Asp Tyr Ser Xaa Tyr Leu Asp Xaa
1               5                   10                  15

Xaa Xaa Ala Xaa Asp Phe Val Gln Trp Leu Xaa Asn Thr Lys
            20                  25                  30

<210>  SEQ ID NO 107
<211>  LENGTH: 39
<212>  TYPE: PRT
<213>  ORGANISM: Artificial Sequence
```

-continued

```
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser, alpha-aminoisobutyric acid,
      1-Amino-1-cyclobutane carboxylic acid residue,
      1-Amino-1-cyclohexane carboxylic acid; alpha-aminobutyric acid;
      D-alpha-aminobutyric acid; Aminovaleric acid;
      beta-cyclopropyl-alanine; propargylglycine;
<220> FEATURE:
<221> NAME/KEY: MOD_RES
<222> LOCATION: (2)..(2)
<223> OTHER INFORMATION: cont from above; Allylglycine;
      2-Amino-2-cyclohexyl-propanoic acid; D-tertbutylglycine;
      Vinylglycine; 1-Amino-1-cyclopropane carboxylic acid; or
      1-Amino-1-cyclopentane carboxylic acid
<220> FEATURE:
<221> NAME/KEY: MOD_RES
<222> LOCATION: (12)..(12)
<223> OTHER INFORMATION: Ser or Lys
<220> FEATURE:
<221> NAME/KEY: MOD_RES
<222> LOCATION: (16)..(16)
<223> OTHER INFORMATION: Ser or Glu
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (27)..(27)
<223> OTHER INFORMATION: Met, norleucine, methionine sulfoxide or
      O-methyl-L-homoserine
<220> FEATURE:
<223> OTHER INFORMATION: see specification as filed for detailed
      description of substitutions and preferred embodiments

<400> SEQUENCE: 107

His Xaa Gln Gly Thr Phe Thr Ser Asp Tyr Ser Xaa Tyr Leu Asp Xaa
1               5                   10                  15

Xaa Xaa Ala Xaa Asp Phe Val Gln Trp Leu Xaa Asn Thr Lys Arg Asn
            20                  25                  30

Thr Lys Arg Asn Asn Ile Ala
35

<210> SEQ ID NO 108
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser, alpha-aminoisobutyric acid,
      1-Amino-1-cyclobutane carboxylic acid residue,
      1-Amino-1-cyclohexane carboxylic acid; alpha-aminobutyric acid;
      D-alpha-aminobutyric acid; Aminovaleric acid;
      beta-cyclopropyl-alanine; propargylglycine;
<220> FEATURE:
<221> NAME/KEY: MOD_RES
<222> LOCATION: (2)..(2)
<223> OTHER INFORMATION: cont from above; Allylglycine;
      2-Amino-2-cyclohexyl-propanoic acid; D-tertbutylglycine;
```

```
      Vinylglycine; 1-Amino-1-cyclopropane carboxylic acid; or
      1-Amino-1-cyclopentane carboxylic acid
<220> FEATURE:
<221> NAME/KEY: MOD_RES
<222> LOCATION: (10)..(10)
<223> OTHER INFORMATION: Tyr or Lys
<220> FEATURE:
<221> NAME/KEY: MOD_RES
<222> LOCATION: (12)..(12)
<223> OTHER INFORMATION: Ser or Lys
<220> FEATURE:
<221> NAME/KEY: MOD_RES
<222> LOCATION: (16)..(16)
<223> OTHER INFORMATION: Ser or Glu
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (27)..(27)
<223> OTHER INFORMATION: Met, norleucine, methionine sulfoxide or
      O-methyl-L-homoserine
<220> FEATURE:
<221> NAME/KEY: MOD_RES
<222> LOCATION: (31)..(31)
<223> OTHER INFORMATION: Gamma-Glu or absent
<220> FEATURE:
<223> OTHER INFORMATION: see specification as filed for detailed
      description of substitutions and preferred embodiments

<400> SEQUENCE: 108

His Xaa Gln Gly Thr Phe Thr Ser Asp Xaa Ser Xaa Tyr Leu Asp Xaa
1               5                   10                  15

Xaa Xaa Ala Xaa Asp Phe Val Gln Trp Leu Xaa Asn Thr Lys Glu
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Description of Artificial Sequence: Synthetic
      OXM analog polypeptide

<400> SEQUENCE: 109

His Ser Gln Gly Thr Phe Thr Ser Asp Ser Ser Lys Tyr Leu Asp Ser
1               5                   10                  15

Arg Arg Ala Gln Asp Phe Val Gln Trp Leu Met Asn Thr Lys
            20                  25                  30

<210> SEQ ID NO 110
<211> LENGTH: 32
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser, alpha-aminoisobutyric acid,
      1-Amino-1-cyclobutane carboxylic acid residue,
      1-Amino-1-cyclohexane carboxylic acid; alpha-aminobutyric acid;
      D-alpha-aminobutyric acid; Aminovaleric acid;
```

```
       beta-cyclopropyl-alanine; propargylglycine;
<220> FEATURE:
<221> NAME/KEY: MOD_RES
<222> LOCATION: (2)..(2)
<223> OTHER INFORMATION: cont from above; Allylglycine;
       2-Amino-2-cyclohexyl-propanoic acid; D-tertbutylglycine;
       Vinylglycine; 1-Amino-1-cyclopropane carboxylic acid; or
       1-Amino-1-cyclopentane carboxylic acid
<220> FEATURE:
<221> NAME/KEY: MOD_RES
<222> LOCATION: (10)..(10)
<223> OTHER INFORMATION: Tyr or Lys
<220> FEATURE:
<221> NAME/KEY: MOD_RES
<222> LOCATION: (12)..(12)
<223> OTHER INFORMATION: Ser or Lys
<220> FEATURE:
<221> NAME/KEY: MOD_RES
<222> LOCATION: (16)..(16)
<223> OTHER INFORMATION: Ser, alpha-aminoisobutyric acid, or Glu
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (27)..(27)
<223> OTHER INFORMATION: Met, norleucine, methionine sulfoxide, or
       O-methyl-L-homoserine
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION: Gamma-Glu or absent
<220> FEATURE:
<223> OTHER INFORMATION: see specification as filed for detailed
       description of substitutions and preferred embodiments

<400> SEQUENCE: 110

His Xaa Gln Gly Thr Phe Thr Ser Asp Xaa Ser Xaa Tyr Leu Asp Xaa
1               5                   10                  15

Xaa Xaa Ala Xaa Asp Phe Val Gln Trp Leu Xaa Asn Thr Lys Glu Glu
            20                  25                  30

<210> SEQ ID NO 111
<211> LENGTH: 31
<212> TYPE: PRT
<213> ORGANISM: Artificial Sequence
<220> FEATURE:
<223> OTHER INFORMATION: Description of Artificial Sequence: Synthetic
       OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
```

```
<222> LOCATION: (31)..(31)
<223> OTHER INFORMATION: Gamma-Glu
<220> FEATURE:
<223> OTHER INFORMATION: C-term CONH2

<400> SEQUENCE: 111

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Glu Glu
            20                  25                  30

<210> SEQ ID NO 112
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (30)..(30)
<223> OTHER INFORMATION: D-Lys
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 112

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Lys Glu
            20                  25                  30

<210> SEQ ID NO 113
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 113

His Ser Gln Gly Thr Phe Thr Ser Asp Lys Ser Lys Tyr Leu Asp Glu
1               5                   10                  15
```

-continued

```
Arg Arg Ala Gln Asp Phe Val Gln Trp Leu Met Asn Thr Lys Glu
            20                  25                  30

<210> SEQ ID NO 114
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (31)..(31)
<223> OTHER INFORMATION: D-gamma-Glu
<220> FEATURE:
<223> OTHER INFORMATION: C-term CONH2

<400> SEQUENCE: 114

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Glu Glu
            20                  25                  30

<210> SEQ ID NO 115
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Glu-Glu-palmitoyl)
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 115

His Ser Gln Gly Thr Phe Thr Ser Asp Lys Ser Lys Tyr Leu Asp Glu
1               5                   10                  15

Arg Arg Ala Gln Asp Phe Val Gln Trp Leu Met Asn Thr Lys Glu
            20                  25                  30

<210> SEQ ID NO 116
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
```

```
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Arg-Arg-palmitoyl)
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 116

His Ser Gln Gly Thr Phe Thr Ser Asp Lys Ser Lys Tyr Leu Asp Glu
1               5                   10                  15

Arg Arg Ala Gln Asp Phe Val Gln Trp Leu Met Asn Thr Lys Glu
            20                  25                  30

<210> SEQ ID NO 117
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(homocysteic acid-homocysteic
      acid-palmitoyl)
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 117

His Ser Gln Gly Thr Phe Thr Ser Asp Lys Ser Lys Tyr Leu Asp Glu
1               5                   10                  15

Arg Arg Ala Gln Asp Phe Val Gln Trp Leu Met Asn Thr Lys Glu
            20                  25                  30

<210> SEQ ID NO 118
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(D-Glu-D-Glu-palmitoyl)
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 118
```

His Ser Gln Gly Thr Phe Thr Ser Asp Lys Ser Lys Tyr Leu Asp Glu
1               5                   10                  15

Arg Arg Ala Gln Asp Phe Val Gln Trp Leu Met Asn Thr Lys Glu
            20                  25                  30

<210> SEQ ID NO 119
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-myristoyl)
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 119

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Lys Glu
            20                  25                  30

<210> SEQ ID NO 120
<211> LENGTH: 31
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-palmitoyl)
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 120

His Ser Gln Gly Thr Phe Thr Ser Asp Lys Ser Lys Tyr Leu Asp Xaa
1               5                   10                  15

Arg Ala Ala Gln Asp Phe Val Gln Trp Leu Met Asp Thr Lys Glu
            20                  25                  30

<210> SEQ ID NO 121
<211> LENGTH: 31

```
<212> TYPE: PRT
<213> ORGANISM: Artificial Sequence
<220> FEATURE:
<223> OTHER INFORMATION: Description of Artificial Sequence: Synthetic
      OXM analog polypeptide
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (10)..(10)
<223> OTHER INFORMATION: Lys(Gamma-Glu-Gamma-Glu-stearoyl)
<220> FEATURE:
<221> NAME/KEY: MOD_RES
<222> LOCATION: (16)..(16)
<223> OTHER INFORMATION: Alpha-aminoisobutyric acid
<220> FEATURE:
<221> NAME/KEY: MOD_RES
<222> LOCATION: (31)..(31)
<223> OTHER INFORMATION: Gamma-Glu
<220> FEATURE:
<223> OTHER INFORMATION: C-term CONH2

<400> SEQUENCE: 121

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Lys Glu
            20                  25                  30

<210> SEQ ID NO 122
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Alpha-aminoisobutyric acid
<220> FEATURE:
<221> NAME/KEY: MOD_RES
<222> LOCATION: (27)..(27)
<223> OTHER INFORMATION: Methionine sulfoxide
<220> FEATURE:
<221> NAME/KEY: MOD_RES
<222> LOCATION: (30)..(31)
<223> OTHER INFORMATION: Gamma-Glu
<220> FEATURE:
<221> NAME/KEY: MOD_RES
<222> LOCATION: (32)..(32)
<223> OTHER INFORMATION: Cys(Oxa12Chol)

<400> SEQUENCE: 122

His Xaa Glu Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Glu Glu
            20                  25                  30

Cys

<210> SEQ ID NO 123
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser, alpha-aminoisobutyric acid,
```

```
        1-Amino-1-cyclobutane carboxylic acid residue,
        1-Amino-1-cyclohexane carboxylic acid; alpha-aminobutyric acid;
        D-alpha-aminobutyric acid; Aminovaleric acid;
        beta-cyclopropyl-alanine; propargylglycine;
<220> FEATURE:
<221> NAME/KEY: MOD_RES
<222> LOCATION: (2)..(2)
<223> OTHER INFORMATION: cont from above; Allylglycine;
        2-Amino-2-cyclohexyl-propanoic acid; D-tertbutylglycine;
        Vinylglycine; 1-Amino-1-cyclopropane carboxylic acid; or
        1-Amino-1-cyclopentane carboxylic acid
<220> FEATURE:
<221> NAME/KEY: MOD_RES
<222> LOCATION: (12)..(12)
<223> OTHER INFORMATION: Ser or Lys
<220> FEATURE:
<221> NAME/KEY: MOD_RES
<222> LOCATION: (16)..(16)
<223> OTHER INFORMATION: Ser or Glu
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (27)..(27)
<223> OTHER INFORMATION: Met, norleucine, methionine sulfoxide, or
        O-methyl-L-homoserine
<220> FEATURE:
<221> NAME/KEY: misc_feature
<222> LOCATION: (31)..(37)
<223> OTHER INFORMATION: This region may or may not be present; when
        present, it is present in its entirety
<220> FEATURE:
<221> NAME/KEY: MOD_RES
<222> LOCATION: (38)..(38)
<223> OTHER INFORMATION: Lys, Cys or absent
<220> FEATURE:
<223> OTHER INFORMATION: see specification as filed for detailed
        description of substitutions and preferred embodiments

<400> SEQUENCE: 123

His Xaa Gln Gly Thr Phe Thr Ser Asp Tyr Ser Xaa Tyr Leu Asp Xaa
1               5                   10                  15

Xaa Xaa Ala Xaa Asp Phe Val Gln Trp Leu Xaa Asn Thr Lys Arg Asn
            20                  25                  30

Arg Asn Asn Ile Ala Xaa
        35

<210> SEQ ID NO 124
<211> LENGTH: 33
<212> TYPE: PRT
<213> ORGANISM: Artificial Sequence
<220> FEATURE:
<223> OTHER INFORMATION: Description of Artificial Sequence: Synthetic
        polypeptide
<220> FEATURE:
<221> NAME/KEY: MOD_RES
<222> LOCATION: (2)..(2)
<223> OTHER INFORMATION: D-Ser, alpha-aminoisobutyric acid,
        1-Amino-1-cyclobutane carboxylic acid residue,
        1-Amino-1-cyclohexane carboxylic acid; alpha-aminobutyric acid;
        D-alpha-aminobutyric acid; Aminovaleric acid;
        beta-cyclopropyl-alanine; propargylglycine;
<220> FEATURE:
<221> NAME/KEY: MOD_RES
<222> LOCATION: (2)..(2)
```

```
<223> OTHER INFORMATION: cont from above; Allylglycine;
      2-Amino-2-cyclohexyl-propanoic acid; D-tertbutylglycine;
      Vinylglycine; 1-Amino-1-cyclopropane carboxylic acid; or
      1-Amino-1-cyclopentane carboxylic acid
<220> FEATURE:
<221> NAME/KEY: MOD_RES
<222> LOCATION: (10)..(10)
<223> OTHER INFORMATION: Tyr or Lys
<220> FEATURE:
<221> NAME/KEY: MOD_RES
<222> LOCATION: (12)..(12)
<223> OTHER INFORMATION: Ser or Lys
<220> FEATURE:
<221> NAME/KEY: MOD_RES
<222> LOCATION: (16)..(16)
<223> OTHER INFORMATION: Ser, alpha-aminoisobutyric acid, or Glu
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (20)..(20)
<223> OTHER INFORMATION: Glu or Lys
<220> FEATURE:
<221> NAME/KEY: MOD_RES
<222> LOCATION: (27)..(27)
<223> OTHER INFORMATION: Met, norleucine, methionine sulfoxide, or
      O-methyl-L-homoserine
<220> FEATURE:
<221> NAME/KEY: MOD_RES
<222> LOCATION: (31)..(31)
<223> OTHER INFORMATION: Gamma-Glu
<220> FEATURE:
<221> NAME/KEY: MOD_RES
<222> LOCATION: (32)..(32)
<223> OTHER INFORMATION: Gamma-Glu or absent
<220> FEATURE:
<221> NAME/KEY: MOD_RES
<222> LOCATION: (33)..(33)
<223> OTHER INFORMATION: Lys, Cys or absent
<220> FEATURE:
<223> OTHER INFORMATION: see specification as filed for detailed
      description of substitutions and preferred embodiments

<400> SEQUENCE: 124

His Xaa Gln Gly Thr Phe Thr Ser Asp Xaa Ser Xaa Tyr Leu Asp Xaa
1               5                   10                  15

Xaa Xaa Ala Xaa Asp Phe Val Gln Trp Leu Xaa Asn Thr Lys Xaa Xaa
            20                  25                  30

Xaa

<210> SEQ ID NO 125
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser or alpha-aminoisobutyric acid
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
```

```
<220> FEATURE:
<221> NAME/KEY: MOD_RES
<222> LOCATION: (27)..(27)
<223> OTHER INFORMATION: Met, norleucine, or O-methyl-L-homoserine
<220> FEATURE:
<221> NAME/KEY: misc_feature
<222> LOCATION: (31)..(37)
<223> OTHER INFORMATION: This region may or may not be present; when
      present, it is present in its entirety
<220> FEATURE:
<221> NAME/KEY: MOD_RES
<222> LOCATION: (38)..(38)
<223> OTHER INFORMATION: Lys, Cys or absent
<220> FEATURE:
<223> OTHER INFORMATION: see specification as filed for detailed
      description of substitutions and preferred embodiments

<400> SEQUENCE: 125

His Xaa Gln Gly Thr Phe Thr Ser Asp Tyr Ser Lys Tyr Leu Asp Ser
1               5                   10                  15

Xaa Xaa Ala Gln Asp Phe Val Gln Trp Leu Xaa Asn Thr Lys Arg Asn
            20                  25                  30

Arg Asn Asn Ile Ala Xaa
        35

<210> SEQ ID NO 126
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser, alpha-aminoisobutyric acid,
      1-Amino-1-cyclobutane carboxylic acid residue,
      1-Amino-1-cyclohexane carboxylic acid; alpha-aminobutyric acid;
      D-alpha-aminobutyric acid; Aminovaleric acid;
      beta-cyclopropyl-alanine; propargylglycine;
<220> FEATURE:
<221> NAME/KEY: MOD_RES
<222> LOCATION: (2)..(2)
<223> OTHER INFORMATION: cont from above; Allylglycine;
      2-Amino-2-cyclohexyl-propanoic acid; D-tertbutylglycine;
      Vinylglycine; 1-Amino-1-cyclopropane carboxylic acid; or
      1-Amino-1-cyclopentane carboxylic acid
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (27)..(27)
<223> OTHER INFORMATION: Met, norleucine, or O-methyl-L-homoserine
<220> FEATURE:
<221> NAME/KEY: misc_feature
<222> LOCATION: (38)..(44)
<223> OTHER INFORMATION: This region may or may not be present; when
      present, it is present in its entirety
<220> FEATURE:
<221> NAME/KEY: MOD_RES
<222> LOCATION: (45)..(45)
<223> OTHER INFORMATION: Lys, Cys or absent
<220> FEATURE:
<223> OTHER INFORMATION: see specification as filed for detailed
      description of substitutions and preferred embodiments

<400> SEQUENCE: 126

His Xaa Gln Gly Thr Phe Thr Ser Asp Tyr Ser Lys Tyr Leu Asp Ser
```

```
1               5                   10                  15
Xaa Xaa Ala Gln Asp Phe Val Gln Trp Leu Xaa Asn Thr Lys Arg Asn
            20                  25                  30
Arg Asn Asn Ile Ala Arg Asn Arg Asn Asn Ile Ala Xaa
        35                  40                  45
```

```
<210> SEQ ID NO 127
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: D-Ser, alpha-aminoisobutyric acid,
      1-Amino-1-cyclobutane carboxylic acid residue,
      1-Amino-1-cyclohexane carboxylic acid; alpha-aminobutyric acid;
      D-alpha-aminobutyric acid; Aminovaleric acid;
      beta-cyclopropyl-alanine; propargylglycine;
<220> FEATURE:
<221> NAME/KEY: MOD_RES
<222> LOCATION: (2)..(2)
<223> OTHER INFORMATION: cont from above; Allylglycine;
      2-Amino-2-cyclohexyl-propanoic acid; D-tertbutylglycine;
      Vinylglycine; 1-Amino-1-cyclopropane carboxylic acid; or
      1-Amino-1-cyclopentane carboxylic acid
<220> FEATURE:
<221> NAME/KEY: MOD_RES
<222> LOCATION: (10)..(10)
<223> OTHER INFORMATION: Tyr or Lys
<220> FEATURE:
<221> NAME/KEY: MOD_RES
<222> LOCATION: (12)..(12)
<223> OTHER INFORMATION: Ser or Lys
<220> FEATURE:
<221> NAME/KEY: MOD_RES
<222> LOCATION: (16)..(16)
<223> OTHER INFORMATION: Ser or Glu
<220> FEATURE:
<221> NAME/KEY: MOD_RES
<222> LOCATION: (17)..(17)
<223> OTHER INFORMATION: Arg or Glu
<220> FEATURE:
<221> NAME/KEY: MOD_RES
<222> LOCATION: (18)..(18)
<223> OTHER INFORMATION: Arg or Ala
<220> FEATURE:
<221> NAME/KEY: MOD_RES
<222> LOCATION: (20)..(20)
<223> OTHER INFORMATION: Gln or Lys
<220> FEATURE:
<221> NAME/KEY: MOD_RES
<222> LOCATION: (27)..(27)
<223> OTHER INFORMATION: Met, norleucine, methionine sulfoxide or
      O-methyl-L-homoserine
<220> FEATURE:
<221> NAME/KEY: MOD_RES
<222> LOCATION: (31)..(31)
<223> OTHER INFORMATION: Gamma-Glu or absent
<220> FEATURE:
<221> NAME/KEY: misc_feature
<222> LOCATION: (32)..(38)
<223> OTHER INFORMATION: This region may or may not be present; when
      present, it is present in its entirety
<220> FEATURE:
<221> NAME/KEY: MOD_RES
<222> LOCATION: (39)..(39)
<223> OTHER INFORMATION: Lys, Cys or absent
<220> FEATURE:
<223> OTHER INFORMATION: see specification as filed for detailed
      description of substitutions and preferred embodiments

<400> SEQUENCE: 127
```

```
His Xaa Gln Gly Thr Phe Thr Ser Asp Xaa Ser Xaa Tyr Leu Asp Xaa
1               5                   10                  15

Xaa Xaa Ala Xaa Asp Phe Val Gln Trp Leu Xaa Asn Thr Lys Glu Arg
            20              25                  30

Asn Arg Asn Asn Ile Ala Xaa
            35
```

OXYNTOMODULIN ANALOGS

CROSS-REFERENCE TO RELATED APPLICATIONS

This application is a Continuation of application Ser. No. 13/202,524, filed on Mar. 2, 2012, which is a continuation-in-part of International Patent Application No. PCT/US2009/034448 filed 19 Feb. 2009, the content of which is incorporated herein in its entirety.

BACKGROUND OF THE INVENTION (1) Field of the Invention

The present invention relates to peptide analogs of oxyntomodulin (OXM, glucagon-37), which have been modified to be resistant to cleavage and inactivation by dipeptidyl peptidase IV (DPP-IV) and to increase in vivo half-life of the peptide analog while enabling the peptide analog to act as a dual GLP-1/glucagon receptor (GCGR) agonist, and the use of such peptide analogs for treatment of metabolic disorders such as diabetes and obesity.

(2) Description of Related Art

The hormone oxyntomodulin (OXM, glucagon-37) is a posttranslational product of preproglucagon processing in the intestine and central nervous system (CNS) and is secreted from L-cells in the gut in response to food intake. Discovered in 1983, OXM has been implicated in the regulation of food intake and energy expenditure (Jarrouse et al., Endocrinol. 115: 102-105 (1984); Schjoldager et al., Eur. J. Clin. Invest., 18: 499-503 (1988)). Central or peripheral administration of OXM in rats causes a decrease in short term food intake with minimal effects on gastric emptying (Dakin et al. Endocrinology, 142: 4244-4250 (2001), Dakin et al. Endocrinology, 145: 2687-2695 (2004)). Repeated intracerebroventricular administration of OXM in rats results in elevated core temperatures and reduced weight gain compared to pair-fed animals, suggesting effects on both caloric intake and energy expenditure (Dakin et al. Am. J. Physiol. Endocrinol. Metab., 283: E1173-E1177 (2002)).

In related studies, peripheral administration of OXM dose-dependently inhibited both fast-induced and dark phase food intake, but unlike GLP-1, had no effect on gastric emptying. OXM also reduced levels of fasting ghrelin and increased c-fos immunoreactivity, in the arcuate nucleus (ARC). Repeated seven-day IP administration of OXM caused a reduction in the rate of body weight gain and adiposity in rats (See Dakin et al. Endocrinology, 145: 2687-2695 (2004)).

Studies of OXM action in mice have demonstrated that although OXM can activate both the glucagon and GLP-1 receptors, the anorectic actions of OXM require only the GLP-1 receptor, as icy OXM inhibits food intake in glucagon receptor knockout mice. However, the anorectic effects of OXM are completely absent in GLP-1 receptor knockout mice. Furthermore, exendin-4, but not OXM, regulates energy expenditure in mice. Hence, OXM appears to be a weak agonist at the GLP-1 receptor, when used in pharmacological concentrations (See Baggio et al., Gastroenterol. 127: 546-58 (2004)). OXM was also found to ameliorate glucose intolerance in mice fed a high fat diet (Dakin et al., Am. J. Physiol. Endocrinol. Metab. 294: E142-E147 (2008) and increase the intrinsic heart rate in mice independent of the GLP-1 receptor (Sowden et al., Am. J. Physiol. Regul. Integr. Comp. Physiol. 292: R962-R970 (2007). OXM has also been shown to differentially affect GLP-1 receptor beta-arrestin recruitment and signaling through Galpha (Jorgensen et al., J. Pharma. Exp. Therapeut. 322: 148-154 (2007)) and to differentially affect hypothalamic neuronal activation following peripheral injection of OXM (Choudhri et al., Biochem. Biophys. Res. Commun. 350: 298-306 (2006)).

In humans, a single 90 minute intravenous infusion of OXM in normal weight healthy subjects reduced hunger scores and food intake at a buffet meal by about 19%. Cumulative twelve-hour caloric intake was reduced by about 11% with no reports of nausea or changes in food palatability (Cohen et al., J. Clin. Endocrinol. Metab., 88: 4696-4701 (2003); Lykkegaard et al., ADA Scientific Sessions, Abstract #1506-P (2003)). More recently, pre-prandial injections of OXM over a four-week period in obese healthy volunteers (BMI about 33) led to a significant reduction of caloric intake on the first day of treatment (about 25%) that was maintained over the course of the study (35% reduction after four weeks) (Wynne et al., Diabetes 54: 2390-2395 (2005)). Robust weight loss was observed at the end of the study in treated subjects (1.9%, placebo-corrected). Plasma levels of OXM were similar to that observed in the infusion study (peak concentration about 950 pM). The absence of any tachyphylaxis and a low incidence of mild and transient nausea (about 3%) despite the relatively high doses necessitated by the poor in vivo stability of OXM (plasma $t_{1/2}$<12 minutes) renders this hormone one of the few obesity targets with both human validation and an attractive tolerability profile.

OXM has a very short half-life and is rapidly inactivated by the cell surface dipeptidyl peptidase IV (DPP-IV) (Zhu et al., J. Biol. Chem. 278: 22418-22423 (2002). However, DPP-IV inhibitors are weight-neutral in the clinic, suggesting that supraphysiological levels of OXM (900-1000 pM) may be required to achieve weight loss in humans. OXM peptide analogs for inducing weight loss in humans has been the object of Published International Application Nos. WO03/022304, WO2004/062685, and WO2006/134340.

OXM therefore shows potential as a treatment for metabolic disorders such as diabetes and obesity. However, because of the poor in vivo stability of OXM, there exists a need to develop OXM analogs that can be safely and efficaciously administered for the treatment of metabolic diseases, such as diabetes and obesity. It would be further desirable if analogs or derivatives were developed that were modified by conjugation to moieties that would improve stability and pharmacokinetics, more particularly modifications that confer resistance to DPP-IV cleavage. It would further be desirable to provide OXM analogs that are capable of acting as dual GLP-1 receptor/glucagon receptor agonists.

BRIEF SUMMARY OF THE INVENTION

The present invention provides oxyntomodulin (OXM, glucagon-37) peptide analogs, which have been modified to be resistant to cleavage and inactivation by dipeptidyl peptidase IV (DPP-IV) and to increase in vivo half-life of the peptide analog while enabling the peptide analog to act as a dual GLP-1/glucagon receptor (GCGR) agonist, and the use of such peptide analogs for treatment of metabolic disorders such as diabetes and obesity. In particular, the analogs disclosed herein reduce food intake and body weight, increase metabolic rate, mediate glucose-dependent insulin secretion (GDIS) from pancreatic islets and improve glucose tolerance, thereby providing a treatment option for individuals afflicted with a metabolic disorder such as metabolic syndrome, obesity, diabetes, metabolic syndrome X, hyperglycemia, impaired fasting glucose, dyslipidemia, atherosclerosis, and other prediabetic states.

Therefore, the present invention provides a peptide comprising the amino acid sequence of a human oxyntomodulin (OXM) shown in SEQ ID NO:1 wherein the second amino acid from the N-terminus is substituted with an amino acid that renders the peptide resistant to cleavage and inactivation by dipeptidyl peptidase IV the peptide includes a lipid or cholesterol moiety covalently linked to the peptide; the peptide optionally includes one to three amino acid substitutions in addition to the substitution at position 2; and the peptide optionally includes a protecting group that, if present, is joined to the C-terminal carboxy group of the peptide; wherein the peptide is capable of acting as a dual GLP-1 receptor and glucagon receptor agonist and has a serum half-life greater than the serum half-life of the human OXM, and pharmaceutically acceptable salts thereof. In further aspects, the amino acid substituted for the second amino acid from the N-terminus is selected from the group consisting of D-serine and α-aminoisobutyric acid.

Further provided is a peptide comprising the amino acid sequence of a human oxyntomodulin (OXM) shown in SEQ ID NO:1 wherein the second amino acid from the N-terminus is substituted with an amino acid selected from the group consisting of D-serine and α-aminoisobutyric acid; the C-terminus of the peptide includes a cysteine residue in which the thiol group of the cysteine residue is covalently linked to a cholesterol moiety by a hydrophilic linker; the peptide optionally includes one to three amino acid substitutions in addition to the substitution at position 2; and the peptide optionally includes a protecting group that, if present, is joined to the C-terminal carboxy group of the peptide; wherein the peptide acts as a dual GLP-1 receptor and glucagon receptor agonist and has a serum half-life greater than the serum half-life of the human OXM, and pharmaceutically acceptable salts thereof.

Further provided is a peptide comprising the amino acid sequence of a human oxyntomodulin (OXM) shown in SEQ ID NO:1 wherein the second amino acid from the N-terminus is substituted with an amino acid that renders the peptide resistant to cleavage and inactivation by dipeptidyl peptidase IV; the peptide includes a lipid or cholesterol moiety covalently linked to the peptide; the peptide includes one or more amino acid substitutions at amino acid positions selected from the group consisting of positions 17, 18, and 27; and the peptide optionally includes a protecting group that, if present, is joined to the C-terminal carboxy group of the peptide; wherein the peptide acts as a dual GLP-1 receptor and glucagon receptor agonist and has a serum half-life greater than the serum half-life of the human OXM, and pharmaceutically acceptable salts thereof. In further aspects, the one or more amino acid substitutions selected from the group consisting of glutamic acid for the arginine at position 17, alanine for the arginine at position 18, norleucine or O-methyl-L-homoserine for the methionine at position 27.

Further provided is a peptide comprising the amino acid sequence of a human oxyntomodulin (OXM) shown in SEQ ID NO:1 wherein the second amino acid from the N-terminus is substituted with an amino acid that renders the peptide resistant to cleavage and inactivation by dipeptidyl peptidase IV; the peptide includes a lipid or cholesterol moiety covalently linked to the peptide; the peptide optionally includes one to three amino acid substitutions in addition to the substitution at position 2; the peptide lacks the amino acid sequence RNRNNIA (SEQ ID NO:104); and the peptide optionally includes a protecting group that, if present, is joined to the C-terminal carboxy group of the peptide;

wherein the peptide acts as a dual GLP-1 receptor and glucagon receptor agonist and has a serum half-life greater than the serum half-life of the human OXM, and pharmaceutically acceptable salts thereof.

In further aspects, the amino acid substitution at position 2 is an amino acid selected from the group consisting of D-serine and α-aminoisobutyric acid and the cholesterol moiety is covalently linked to the thiol group of a cysteine by a hydrophilic linker and the cysteine residue is covalently linked to the C-terminus of the peptide by a peptide bond. In further aspects, the peptide further includes one or more amino acid substitutions at amino acid positions selected from the group consisting of positions 17, 18, and 27. In further aspects, the peptide further includes one or more amino acid substitutions selected from the group consisting of arginine at position 17 to glutamic acid, arginine at position 18 to alanine, methionine at position 27 to norleucine or O-methyl-L-homoserine.

In further aspects of any one of the above peptides, the peptide includes a cholesterol moiety covalently linked to the thiol group of a cysteine residue at the C-terminus of the peptide. In particular aspects, the cholesterol moiety is covalently linked to the thiol group by a hydrophilic linker. The hydrophilic linker can be a peptide or polymer such as an ethoxy polymer that includes one to ten ethoxy units. In further aspects, the hydrophilic linker is an ethoxy polymer that includes four ethoxy units. In other aspects of the peptide, the peptide includes a lipid moiety covalently linked to the ε-amino group of a lysine residue covalently linked to the C-terminus of the peptide, which in particular embodiments is a palmitoyl. In further embodiments, the lysine residue is linked to the C-terminus of the peptide by means of a linker moiety. In particular aspects, the linker moiety includes one or more gamma-glutamic acid residues and in other aspects, the linker moiety is 1-amino-4,7,10-tioxa-13-tridecanamine succinimic acid.

Further provided is an OXM peptide analog selected from the peptide analogs presented in Table 1 and Table 2 and the use of one more of the OXM peptide analogs presented in Table 1 and Table 2 in the manufacture of a medicament for the treatment of a metabolic disorder.

Further provided is a peptide analog comprising the structure

wherein P is a peptide having the amino acid sequence (SEQ ID NO: 106)
HX₁QGTFTSDYSX₂YLDX₃X₄X₅AX₆DFVQWLX₇NTK wherein $X_1$ is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe); $X_2$ is Ser (S) or Lys (K); $X_3$ is Ser (S) or Glu (E); $X_4$ is an arginine (R) or glutamic acid (E) residue; $X_5$ is an arginine (R) or alanine (A) residue; $X_6$ is Gln (Q) or Lys (K); $X_7$ is a methionine (M), norleucine (Nle), methionine sulfoxide (m), or O-methyl-L-homoserine (o) residue;

$Z_1$ is an optionally present protecting group that, if present, is joined to the N-terminal amino group, $L_1$ is optional but when present is amino acid sequence RNRNNIA (SEQ ID NO:104) or a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In further aspects of the above peptides, $Z_2$ is a cysteine residue, which in particular embodiments, can be covalently linked by its thiol group to a cholesterol moiety or a lipid moiety. In other embodiments, the cholesterol moiety or lipid moiety is covalently linked to the thiol group of the cysteine by a hydrophilic linker. In particular aspects, the hydrophilic linker is an ethoxy polymer that includes one to twenty-four ethoxy units or in more specific aspects, the hydrophilic linker is an ethoxy polymer that includes four ethoxy units.

In further aspects of the above peptides, $Z_2$ is a lysine residue, which in particular embodiments, the ε-amino group of the lysine is covalently linked to a cholesterol moiety or a lipid moiety, either directly or by means of a hydrophilic linker. In particular embodiments, the lipid moiety is a palmitoyl.

In further aspects of the above peptides, $L_1$ is a linker moiety. In particular aspects, the linker moiety is a hydrophilic linker moiety. In further still aspects, the linker moiety comprises one or more gamma-glutamic acid residues and in other aspects, the linker moiety is 1-amino-4,7,10-tioxa-13-tridecanamine succinimic acid.

In particular embodiments of the above peptide, the peptide comprises a structure selected from OXM70 (SEQ ID NO:12); OXM110 (SEQ ID NO:19); OXM115 (SEQ ID NO:21); OXM177 (SEQ ID NO:24); OXM212 (SEQ ID NO:27); OXM213 (SEQ ID NO:28); OXM216 (SEQ ID NO:29); OXM290 (SEQ ID NO:46); OXM301 (SEQ ID NO:51); or OXM325 (SEQ ID NO:65). In further particular embodiments of the above peptide, the peptide comprises a structure selected from OXM237 (SEQ ID NO:31); OXM238 (SEQ ID NO:32); OXM259 (SEQ ID NO:33); OXM260 (SEQ ID NO:34); OXM261 (SEQ ID NO:35); OXM262 (SEQ ID NO:36); OXM263 (SEQ ID NO:37); OXM264 (SEQ ID NO:38); OXM265 (SEQ ID NO:39); OXM266 (SEQ ID NO:40); OXM267 (SEQ ID NO:41); OXM268 (SEQ ID NO:42); OXM306 (SEQ ID NO:43); OXM307 (SEQ ID NO:44); and OXM308 (SEQ ID NO:45).

In particular embodiments of the above peptide when the peptide lacks RNRNNIA (SEQ ID NO:104), the peptide comprises a structure selected from OXM291 (SEQ ID NO:47); OXM292 (SEQ ID NO:48); OXM293 (SEQ ID NO:49); OXM294 (SEQ ID NO:50); OXM302 (SEQ ID NO:52); OXM303 (SEQ ID NO:53); OXM304 (SEQ ID NO:54); OXM305 (SEQ ID NO:55); OXM311 (SEQ ID NO:56); OXM312 (SEQ ID NO:57); OXM314 (SEQ ID NO:58); OXM313 (SEQ ID NO:59); OXM317 (SEQ ID NO:60); OXM318 (SEQ ID NO:61); OXM319 (SEQ ID NO:62); OXM323 (SEQ ID NO:64); OXM327 (SEQ ID NO:66); or OXM329 (SEQ ID NO:67).

In further particular embodiments when the peptide lacks RNRNNIA (SEQ ID NO:104), the peptide comprises the structure selected from OXM345 (SEQ ID NO:69); OXM355 (SEQ ID NO:70); OXM357 (SEQ ID NO:71); OXM359 (SEQ ID NO:72); OXM361 (SEQ ID NO:73); OXM373 (SEQ ID NO:74); OXM374 (SEQ ID NO:75); OXM380 (SEQ ID NO:76); OXM381 (SEQ ID NO:77); OXM383 (SEQ ID NO:78); OXM388 (SEQ ID NO:79); OXM392 (SEQ ID NO:80); OXM395 (SEQ ID NO:81); OXM398 (SEQ ID NO:82); OXM399 (SEQ ID NO:83); OXM400 (SEQ ID NO:84); OXM401 (SEQ ID NO:85); OXM404 (SEQ ID NO:86); OXM406 (SEQ ID NO:87); OXM407 (SEQ ID NO:88); OXM408 (SEQ ID NO:89); OXM410 (SEQ ID NO:91); OXM411 (SEQ ID NO:92); OXM412 (SEQ ID NO:93); OXM414 (SEQ ID NO:95); OXM415 (SEQ ID NO:96); OXM416 (SEQ ID NO:97; OXM417 (SEQ ID NO:98); OXM418 (SEQ ID NO:99; OXM419 (SEQ ID NO:100; OXM420 (SEQ ID NO:101); or OXM421 (SEQ ID NO:102).

Further provided is a peptide analog comprising the structure $$Z_1\text{-P-}L_1\text{-}Z_2$$

wherein P is a peptide having the amino acid sequence (SEQ ID NO: 106)
$HX_1QGTFTSDYSX_2YLDX_3X_4X_5AX_6DFVQWLX_7NTK$ wherein $X_1$ is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe); $X_2$ is Ser (S) or Lys (K); $X_3$ is Ser (S) or Glu (E); $X_4$ is an arginine (R) or glutamic acid (E) residue; $X_5$ is an arginine (R) or alanine (A) residue; $X_6$ is Gln (Q) or Lys (K); $X_7$ is a methionine (M), norleucine (Nle), methionine sulfoxide (m), or O-methyl-L-homoserine (o) residue;

$Z_1$ is an optionally present protecting group that, if present, is joined to the N-terminal amino group, $L_1$ is optional but when present is a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In further aspects of the above peptides, $Z_2$ is a cysteine residue, which in particular embodiments, can be covalently linked by its thiol group to a cholesterol moiety or a lipid moiety. In other embodiments, the cholesterol moiety or lipid moiety is covalently linked to the thiol group of the cysteine by a hydrophilic linker. In particular aspects, the hydrophilic linker is an ethoxy polymer that includes one to twenty-four ethoxy units or in more specific aspects, the hydrophilic linker is an ethoxy polymer that includes four ethoxy units.

In further aspects of the above peptides, $Z_2$ is a lysine residue, which in particular embodiments, the ε-amino group of the lysine is covalently linked to a cholesterol moiety or a lipid moiety, either directly or by means of a hydrophilic linker. In particular embodiments, the lipid moiety is a palmitoyl.

In further aspects of the above peptides, $L_1$ is a linker moiety. In particular aspects, the linker moiety is a hydrophilic linker moiety. In further still aspects, the linker moiety comprises one or more gamma-glutamic acid residues and in other aspects, the linker moiety is 1-amino-4,7,10-tioxa-13-tridecanamine succinimic acid.

In particular embodiments of the above peptide, the peptide comprises a structure selected from OXM291 (SEQ ID NO:47); OXM292 (SEQ ID NO:48); OXM293 (SEQ ID NO:49); OXM294 (SEQ ID NO:50); OXM302 (SEQ ID NO:52); OXM303 (SEQ ID NO:53); OXM304 (SEQ ID NO:54); OXM305 (SEQ ID NO:55); OXM311 (SEQ ID NO:56); OXM312 (SEQ ID NO:57); OXM314 (SEQ ID NO:58); OXM313 (SEQ ID NO:59); OXM317 (SEQ ID NO:60); OXM318 (SEQ ID NO:61); OXM319 (SEQ ID NO:62); OXM323 (SEQ ID NO:64); OXM327 (SEQ ID NO:66); or OXM329 (SEQ ID NO:67).

In further particular embodiments, the peptide comprises the structure selected from OXM345 (SEQ ID NO:69); OXM355 (SEQ ID NO:70); OXM357 (SEQ ID NO:71); OXM359 (SEQ ID NO:72); OXM361 (SEQ ID NO:73); OXM373 (SEQ ID NO:74); OXM374 (SEQ ID NO:75); OXM380 (SEQ ID NO:76); OXM381 (SEQ ID NO:77); OXM383 (SEQ ID NO:78); OXM388 (SEQ ID NO:79); OXM392 (SEQ ID NO:80); OXM395 (SEQ ID NO:81); OXM398 (SEQ ID NO:82); OXM399 (SEQ ID NO:83); OXM400 (SEQ ID NO:84); OXM401 (SEQ ID NO:85); OXM404 (SEQ ID NO:86); OXM406 (SEQ ID NO:87); OXM407 (SEQ ID NO:88); OXM408 (SEQ ID NO:89); OXM410 (SEQ ID NO:91); OXM411 (SEQ ID NO:92); OXM412 (SEQ ID NO:93); OXM414 (SEQ ID NO:95); OXM415 (SEQ ID NO:96); OXM416 (SEQ ID NO:97); OXM417 (SEQ ID NO:98); OXM418 (SEQ ID NO:99); OXM419 (SEQ ID NO:100; OXM420 (SEQ ID NO:101); or OXM421 (SEQ ID NO:102).

Further provided is a peptide analog comprising the structure $Z_1$-P-$L_1$-$Z_2$ wherein P is a peptide having the amino acid sequence

```
                                           (SEQ ID NO: 107)
HX1QGTFTSDYSX2YLDX3X4X5AX6DEVQWLX7NTKRNRNNIA
``` wherein $X_1$ is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe); $X_2$ is Ser (S) or Lys (K); $X_3$ is Ser (S) or Glu (E); $X_4$ is an arginine (R) or glutamic acid (E) residue; $X_5$ is an arginine (R) or alanine (A) residue; $X_6$ is Gln (Q) or Lys (K); $X_7$ is a methionine (M), norleucine (Nle), methionine sulfoxide (m), or O-methyl-L-homoserine (o) residue;

$Z_1$ is an optionally present protecting group that, if present, is joined to the N-terminal amino group, $L_1$ is optional but when present is a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In further aspects of the above peptides, $Z_2$ is a cysteine residue, which in particular embodiments, can be covalently linked by its thiol group to a cholesterol moiety or a lipid moiety. In other embodiments, the cholesterol moiety or lipid moiety is covalently linked to the thiol group of the cysteine by a hydrophilic linker. In particular aspects, the hydrophilic linker is an ethoxy polymer that includes one to twenty-four ethoxy units or in more specific aspects, the hydrophilic linker is an ethoxy polymer that includes four ethoxy units.

In further aspects of the above peptides, $Z_2$ is a lysine residue, which in particular embodiments, the ε-amino group of the lysine is covalently linked to a cholesterol moiety or a lipid moiety, either directly or by means of a hydrophilic linker. In particular embodiments, the lipid moiety is a palmitoyl.

In further aspects of the above peptides, $L_1$ is a linker moiety. In particular aspects, the linker moiety is a hydrophilic linker moiety. In further still aspects, the linker moiety comprises one or more gamma-glutamic acid residues and in other aspects, the linker moiety is 1-amino-4,7,10-tioxa-13-tridecanamine succinimic acid.

In particular embodiments of the above peptide, the peptide comprises a structure selected from OXM290 (SEQ ID NO:46); OXM301 (SEQ ID NO:51); OXM321 (SEQ ID NO:63); OXM325 (SEQ ID NO:65); or OXM330 (SEQ ID NO:68).

In further particular embodiments of the above peptide, the peptide comprises a structure selected from OXM70 (SEQ ID NO:12); OXM110 (SEQ ID NO:19); OXM115 (SEQ ID NO:21); OXM177 (SEQ ID NO:24); OXM212 (SEQ ID NO:27); OXM213 (SEQ ID NO:28); or OXM216 (SEQ ID NO:29).

In further particular embodiments of the above peptide, the peptide comprises a structure selected from OXM237 (SEQ ID NO:31); OXM238 (SEQ ID NO:32); OXM259 (SEQ ID NO:33); OXM260 (SEQ ID NO:34); OXM261 (SEQ ID NO:35); OXM262 (SEQ ID NO:36); OXM263 (SEQ ID NO:37); OXM264 (SEQ ID NO:38); OXM265 (SEQ ID NO:39); OXM266 (SEQ ID NO:40); OXM267 (SEQ ID NO:41); OXM268 (SEQ ID NO:42); OXM306 (SEQ ID NO:43); OXM307 (SEQ ID NO:44); and OXM308 (SEQ ID NO:45).

Further provided are peptide analogs that are a dual GLP-1/glucagon receptor (GCGR) agonist and have a pI of less than 6.0. Peptide analogs comprising a cholesterol or fatty acid moiety and have a pI of less than 6 have been found to have a reduced capacity for stimulating mast cell degranulation as determined by a in vitro counterscreening assay using the human mast cell line LAD2. Therefore, further provided is a peptide analog comprising the amino acid sequence HSQGTFTSDYSKYLDSRRAQD-FVQWLMNTK (SEQ ID NO:109) in which the second amino acid from the N-terminus of the peptide is substituted with an amino acid that renders the peptide resistant to cleavage and inactivation by dipeptidyl peptidase IV; the peptide includes a lipid or cholesterol moiety covalently linked to the peptide by a spacer comprising one or more gamma-glutamic acid residues; the peptide optionally includes one to three amino acid substitutions in addition to the substitution at position 2; and the peptide optionally includes a protecting group that, if present, is joined to the C-terminal carboxy group of the peptide; wherein the peptide analog has a pI of less than 6.0 and is a dual GLP-1 receptor agonist and glucagon receptor agonist, and pharmaceutically acceptable salts thereof. In particular aspects, peptide analogs have a pI between 4 and 6, or a pI of about 5.0, for example, a pI of about 5.4.

In further aspects, the amino acid substituted for the second amino acid from the N-terminus of the peptide analog is selected from the group consisting of D-serine, α-aminoisobutyric acid, and 1-amino-1-cyclobutane carboxylic acid.

In particular aspects, the peptide analog includes a cholesterol moiety covalently linked to the thiol group of a cysteine residue that is covalently linked to the ε-amino group of the lysine residue at the C-terminus of the peptide analog by a spacer comprising one or more gamma glutamic acid residues. In a further embodiment, the cholesterol moiety is covalently linked to the thiol group by a hydrophilic linker, which in particular embodiments is an ethoxy polymer that includes one to twelve ethoxy units for example, an ethoxy polymer that includes four ethoxy units.

In particular aspects, the peptide analog includes a lipid moiety covalently linked to the ε-amino group of a lysine residue: in particular embodiments the lipid moiety is a fatty acid such as a palmitoyl, myristoyl, or stearoyl moiety. In a further embodiment, the lipid moiety is covalently linked to the ε-amino group of the lysine residue by one or more gamma-glutamic acid residues. In a further embodiment, the lipid moiety is covalently linked to the ε-amino group of the lysine residue at the C-terminus by one or more gamma-glutamic acid residues. In a further embodiment, the lipid moiety is covalently linked to the ε-amino group of the lysine residue by one or more gamma-glutamic acid residues and the lysine residue linked to the lysine residue at the C-terminus by one or more gamma-glutamic acid residues.

In further aspects, the peptide analog further includes one or more amino acid substitutions at amino acid positions selected from the group consisting of positions 10, 12, 16, 17, 18, and 27. In particular embodiments, the peptide analog includes one or more amino acid substitutions selected from the group consisting of lysine for the tyrosine at position 10, serine for the lysine at position 12, glutamic acid or α-aminoisobutyric acid for the serine at position 16, glutamic acid for the arginine at position 17, alanine for the arginine at position 18, lysine for the glutamine at position 20, and norleucine or O-methyl-L-homoserine for the methionine at position 27.

In a further embodiment, the tyrosine at position 10 in the peptide analog is replaced with a lysine and the lipid moiety is covalently linked to the ε-amino group of the lysine residue by one or more gamma-glutamic acid residues. In another embodiment, the glutamine at position 20 in the peptide analog is replaced with lysine and the lipid moiety is covalently linked to the ε-amino group of the lysine by one or more gamma-glutamic acid residues. In either embodiment, the peptide analog further includes one or more gamma-glutamic acid residues covalently linked to the C-terminus.

Further provided is a peptide analog comprising the structure $Z_1$-P-M-$Z_2$ wherein P is a peptide having the amino acid sequence (SEQ ID NO: 110)
HX$_1$QGTFTSDX$_2$SX$_3$YLDX$_4$X$_5$X$_6$AX$_7$DEVQWLX$_8$NTKX$_9$X$_{10}$ wherein $X_1$ is a D-serine, α-aminoisobutyric acid (aib), 1-Amino-1-cyclobutane carboxylic acid (Acb) residue; 1-Amino-1-cyclohexane carboxylic acid (Acx); alpha-aminobutyric acid (Abu); D-alpha-aminobutyric acid (D-Abu); Aminovaleric acid Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe) residue; $X_2$ is a tyrosine (Y) or lysine (K) residue; $X_3$ is serine (S) or lysine (K) residue; $X_4$ is serine (S), α-aminoisobutyric acid (aib), or glutamic acid (E) residue; $X_5$ is an arginine (R) or glutamic acid (E) residue; $X_6$ is an arginine (R) or alanine (A) residue; $X_7$ is a glutamine (Q) or lysine (K) residue; $X_8$ is a methionine (M), norleucine (Nle), methionine sulfoxide (m), or O-methyl-L-homoserine (o) residue; $X_9$ is a gamma glutamic acid (γGlu) residue; $X_{10}$ is a gamma glutamic acid (γGlu) residue or absent; $Z_1$ is an optionally present protecting group that, if present, is joined to the N-terminal amino group, M is (i) a cysteine residue covalently linked to a cholesterol moiety by a hydrophilic linker, (ii) a lysine residue covalently linked to a lipid moiety by a spacer comprising one or more gamma glutamic acid residues, or (iii) a lipid moiety, wherein M is covalently linked to C-terminal or internal amino acid of P by a spacer comprising one or more gamma-glutamic acid residues; and $Z_2$ is an optionally present protecting group that, if present, is joined to the C-terminal carboxy group; and pharmaceutically acceptable salts thereof, wherein the peptide analog or salt thereof has a pI of less than 6.0 and is a dual GLP-1 receptor agonist and glucagon receptor agonist. In particular aspects, peptide analogs have a pI between 4 and 6, or a pI of about 5.0, 5.1, 5.2, 5.3, 5.4, 5.5, 5.6, 5.7, 5.8, or 5.9, or a pI of about 5.4 to 5.5.

In further aspects of the peptide analog, M is a cysteine residue covalently linked to a cholesterol moiety with a hydrophilic linker and the cysteine residue is linked to the C-terminus of P. In further embodiments, the hydrophilic linker is an ethoxy polymer that includes one to twenty-four ethoxy units, which in particular aspects can include for example, four ethoxy units.

In further aspects, M is a lysine residue covalently linked to a lipid moiety by a spacer comprising one or more gamma glutamic acid residues and the lysine residue is linked to the C-terminus of P or M is a lysine residue covalently linked to a lipid moiety by a spacer comprising one or more gamma glutamic acid residues and the lysine residue is at position $X_2$ or $X_7$ of P. In particular aspects, the lipid moiety is a palmitoyl, myristoyl, or stearoyl moiety.

In particular aspects, the peptide analog is OXM317 (SEQ ID NO:60); OXM318 (SEQ ID NO:61); OXM319 (SEQ ID NO:62); OXM323 (SEQ ID NO:64); OXM327 (SEQ ID NO:66); or OXM329 (SEQ ID NO:67). In further aspects, the peptide analog is OXM345 (SEQ ID NO:69); OXM355 (SEQ ID NO:70); OXM357 (SEQ ID NO:71); OXM359 (SEQ ID NO:72); OXM361 (SEQ ID NO:73); OXM373 (SEQ ID NO:74); OXM374 (SEQ ID NO:75); OXM380 (SEQ ID NO:76); OXM381 (SEQ ID NO:77); OXM383 (SEQ ID NO:78); OXM388 (SEQ ID NO:79); OXM392 (SEQ ID NO:80); OXM395 (SEQ ID NO:81); OXM398 (SEQ ID NO:82); OXM399 (SEQ ID NO:83); OXM400 (SEQ ID NO:84); OXM401 (SEQ ID NO:85); OXM404 (SEQ ID NO:86); OXM406 (SEQ ID NO:87); OXM407 (SEQ ID NO:88); OXM408 (SEQ ID NO:89); OXM410 (SEQ ID NO:91); OXM411 (SEQ ID NO:92); OXM412 (SEQ ID NO:93); OXM414 (SEQ ID NO:95); OXM415 (SEQ ID NO:96); OXM416 (SEQ ID NO:97; OXM417 (SEQ ID NO:98); OXM418 (SEQ ID NO:99; OXM419 (SEQ ID NO:100; OXM420 (SEQ ID NO:101); or OXM421 (SEQ ID NO:102).

Further provided is the use of any one of the aforementioned peptides and pharmaceutically acceptable salts thereof, in the manufacture of a medicament for the treatment of a metabolic disorder.

DEFINITIONS

A GLP-1 agonist is a peptide, small molecule, or chemical compound that binds to the GLP-1 receptor and stimulates the same biological activity as does GLP-1. In one embodiment, an agonist for the GLP-1 receptor binds to the receptor with at least 1% of the affinity as native GLP-1. In another embodiment, an agonist for the GLP-1 receptor binds to the receptor with an equal or greater affinity than native GLP-1.

A glucagon agonist is a peptide, small molecule, or chemical compound that binds to the glucagon receptor and stimulates the same biological activity as does glucagon. In one embodiment, an agonist for the glucagon receptor binds to the receptor with at least 1% of the affinity as native glucagon. In another embodiment, an agonist for the glucagon receptor binds to the receptor with an equal or greater affinity than native glucagon.

As used herein a "dual GLP1/glucagon receptor agonist" is "GLP1 receptor/glucagon receptor co-agonist molecule", which exhibit activity at both the glucagon receptor and the GLP1 receptor. In general, a dual GLP1 receptor agonist and glucagon receptor agonist exhibits activity at the glucagon receptor of at least about 10% relative to native glucagon and also exhibits activity at the GLP-1 receptor of at least about 10% relative to native GLP-1.

BRIEF DESCRIPTION OF THE DRAWINGS

FIG. 9A shows the cumulative change in food intake. FIG. 9B shows the cumulative change in body weight. FIG. 9C shows basal glucose levels over several days of the study. FIG. 9D shows IPGTT assay on day 13 of the study.

DETAILED DESCRIPTION OF THE INVENTION

Figure 1A:
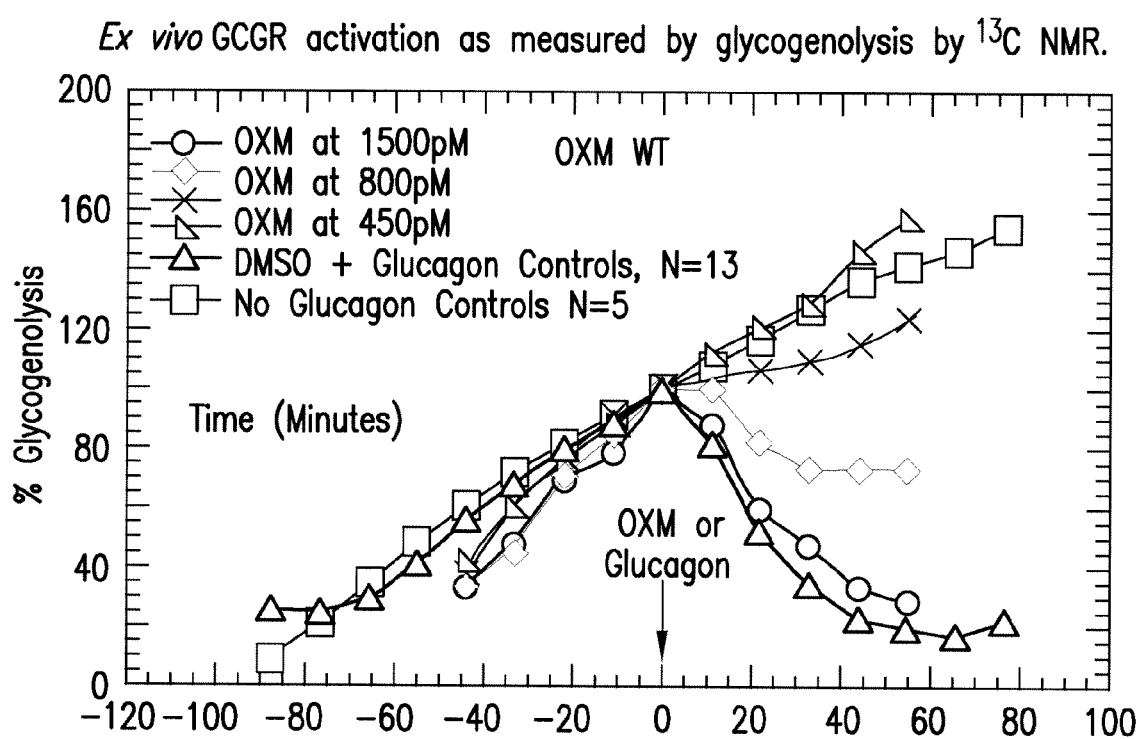
FIGS. 1A and 1B show the results of an ex vivo assay comparing glycogenolysis of native OXM to OXM(Q3E). The Figure shows that native OXM induces glycogenolysis in a dose dependent fashion and induces full glycogenolysis at 1.5 nM and has an approximate $EC_{50}$ of 0.5 nM whereas OXM-Q3E induced only about 58% at 300 nM, consistent with its poor GCGR agonist potency.

OXM-based therapy has the potential to favorably impact both obesity and, the as yet to be carefully characterized, concomitant effects on improving diabetes. Weight loss efficacy and reduction in food intake upon peripheral administration of OXM has been well validated in humans (Wynne et al., Diabetes 54: 2390-2395 (2005)). More recently, OXM has been shown to increase metabolic rate and specifically activity-related energy expenditure in obese subjects (Wynne et al., Int. J. Obes. 30: 1729-1736 (2006), advance online publication, Apr. 18, 2006; doi:10.1038/sj.ijo.0803344). OXM has also been shown to reduce body weight in humans (See, for example, Published International Application Nos. WO03/022304, WO2004/062685, and WO2006/134340); however, the effects of the OXM peptide and similar dual GLP-1 receptor/glucagon receptor (GLP-1R/GCGR) agonists on the glycemic control independent of weight loss have not been systematically studied. The ability of OXM to have agonist activity at both the glucagon receptor and the GLP-1 receptor makes it an attractive candidate for treating metabolic diseases where it is desirable that the treatment positively interact with the glucagon and GLP-1 receptors.

OXM (and GLP-1) has a very short half-life and is rapidly inactivated by the cell surface dipeptidyl peptidase IV (DPP-IV). Mutations can be incorporated into the OXM peptide to render the peptide resistant to DPP-IV cleavage; however, many of these mutations have also been found to inactivate the native peptide or adversely affect the ability of the peptide to interact with the glucagon receptor (GCGR) or GLP-1 receptor (GLP-1R) (See Published International Application No. WO2007/100535, which is incorporated herein in its entirety). OXM (and GLP-1) is also rapidly cleared by the kidneys. Conjugation of peptides with bulky substituents such as polyethylene glycol can reduce renal clearance of the peptide; however, when these bulky substituents have been incorporated into the OXM peptide, many of resulting OXM peptide analogs have been found to have a reduced ability or no ability to effectively interact with the glucagon receptor. Before effective therapies for metabolic diseases based on administering OXM peptides can be advanced, the problems associated with stability and pharmacokinetics need to be solved.

The OXM peptide analogs disclosed herein solve these problems.

First, the limited in vivo stability of native OXM and GLP-1 due to cleavage by DPP-IV and rapid renal clearance, which necessitates frequent dosing (t.i.d. s.c. injections for OXM, continuous infusion for GLP-1) at high doses in humans has been solved by mutating the site of DPP-IV cleavage (the penultimate residue at the N-terminus) and lipidating the OXM peptide to increase in vivo half-life ($t_{1/2}$). It is anticipated that the $t_{1/2}$ of the lipidated (such as acylated or conjugated with a cholesterol moiety) OXM peptide analogs in humans will be suitable for at least once daily administration. The OXM peptide analogs disclosed herein are more convenient for therapeutic purposes than native OXM, which requires t.i.d. dosing. Second, the tolerability profile of polypeptides of the current invention is anticipated to be similar to that of native OXM in humans, which may be superior to that of conventional GLP-1 mimetics like exenatide and liraglutide. The chronic efficacy of the OXM analogs disclosed herein may therefore be better than conventional GLP-1 mimetics, such as Byetta® (Amylin Pharmaceuticals), due to minimal nausea and vomiting, which have typically been dose limiting for the GLP-1 mimetics. Unlike the latter, no dose-titrations to mitigate nausea may be required for polypeptides of this invention.

Third, no systematic studies have been performed to evaluate the potential for improving glucose control. Since OXM is potent agonist of the glucagon receptor, the expectation would be that chronic administration would lead to impaired glucose control (hyperglycemia). However, unexpectedly, the OXM analogs disclosed herein, which incorporate a balanced GLP-1 receptor and GCGR co-agonism, gives enhanced reductions in food intake and body weight with chronic administration and results in improved glucose tolerance. OXM peptide analogs that have dual GLP-1 receptor (GLP-1R) and glucagon receptor (GCGR) agonist activity are indicated herein as (+/+). OXM peptide analogs that are GLP-1 agonists only are indicated herein as (+/0).

To produce a long acting OXM peptide analogs has not been straight forward. Our initial studies focused on site-specific conjugation of a bulky poly-ethylene glycol (PEG) substituent at promising locations throughout the peptide. Surprisingly, addition of PEG at all positions tested resulted in a significant reduction in GCGR and/or GLP-1R potency. We therefore investigated other methods to improve pharmaco kinetic properties, whilst maintaining GCGR activity. Addition of a cholesterol conjugate to various positions in the peptide indicated C-terminal conjugation as the most favorable method. In vitro and in vivo studies, however, indicated that the cholesteroylation resulted in a significant serum shift of potency and decreased in vivo efficacy. Therefore, further investigation resulted in the non-trivial inclusion of a hydrophilic linker between the peptide and cholesterol group, or direct addition of an acyl-chain to a C-terminal residue.

Primary indications in which the OXM analogs disclosed herein can be used for is the treatment of obesity and/or diabetes. Secondary indications are metabolic syndrome, hyperglycemia, impaired fasting glucose, and other prediabetic states. Further indications include all indications for GLP-1 such as irritable bowel syndrome and other absorptive diseases of the gut, ischemia, stroke, and neurological disorders including anxiety, impaired cognition, and Alzheimer's disease.

Based on published human studies with OXM, the OXM analogs disclosed herein are anticipated to exhibit at least comparable if not superior efficacy and a better safety profile than current anti-obesity agents such as orlistat (Xenical® (Roche), a lipase inhibitor) and sibutramine (Meridia® (Abbott Laboratories), a seratonin/norepinephrine re-uptake inhibitor), for which GI intolerance (diarrhea, flatulence) and hypertension are common side effects, respectively.

In particular aspects, the OXM peptide analogs optionally includes a protecting group covalently joined to the N-terminal amino group. A protecting group covalently joined to the N-terminal amino group of the peptide reduces the reactivity of the amino terminus under in vivo conditions. Amino protecting groups include —$C_{1-10}$ alkyl, —$C_{1-10}$ substituted alkyl, —$C_{2-10}$ alkenyl, —$C_{2-10}$ substituted alkenyl, aryl, —$C_{1-6}$ alkyl aryl, —C(O)—(CH$_2$)$_{1-6}$—COOH, —C(O)—$C_{1-6}$ alkyl, —C(O)-aryl, —C(O)—O—$C_{1-6}$ alkyl, or —C(O)—O-aryl. In particular embodiments, the amino terminus protecting group is selected from the group consisting of acetyl, propyl, succinyl, benzyl, benzyloxycarbonyl, and t-butyloxycarbonyl. Deamination of the N-terminal amino acid is another modification that is contemplated for reducing the reactivity of the amino terminus under in vivo conditions.

The OXM peptide analogs may be modified to have a protecting group covalently joined to the C-terminal carboxy group, which reduces the reactivity of the carboxy terminus under in vivo conditions. For example, carboxylic acid groups of the peptide, whether carboxyl-terminal or side chain, may be provided in the form of a salt of a pharmacologically-acceptable cation or esterified to form a $C_{1-6}$ ester, or converted to an amide of formula NRR$_2$ wherein R and R$_2$ are each independently H or $C_{1-6}$ alkyl, or combined to form a heterocyclic ring, such as a 5- or 6-membered ring. The carboxy terminus protecting group is preferably attached to the α-carbonyl group of the last amino acid. Carboxy terminus protecting groups include, but are not limited to, amide, methylamide, and ethylamide. Amino groups of the peptide, whether N-terminal or side chain, may be in the form of a pharmacologically-acceptable acid addition salt, such as the HCl, HBr, acetic, benzoic, toluene sulfonic, maleic, tartaric, and other organic salts, or may be modified to $C_{1-6}$ alkyl or dialkyl amino or further converted to an amide.

The OXM peptide analogs that are capable of acting as dual GLP-1 and glucagon agonists comprise the amino acid sequence of a human oxyntomodulin (OXM) shown in SEQ ID NO:1 wherein the second amino acid from the N-terminus is substituted with an amino acid that renders the peptide resistant to cleavage and inactivation by dipeptidyl peptidase IV; a lipid or cholesterol moiety covalently linked to the OXM peptide analog; optionally one to three amino acid substitutions in addition to the substitution at position 2; and optionally has a protecting group that, if present, is joined to the C-terminal carboxy group of the peptide. In further embodiments, the peptide analogs further lack the amino acid sequence RNRNNIA (SEQ ID NO:104). In general, OXM peptide analogs having the above structure will act as a dual GLP-1 receptor and glucagon receptor agonist and have a serum half-life greater than the serum half-life of native human OXM.

In more specific embodiments, the OXM peptide analog can be represented by the structure $Z_1$-P-$L_1$-$Z_2$ wherein P is a peptide having the amino acid sequence (SEQ ID NO: 103)
HX$_1$QGTFTSDYSKYLDSX$_2$X$_3$AQDFVQWLX$_4$NTK wherein $X_1$ is a D-serine or α-aminoisobutyric acid (aib) residue; $X_2$ is an arginine (R) or glutamic acid (E) residue; $X_3$ is an arginine (R) or alanine (A) residue; $X_4$ is a methionine (M), norleucine (Nle), or O-methyl-L-homoserine (o) residue;

$Z_1$ is an optionally present protecting group that, if present, is joined to the N-terminal amino group, $L_1$ is optional but when present is amino acid sequence RNRNNIA (SEQ ID NO:104) or a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In a further embodiment, the OXM peptide analog can be represented by the structure $Z_1$-P-$L_1$-$Z_2$ wherein P is a peptide having the amino acid sequence (SEQ ID NO: 103)
HX$_1$QGTFTSDYSKYLDSX$_2$X$_3$AQDFVQWLX$_4$NTK wherein $X_1$ is a D-serine or α-aminoisobutyric acid (aib) residue; $X_2$ is an arginine (R) or glutamic acid (E) residue; $X_3$ is an arginine (R) or alanine (A) residue; $X_4$ is a methionine (M), norleucine (Nle), or O-methyl-L-homoserine (o) residue;

$Z_1$ is an optionally present protecting group that, if present, is joined to the N-terminal amino group, $L_1$ is optional but when present is a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In a further embodiment, the OXM peptide analog can be represented by the structure $Z_1$-P-$L_1$-$Z_2$ wherein P is a peptide having the amino acid sequence (SEQ ID NO: 105)
HX$_1$QGTFTSDYSKYLDSX$_2$X$_3$AQDFVQWLX$_4$NTKRNRNNIA wherein $X_1$ is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid (Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe); $X_2$ is an arginine (R) or glutamic acid (E) residue; $X_3$ is an arginine (R) or alanine (A) residue; $X_4$ is a methionine (M), norleucine (Nle), or O-methyl-L-homoserine (o) residue;

$Z_1$ is an optionally present protecting group that, if present, is joined to the N-terminal amino group, $L_1$ is optional but when present is amino acid sequence RNRNNIA (SEQ ID NO:104) or a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In further specific embodiments, the OXM peptide analog can be represented by the structure $Z_1$-P-$L_1$-$Z_2$ wherein P is a peptide having the amino acid sequence (SEQ ID NO: 106)
HX$_1$QGTFTSDYSX$_2$YLDX$_3$X$_4$X$_5$AX$_6$DFVQWLX$_7$NTK wherein $X_1$ is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe); $X_2$ is Ser (S) or Lys (K); $X_3$ is Ser (S) or Glu (E); $X_4$ is an arginine (R) or glutamic acid (E) residue; $X_5$ is an arginine (R) or alanine (A) residue; $X_6$ is Gln (Q) or Lys (K); $X_7$ is a methionine (M), norleucine (Nle), methionine sulfoxide (m), or O-methyl-L-homoserine (o) residue;

$Z_1$ is an optionally present protecting group that, if present, is joined to the N-terminal amino group, $L_1$ is optional but when present is amino acid sequence RNRNNIA (SEQ ID NO:104) or a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In a further embodiment, the OXM peptide analog can be represented by the structure $Z_1$-P-$L_1$-$Z_2$ wherein P is a peptide having the amino acid sequence (SEQ ID NO: 106)
HX₁QGTFTSDYSX₂YLDX₃X₄X₅AX₆DFVQWLX₇NTK wherein $X_1$ is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe); $X_2$ is Ser (S) or Lys (K); $X_3$ is Ser (S) or Glu (E); $X_4$ is an arginine (R) or glutamic acid (E) residue; $X_5$ is an arginine (R) or alanine (A) residue; $X_6$ is Gln (Q) or Lys (K); $X_7$ is a methionine (M), norleucine (Nle), methionine sulfoxide (m), or O-methyl-L-homoserine (o) residue;

$Z_1$ is an optionally present protecting group that, if present, is joined to the N-terminal amino group, $L_1$ is optional but when present is a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In a further embodiment, the OXM peptide analog can be represented by the structure $Z_1$-P-$L_1$-$Z_2$ wherein P is a peptide having the amino acid sequence (SEQ ID NO: 107)
HX₁QGTFTSDYSX₂YLDX₃X₄X₅AX₆DEVQWLX₇NTKRNRNNIA wherein $X_1$ is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe); $X_2$ is Ser (S) or Lys (K); $X_3$ is Ser (S) or Glu (E); $X_4$ is an arginine (R) or glutamic acid (E) residue; $X_5$ is an arginine (R) or alanine (A) residue; $X_6$ is Gln (Q) or Lys (K); $X_7$ is a methionine (M), norleucine (Nle), methionine sulfoxide (m), or O-methyl-L-homoserine (o) residue;

$Z_1$ is an optionally present protecting group that, if present, is joined to the N-terminal amino group, $L_1$ is optional but when present is a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In further specific embodiments, the OXM peptide analog can be represented by the structure $Z_1$-P-$L_1$-$Z_2$ wherein P is a peptide having the amino acid sequence (SEQ ID NO: 108)
HX₁QGTFTSDX₂SX₃YLDX₄X₅X₆AX₇DFVQWLX₈NTKX₉ wherein $X_1$ is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe); $X_2$ is Tyr or Lys; $X_3$ is Ser (S) or Lys (K); $X_4$ is Ser (S) or Glu (E); $X_5$ is an arginine (R) or glutamic acid (E) residue; $X_6$ is an arginine (R) or alanine (A) residue; $X_7$ is Gln (Q) or Lys (K); $X_8$ is a methionine (M), norleucine (Nle), methionine sulfoxide (m), or O-methyl-L-homoserine (o) residue; $X_9$ is optional but when present is one or more gamma glutamic acid residues.

$Z_1$ is an optionally present protecting group that, if present, is joined to the N-terminal amino group, $L_1$ is optional but when present is amino acid sequence RNRNNIA (SEQ ID NO:104) or a linker moiety; $Z_2$ is optional but when present is a lysine (K) residue, a lysine residue covalently linked to a lipid moiety, a lysine residue covalently linked to a cholesterol moiety, a cysteine (C) residue, a cysteine residue covalently linked to a lipid moiety; a cysteine residue covalently linked to a cholesterol moiety; and P or $Z_2$ optionally includes a protecting group that, if present, is joined to the C-terminal carboxy group; and pharmaceutically acceptable salts thereof. $L_1$-$Z_2$ can be linked to the C-terminal amino acid of P or to an internal amino acid of P.

In each of the above embodiments, the lipid or cholesterol moiety can be directly or indirectly linked to the side chain of an amino acid. When the lipid or cholesterol moiety is indirectly linked to the amino acid side-chain, the lipid or cholesterol moiety is linked to the amino acid side-chain by means of a linker moiety. In particular aspects, the lipid or cholesterol is directly linked to the side chain of an amino acid which is then linked to the OXM peptide analog by a linker moiety ($L_1$).

In particular embodiments of the OXM analogs disclosed herein, when residues 16 and 20 are Glu and Lys, respectively, the side chains of said residues can participate in a lactam bridge between said Glu and Lys residues.

In many embodiments, the linker moiety is a hydrophilic linker. The chemical structure of the linker moiety is not critical, however, since it serves primarily as a spacer. However, in certain embodiments, the linker moiety may itself provide improved properties to the OXM peptide analogs. Examples of linker moieties, include but are not limited to, amino acids and peptides; alkyl linkers such as —NH—$(CH_2)_s$—C(O)—, wherein s=2-20, these alkyl linkers may further be substituted by any non-sterically hindering group such as lower alkyl (for example, $C_{1-6}$) lower acyl, halogen (for example, Cl, Br), CN, $NH_2$, phenyl, and the like; an ethoxy polymer that includes one to twelve ethoxy units; Ttds (1-amino-4,7,10-trioxa-13-tridecanamine-succinamic acid); and one, two, three, or more gamma glutamic acid residues.

In general, the linker moiety is covalently linked to the C-terminal amino acid of the peptide (P) and $Z_2$ is covalently linked to the linker moiety. In particular aspects, the linker moiety is covalently linked to an internal amino acid of P and $Z_2$ is covalently linked to the linker moiety. In further aspects, when $L_1$-$Z_2$ are covalently linked to an internal amino acid of P, $X_9$ can include one or more gamma glutamic acid residues.

The OXM peptide analogs include diastereomers as well as their racemic and resolved enantiomerically pure forms. In general, the amino acids are in the L-form with particular amino acids in D-form. As is known in the art, individual amino acids can be represented as follows: A=Ala=Alanine; C=Cys=Cysteine; D=Asp=Aspartic Acid; E=Glu=Glutamic Acid; F=Phe=Phenylalanine; G=Gly=Glycine; H=His=Histidine; I=Ile=Isoleucine; K=Lys=Lysine; L=Leu=Leucine; M=Met=Methionine; N=Asn=Asparagine; P=Pro=Proline; Q=Gln=Glutamine; R=Arg=Arginine; S=Ser=Serine; T=Thr=Threonine; V=Val=Valine; W=Trp=Tryptophan; and Y=Tyr=Tyrosine.

Table 1 shows the structures for a representative number of OXM peptide analogs based on the full-length OXM molecule that have activity at both the glucagon receptor and the GLP-1 receptor (+/+). OXM peptide analogs OXM29, 208, 209 and 229 are peptide analogs precursors (thiolated peptides) that were used for the conjugation reaction with the bromo-cholesterol moieties.

TABLE 1

| SEQ ID NO | Name | Structure |
|---|---|---|
| | | OXM (+/+) Peptide Analogs |
| 4 | OXM29 | HαQGTFTSDYSKYLDSRRAQDFVQWLMNTKRNRNNIAC-$CONH_2$ |
| 8 | OXM36 | HsQGTFTSDYSKYLDSRRAQDFVQWLMNTKRNRNNIAC$_4$-$CONH_2$ |
| 12 | OXM70 | HαQGTFTSDYSKYLDSRRAQDFVQWLMNTKRNRNNIAC$_4$-$CONH_2$ |
| 19 | OXM110 | HsQGTFTSDYSKYLDSRRAQDFVQWLMNTKRNRNNIAK(palmitoyl)-$CONH_2$ |
| 21 | OXM115 | HsQGTFTSDYSKYLDSRRAQDFVQWLMNTKRNRNNIAC$_7$-$CONH_2$ |
| 24 | OXM177 | HαQGTFTSDYSKYLDSRRAQDFVQWLMNTKRNRNNIAK(palmitoyl)-$CONH_2$ |
| 25 | OXM208 | HαQGTFTSDYSKYLDSRRAQDFVQWLnNTKRNRNNIAC-$CONH_2$ |
| 26 | OXM209 | HαQGTFTSDYSKYLDSRRAQDFVQWLoNTKRNRNNIAC-$CONH_2$ |
| 27 | OXM212 | HαQGTFTSDYSKYLDSRRAQDFVQWLnNTKRNRNNIAC$_4$-$CONH_2$ |
| 28 | OXM213 | HαQGTFTSDYSKYLDSRRAQDFVQWLoNTKRNRNNIAC$_4$-$CONH_2$ |
| 29 | OXM216 | HαQGTFTSDYSKYLDSRRAQDFVQWLMNTKRNRNNIAC$_7$-$CONH_2$ |
| 30 | OXM229 | HsQGTFTSDYSKYLDSRRAQDFVQWLMNTKRNRNNIAC-$CONH_2$ |
| 31 | OXM237 | HsQGTFTSDYSKYLDSRRAQDFVQWLmNTKRNRNNIA-C$_7$-$CONH_2$ |

TABLE 1-continued

OXM (+/+) Peptide Analogs

| SEQ ID NO | Name | Structure |
|---|---|---|
| 32 | OXM238 | HsQGTFTSDYSKYLDSRRAQDFVQWLmNTKRNRNNIA-C$_5$-CONH$_2$ |
| 33 | OXM259 | H-Acx-QGTFTSDYSKYLDSRRAQDFVQWLMNTKRNRNNIA-CONH$_2$ |
| 34 | OXM260 | H-Abu-QGTFTSDYSKYLDSRRAQDFVQWLMNTKRNRNNIA-CONH$_2$ |
| 35 | OXM261 | H-(D-Abu)-QGTFTSDYSKYLDSRRAQDFVQWLMNTKRNRNNIA-CONH$_2$ |
| 36 | OXM262 | H-Nva-QGTFTSDYSKYLDSRRAQDFVQWLMNTKRNRNNIA-CONH$_2$ |
| 37 | OXM263 | H-Cpa-QGTFTSDYSKYLDSRRAQDFVQWLMNTKRNRNNIA-CONH$_2$ |
| 38 | OXM264 | H-Prg-QGTFTSDYSKYLDSRRAQDFVQWLMNTKRNRNNIA-CONH$_2$ |
| 39 | OXM265 | H-Alg-QGTFTSDYSKYLDSRRAQDFVQWLMNTKRNRNNIA-CONH$_2$ |
| 40 | OXM266 | H-(2-Cha)-QGTFTSDYSKYLDSRRAQDFVQWLMNTKRNRNNIA-CONH$_2$ |
| 41 | OXM267 | H-(Dtbg)-QGTFTSDYSKYLDSRRAQDFVQWLMNTKRNRNNIA-CONH$_2$ |
| 42 | OXM268 | H-Vg-QGTFTSDYSKYLDSRRAQDFVQWLMNTKRNRNNIA-CONH$_2$ |
| 43 | OXM306 | H-Acp-QGTFTSDYSKYLDSRRAQDFVQWLMNTKRNRNNIA-CONH$_2$ |
| 44 | OXM307 | H-Acb-QGTFTSDYSKYLDSRRAQDFVQWLMNTKRNRNNIA-CONH$_2$ |
| 45 | OXM308 | H-Acpe-QGTFTSDYSKYLDSRRAQDFVQWLMNTKRNRNNIA-CONH$_2$ |

α = α-aminoisobutyric acid; s = D-Ser; m = methionine sulfoxide; n = norleucine; o = O-methyl-L-homoserine; Acx = 1-Amino-1-cyclohexane carboxylic acid; Abu = α-aminobutyric acid; D-Abu = D-α-aminobutyric acid; Nva = Aminovaleric acid; Cpa = β-cyclopropyl-alanine; Prg = propargylglycine; Alg = Allylglycine; 2-Cha = 2-Amino-2-cyclohexyl-propanoic acid;
D-tbg = D-tertbutylglycine; Vg = Vinylglycine; Acp = 1-Amino-1-cyclopropane carboxylic acid; Acb = 1-Amino-1-cyclobutane carboxylic acid; Acpe = 1-Amino-1-cyclopentane carboxylic acid
$C_4$ = Cys(cholest-5-en-3-yl{[(2R)-3-amino-2-(amino)-3-oxopropyl]thio}acetate);
$C_5$ = Cys(CH$_2$CONH$_2$), corresponding to a cysteine residue in which the side-chain thiol was reacted with iodoacetamide;
$C_7$ = Cys(cholest-5-en-3-yl 1-{[(2R)-3-amino-2-(amino)-3-oxopropyl]thio}-2-oxo-6,9,12,15-tetraoxa-3-azaoctadecan-18-oate) or Cys(Oxa4-cholesterol).

OXM peptide analogs OXM36 and OXM115 were prepared from OXM229, which includes the native human OXM peptide but with a D-serine at amino acid position 2 and a cysteine residue in peptide linkage at the C-terminus and in which the C-terminal carboxy group has been amidated. OXM36 has the structure HsQGTFTSDYSKYLD-SRRAQDFVQWLMNTKRNRNNIAC$_4$-CONH$_2$ (SEQ ID NO:8) wherein C$_4$ is a cysteine residue in which cholest-5-en-3-yl{[(2R)-3-amino-2-(amino)-3-oxopropyl]thio}acetate is covalently linked thereto as shown below.

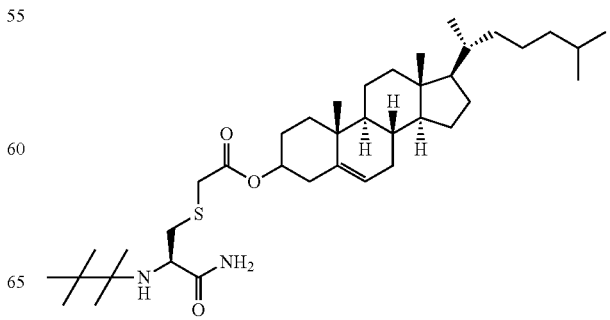

OXM115 has the structure HsQGTFTSDYSKYLDSR-RAQDFVQWLMNTKRNRNNIAC$_7$-CONH$_2$ (SEQ ID NO:21) wherein the C$_7$ is a cholest-5-en-3-yl 1-{[(2R)-3-amino-2-(amino)-3-oxopropyl]thio}-2-oxo-6,9,12,15-tetraoxa-3-azaoctadecan-18-oate (or Cys(Oxa4-cholesterol)) as shown below.

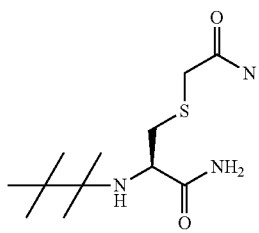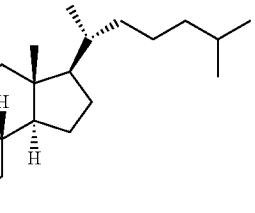

C$_7$ differs from C$_4$ in that it has a hydrophilic spacer formed by four ethylene glycol repeats (ethoxy units) between the cholesterol group and the cysteine moiety. The C7 group increases solubility of the resulting peptide-cholesterol conjugate. Moreover, in the presence of serum plasma, the peptide-C$_7$ conjugate shows a less prominent serum shift than peptide-C$_4$ conjugates. This was found to be important for maintaining an optimal balanced activity on the two receptors GLP-1R and Glucagon receptor. The results shown in the Examples illustrate this aspect.

OXM peptide analogs OXM70 and OXM216 were prepared from OXM29, which includes the native human OXM peptide but with α-aminoisobutyric acid at amino acid position 2 and with a cysteine residue in peptide linkage at the C-terminus and in which the C-terminal carboxy group has been amidated. OXM70 has the structure HαQGTFTSDYSKYLDSRRAQDFVQWLMNTKRNRN NIAC$_4$-CONH$_2$ (SEQ ID NO:12) wherein C$_4$ is cholest-5-en-3-yl{[(2R)-3-amino-2-(amino)-3-oxopropyl]thio}acetate as shown for OXM36. OXM216 has the structure HαQGTFTSDYSKYLDSRRAQDFVQWLMNTKRNRN NIAC$_7$-CONH$_2$ (SEQ ID NO:29) wherein the C$_7$ is a cholest-5-en-3-yl 1-{[(2R)-3-amino-2-(amino)-3-oxopropyl]thio}-2-oxo-6,9,12,15-tetraoxa-3-azaoctadecan-18-oate (or Cys(Oxa4-cholesterol)) as for OXM115.

OXM peptide analog OXM212 was prepared from OXM208, which includes the native human OXM peptide but with α-aminoisobutyric acid at amino acid position 2, norleucine in place of the methionine residue at position 27, with a cysteine residue in peptide linkage at the C-terminus and in which the C-terminal carboxy group has been amidated. OXM212 has the structure HαQGTFTSDYSKYLDSRRAQDFVQWLnNTKRNRNN IAC$_4$-CONH$_2$ (SEQ ID NO:26) wherein C$_4$ is cholest-5-en-3-yl{[(2R)-3-amino-2-(amino)-3-oxopropyl]thio}acetate as shown for OXM36.

OXM peptide analog OXM213 was prepared from OXM209, which includes the native human OXM peptide but with α-aminoisobutyric acid at amino acid position 2, O-methyl-L-homoserine in place of the methionine residue at position 27, with a cysteine residue in peptide linkage at the C-terminus and in which the C-terminal carboxy group has been amidated. OXM213 has the structure HαQGTFTSDYSKYLDSRRAQDFVQWLYNTKRNRNN IAC$_4$-CONH$_2$ (SEQ ID NO:28) wherein C$_4$ is cholest-5-en-3-yl{[(2R)-3-amino-2-(amino)-3-oxopropyl]thio}acetate as shown for OXM36.

OXM237 has the structure HsQGTFTSDYSKYLDSR-RAQDFVQWLmNTKRNRNNIAC$_7$-CONH$_2$ (SEQ ID NO:31). It was designed to contain D-Ser (s) at position 2, Met(O) at position 27, and a Cys(Oxa$_4$-cholesterol) (C$_7$) at position site 38.

OXM238 was designed to contain D-Ser (s) at position 2, Met(O) at position 27, and a Cys(acetamide) (C$_5$) at position site 38. This peptide has the same peptide sequence of OXM237 and is a control peptide with no cholesterol but with the cysteine thiol blocked with acetamide.

OXM259-OXM268 and OXM306-308 (as shown in Table 1) have the amino acid sequence of OXM but wherein the amino acid at position 2 has been substituted with a non-natural amino acid to identify amino acid substitutions that confer resistance to DPP4 catalytic activity.

OXM peptide analogs that lack the amino acid sequence RNRNNIA (SEQ ID NO:55) can also display full agonistic activity on the GLP-1 and the Glucagon receptors. These OXM peptide analogs along with some additional peptides based upon the full-sized OXM peptide are shown in Table 2. These truncated OXM peptide analogs are variants of the Glucagon K (GcgK) genus of peptides that were disclosed in commonly owned International Published Application No. WO2007100535. The GcgK peptides are peptides where the OXM sequence has been truncated at the C terminus to eliminate the seven amino acid residues at the C-terminus. The resulting peptide is that one of glucagon with an extra lysine residue at the C-terminus. This GcgK peptide is compatible with a +/+ pattern in which the peptides show subnanomolar potency on both the GLP-1R and the GCGR. In contrast, native OXM shows nanomolar potency on the two receptors. An additional advantage of the GcgK peptide is that the two basic arginine residues at the C-terminus have been eliminated. This was important in the construction of lipidated (acylated or cholesterylated) peptide analogs having dual GLP-1/GCGR agonist activity. Our data has shown that lipidated peptide analogs with a pI above 7 based on the OXM sequence stimulate mast cell degranulation while lipidated peptide analogs with a pI of about 5 appear not to stimulate mast degranulation (See Example 11). Thus based on our results, to reduce the risk of the peptide stimulating mast cell degranulation, the pI for lipidated based peptide analogs should be around 5. Therefore, in particular aspects the lipidated peptide analogs have a pI less than 6.0. In further aspects, the lipidated peptide analogs have a pI between 4.5 and 6.0. In a further aspect, the lipidated peptide analogs have a pI of about 5.4. Reduction of pI was done using one or more of the following three different strategies: 1) substitution of residues in the peptide, 2) introduction of a carboxylate group at the C terminus, and 3) introduction of negative residues such as one or more gamma-carboxy-glutamic acid residues as spacers.

Therefore, in one aspect of OXM peptide analogs with a pI of less than 6.0, the acyl or cholesterol group is covalently linked to the peptide by means of a spacer that comprises two gamma-carboxy-glutamic acid residues. Examples of these peptide analogs include those peptide analogs shown in Table 2. For example, peptides with a pI of about 5.4 include but are not limited to OXM345, OXM380, OXM381, OXM392, OXM395, OXM398, OXM399, OXM400, and OXM401. In another aspect of peptide analogs with a pI of less than 6.0, the acyl or cholesterol group is covalently linked to an internal amino acid in the peptide analogs by means of a spacer that comprises one or two gamma-carboxy-glutamic acid residues and the peptide further includes one or more gamma-carboxy-glutamic acid residue covalently to the lysine residue at the C-terminus Examples of these peptide analogs include but are not limited to OXM407, OXM408, OXM414, and OXM418. In another aspect of peptide analogs with a pI of less than 6.0, the acyl or cholesterol group is covalently linked to the C-terminus of the peptide by means of a spacer that comprises one gamma-carboxy-glutamic acid residue and the peptide further includes one or more amino acid substitutions to reduce the pI of the peptide. OXM374 is an example of such a peptide analog.

Therefore, further provided is a peptide analog comprising the amino acid sequence HSQGTFTSDYSKYLDSR-RAQDFVQWLMNTK (SEQ ID NO:109) in which the second amino acid from the N-terminus of the peptide is substituted with an amino acid that renders the peptide resistant to cleavage and inactivation by dipeptidyl peptidase IV; the peptide includes a lipid or cholesterol moiety covalently linked to the peptide by a spacer comprising one or more gamma-glutamic acid residues; the peptide optionally includes one to three amino acid substitutions in addition to the substitution at position 2; and the peptide optionally includes a protecting group that, if present, is joined to the C-terminal carboxy group of the peptide; wherein the peptide analog has a pI of less than 6.0 and is a dual GLP-1 receptor agonist and glucagon receptor agonist, and pharmaceutically acceptable salts thereof. In particular aspects, peptide analogs have a pI between 4 and 6, or a pI of about 5.0, for example, a pI of about 5.4.

In further aspects, the amino acid substituted for the second amino acid from the N-terminus of the peptide analog is selected from the group consisting of D-serine, α-aminoisobutyric acid, and 1-amino-1-cyclobutane carboxylic acid.

In particular aspects, the peptide analog includes a cholesterol moiety covalently linked to the thiol group of a cysteine residue that is covalently linked to the ε-amino group of the lysine residue at the C-terminus of the peptide analog by a spacer comprising one or more gamma glutamic acid residues. In a further embodiment, the cholesterol moiety is covalently linked to the thiol group by a hydrophilic linker, which in particular embodiments is an ethoxy polymer that includes one to twelve ethoxy units for example, an ethoxy polymer that includes four ethoxy units.

In particular aspects, the peptide analog includes a lipid moiety covalently linked to the ε-amino group of a lysine residue: in particular embodiments the lipid moiety is a fatty acid such as a palmitoyl, myristoyl, or stearoyl moiety. In a further embodiment, the lipid moiety is covalently linked to the ε-amino group of the lysine residue by one or more gamma-glutamic acid residues. In a further embodiment, the lipid moiety is covalently linked to the ε-amino group of the lysine residue at the C-terminus by one or more gamma-glutamic acid residues. In a further embodiment, the lipid moiety is covalently linked to the ε-amino group of the lysine residue by one or more gamma-glutamic acid residues and the lysine residue linked to the lysine residue at the C-terminus by one or more gamma-glutamic acid residues.

In further aspects, the peptide analog further includes one or more amino acid substitutions at amino acid positions selected from the group consisting of positions 10, 12, 16, 17, 18, and 27. In particular embodiments, the peptide analog includes one or more amino acid substitutions selected from the group consisting of lysine for the tyrosine at position 10, serine for the lysine at position 12, glutamic acid or a-aminoisobutyric acid for the serine at position 16, glutamic acid for the arginine at position 17, alanine for the arginine at position 18, lysine for the glutamine at position 20, and norleucine or O-methyl-L-homoserine for the methionine at position 27.

In a further embodiment, the tyrosine at position 10 in the peptide analog is replaced with a lysine and the lipid moiety is covalently linked to the ε-amino group of the lysine residue by one or more gamma-glutamic acid residues. In another embodiment, the glutamine at position 20 in the peptide analog is replaced with lysine and the lipid moiety is covalently linked to the ε-amino group of the lysine by one or more gamma-glutamic acid residues. In either embodiment, the peptide analog further includes one or more gamma-glutamic acid residues covalently linked to the C-terminus.

Further provided is a peptide analog comprising the structure

wherein P is a peptide having the amino acid sequence

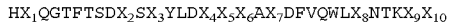

wherein $X_1$ is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe) residue; $X_2$ is a tyrosine (Y) or lysine (K) residue; $X_3$ is serine (S) or lysine (K) residue; $X_4$ is serine (S), α-aminoisobutyric acid (aib), or glutamic acid (E) residue; $X_5$ is an arginine (R) or glutamic acid (E) residue; $X_6$ is an arginine (R) or alanine (A) residue; $X_7$ is a glutamine (Q) or lysine (K) residue; $X_8$ is a methionine (M), norleucine (Nle), methionine sulfoxide (m), or O-methyl-L-homoserine (o) residue; $X_9$ is a gamma glutamic acid (γGlu) residue; $X_{10}$ is a gamma glutamic acid (γGlu) residue or absent; $Z_1$ is an optionally present protecting group that, if present, is joined to the N-terminal amino group, M is (i) a cysteine residue covalently linked to a cholesterol moiety by a hydrophilic linker, (ii) a lysine residue covalently linked to a lipid moiety by a spacer comprising one or more gamma glutamic acid residues, or (iii) a lipid moiety, wherein M is covalently linked to C-terminal or internal amino acid of P by a spacer comprising one or more gamma-glutamic acid residues; and $Z_2$ is an optionally present protecting group that, if present, is joined to the C-terminal carboxy group; and pharmaceutically acceptable salts thereof, wherein the peptide analog or salt thereof has a pI of less than 6.0 and is a dual GLP-1 receptor agonist and glucagon receptor agonist. In particular aspects, peptide analogs have a pI between 4 and 6, or a pI of about 5.0, 5.1, 5.2, 5.3, 5.4, 5.5, 5.6, 5.7, 5.8, or 5.9, or a pI of about 5.4 to 5.5.

In further aspects of the peptide analog, M is a cysteine residue covalently linked to a cholesterol moiety with a hydrophilic linker and the cysteine residue is linked to the C-terminus of P. In further embodiments, the hydrophilic linker is an ethoxy polymer that includes one to twenty-four ethoxy units, which in particular aspects can include for example, four ethoxy units.

In further aspects, M is a lysine residue covalently linked to a lipid moiety by a spacer comprising one or more gamma glutamic acid residues and the lysine residue is linked to the C-terminus of P or M is a lysine residue covalently linked to a lipid moiety by a spacer comprising one or more gamma glutamic acid residues and the lysine residue is at position $X_2$ or $X_7$ of P. In particular aspects, the lipid moiety is a palmitoyl, myristoyl, or stearoyl moiety. Examples of these peptide analogs are shown in Table 2.

TABLE 2

(+/+) OXM Peptide Analogs

| SEQ ID NO. | Name | Structure |
|---|---|---|
| 46 | OXM290 | HsQGTFTSDYSKYLDSEAAQDFVQWLMNTKRNRNNIAC-CONH$_2$ |
| 47 | OXM291 | HsQGTFTSDYSKYLDSRRAQDFVQWLMNTKC-CONH$_2$ |
| 48 | OXM292 | HsQGTFTSDYSKYLDSEAAQDFVQWLMNTKC-CONH$_2$ |
| 49 | OXM293 | HsQGTFTSDYSKYLDSERAQDFVQWLMNTKC-CONH$_2$ |
| 50 | OXM294 | HsQGTFTSDYSKYLDSRAAQDFVQWLMNTKC-CONH$_2$ |
| 51 | OXM301 | HsQGTFTSDYSKYLDSEAAQDFVQWLMNTKRNRNNIAC$_7$-CONH$_2$ |
| 52 | OXM302 | HsQGTFTSDYSKYLDSRRAQDFVQWLMNTKC$_7$-CONH$_2$ |
| 53 | OXM303 | HsQGTFTSDYSKYLDSEAAQDFVQWLMNTKC$_7$-CONH$_2$ |
| 54 | OXM304 | HsQGTFTSDYSKYLDSERAQDFVQWLMNTKC$_7$-CONH$_2$ |
| 55 | OXM305 | HsQGTFTSDYSKYLDSRAAQDFVQWLMNTKC$_7$-CONH$_2$ |
| 56 | OXM311 | HsQGTFTSDYSKYLDSRRAQDFVQWLMNTKK(Palmitoyl)-CONH$_2$ |
| 57 | OXM312 | HsQGTFTSDYSKYLDSEAAQDFVQWLMNTKK(Palmitoyl)-CONH$_2$ |
| 58 | OXM314 | HsQGTFTSDYSKYLDSRRAQDFVQWLMNTK-Ttds-K(Palmitoyl)-CONH$_2$ |
| 59 | OXM313 | HsQGTFTSDYSKYLDSEAAQDFVQWLMNTK-Ttds-K(Palmitoyl)-CONH$_2$ |
| 60 | OXM317 | HsQGTFTSDYSKYLDSRRAQDFVQWLMNTK-γE-C$_4$-CONH$_2$ |
| 61 | OXM318 | HsQGTFTSDYSKYLDSEAAQDFVQWLMNTK-γE-C$_4$-CONH$_2$ |
| 62 | OXM319 | HαQGTFTSDYSKYLDSEAAQDFVQWLMNTKC$_7$-CONH$_2$ |
| 63 | OXM321 | HsQGTFTSDYSKYLDSEAAQDFVQWLMNTKRNRNNIA-γE-C$_4$-CONH$_2$ |
| 64 | OXM323 | HsQGTFTSDYSKYLDSEAAQDFVQWLMNTKR-C$_7$-CONH$_2$ |
| 65 | OXM325 | HsQGTFTSDYSKYLDSEAAQDFVQWLMNTKRNRNNIAC$_7$-COOH |
| 66 | OXM327 | HαQGTFTSDYSKYLDSERAQDFVQWLMNTKC$_7$-CONH$_2$ |
| 67 | OXM329 | HαQGTFTSDYSKYLDSRRAQDFVQWLMNTK-γE-C$_4$-COOH |
| 68 | OXM330 | HsQGTFTSDYSKYLDSEAAQDFVQWLMNTKRNRNNIA-γE-K(Palmitoyl)-CONH$_2$ |
| 69 | OXM345 | HsQGTFTSDYSKYLDSRRAQDFVQWLMNTK-γE-γE-C$_4$-COOH |
| 70 | OXM355 | HsQGTFTSDYSSYLDSRRAQDFVQWLMNTK-γE-C$_4$-COOH |
| 71 | OXM357 | HsQGTFTSDYSKYLDSRAAQDFVQWLMNTK-γE-C$_4$-COOH |
| 72 | OXM359 | HsQGTFTSDYSSYLDSRRAQDFVQWLMNTK-γE-C$_7$-COOH |
| 73 | OXM361 | HsQGTFTSDYSKYLDSRAAQDFVQWLMNTK-γE-C$_7$-COOH |

TABLE 2-continued (+/+) OXM Peptide Analogs

| SEQ ID NO. | Name | Structure |
|---|---|---|
| 74 | OXM373 | HsQGTFTSDYSKYLDERRAQDFVQWLMNTK-γE-C$_4$-COOH |
| 75 | OXM374 | HsQGTFTSDYSKYLDERRAQDFVQWLMNTK-γE-C$_7$-COOH |
| 76 | OXM380 | HsQGTFTSDYSKYLDSRRAQDFVQWLMNTK-γE-γE-C$_7$-COOH |
| 77 | OXM381 | HsQGTFTSDYSKYLDSRRAQDFVQWLMNTK-γE-γE-C$_9$-COOH |
| 78 | OXM383 | HαQGTFTSDYSKYLDSRRAQDFVQWLMNTK-γE-γE-C$_7$-COOH |
| 79 | OXM388 | H-Acb-QGTFTSDYSKYLDSRRAQDFVQWLMNTK-γE-γE-C$_7$-COOH |
| 80 | OXM392 | HsQGTFTSDYSKYLDERRAKDFVQWLMNTK-γE-γE-C$_{10}$-COOH (lactam bridge between E and K) |
| 81 | OXM395 | HαQGTFTSDYSKYLDERRAKDFVQWLMNTK-γE-γE-C$_{10}$-COOH (lactam bridge between E and K) |
| 82 | OXM398 | H-Acb-QGTFTSDYSKYLDERRAKDFVQWLMNTK-γE-γE-C$_{10}$-COOH (lactam bridge between E and K) |
| 83 | OXM399 | HsQGTFTSDYSKYLDSRRAQDFVQWLMNTK-γE-γE-C$_{10}$-COOH |
| 84 | OXM400 | HαQGTFTSDYSKYLDSRRAQDFVQWLMNTK-γE-γE-C$_{10}$-COOH |
| 85 | OXM401 | H-Acb-QGTFTSDYSKYLDSRRAQDFVQWLMNTK-γE-γE-C$_{10}$-COOH |
| 86 | OXM404 | HsQGTFTSDYSKYLDSRRAQDFVQWLMNTK-γE-γE-K(γE-palmitoyl)-CONH$_2$ |
| 87 | OXM406 | HsQGTFTSDYSKYLDERRAQDFVQWLMNTK-γE-γE-C$_{10}$-CONH$_2$ |
| 88 | OXM407 | HsQGTFTSDYSKYLDSRRAK(γE-palmitoyl)DFVQWLMNTK-γEγE-CONH$_2$ |
| 89 | OXM408 | HsQGTFTSDYSKYLDSRRAK(γE-γE-palmitoyl)DFVQWLMNTK-γE-CONH$_2$ |
| 90 | OXM409 | HsQGTFTSDK(γE-γE-palmitoyl)SKYLDSRRAQDFVQWLMNTK-CONH$_2$ |
| 91 | OXM410 | HsQGTFTSDYSKYLDERRAK(γE-γE-palmitoyl)DFVQWLMNTK-CONH$_2$ |
| 92 | OXM411 | HsQGTFTSDK(γE-γE-palmitoyl)SKYLDERRAQDFVQWLMNTK-CONH$_2$ |
| 93 | OXM412 | HsQGTFTSDYSKYLDSRRAQDFVQWLMNTK-γE-γE-C$_{11}$-COOH |
| 94 | OXM413 | HaDGTFTSDYSKYLDSRRAQDFVK(DOTA)WLmNTK-γE-γE-C$_{10}$-CONH$_2$ |
| 95 | OXM414 | HsQGTFTSDK(γE-palmitoyl)SKYLDERRAQDFVQWLMNTK-γE-CONH$_2$ |
| 96 | OXM415 | HsQGTFTSDK(palmitoyl)SKYLDERRAQDFVQWLMNTK-γE-γE-CONH$_2$ |
| 97 | OXM416 | HαQGTFTSDK(γE-palmitoyl)SKYLDERRAQDFVQWLMNTK-γE-CONH$_2$ |
| 98 | OXM417 | H-Acb-QGTFTSDK(γE-γE-palmitoyl)SKYLDERRAQDFVQWLMNTK-CONH$_2$ |
| 99 | OXM418 | HsQGTFTSDK(γE-γE-palmitoyl)SKYLDαRRAQDFVQWLMNTK-γE-CONH$_2$ |
| 100 | OXM419 | HαQGTFTSDYSKYLDSRRAQDFVQWLMNTK-γE-γE-K(γE-palmitoyl)-CONH$_2$ |

TABLE 2-continued

(+/+) OXM Peptide Analogs

| SEQ ID NO. | Name | Structure |
|---|---|---|
| 101 | OXM420 | H-Acb-QGTFTSDYSKYLDSRRAQDFVQWLMNTK-γE-γE-K(γE-palmitoyl)-CONH$_2$ |
| 102 | OXM421 | HsQGTFTSDYSKYLDSRRAQDFVQWLMNTK-γE-γE-C$_{12}$-COOH |

α = α-aminoisobutyric acid (Aib); s = D-Ser; K(Pam) = K(palmitoyl); m = methionine sulfoxide; Acb = 1-Amino-1-cyclobutane carboxylic acid;
C$_1$ = Cys(mPEG)5 kDa;
C$_2$ = Cys(mPEG)20 kDa;
C$_3$ = Cys(mPEG)$_2$40 kDa, each corresponding to a cysteine residue PEGylated via the side-chain thiol with linear methoxyPEG (mPEG) or branched mPEG [(mPEG)2] of the indicated MW;
C$_4$ = Cys(cholest-5-en-3-yl 1{[(2R)-3-amino-2-(amino)-3-oxopropyl]thio}acetate);
C$_5$ = Cys(CH$_2$CONH$_2$), corresponding to a cysteine residue in which the side-chain thiol was reacted with iodoacetamide;
C$_6$ = Cys(mPEG)$_2$60 kDa, each corresponding to a cysteine residue PEGylated via the side-chain thiol with linear methoxyPEG (mPEG) or branched mPEG$_2$mPEG [(mPEG)$_2$] of the indicated MW;
C$_7$= Cys(cholest-5-en-3-yl 1-{[(2R)-3-amino-2-(amino)-3-oxopropyl]thio}-2-oxo-6,9,12,15-tetraoxa-3-azaoctadecan-18-oate]) or Cys(Oxa4-cholesterol)
C$_8$= Cys(N-ethylmaleimidyl).
C$_9$ = S-{1-[46-(cholest-5-en-3-yloxy)-3,43,46-trioxo-7,10,13,16,19,22,25,28,31,34,37,40-dodecaoxa-4,44-diazahexatetracont-1-yl]-2,5-dioxopyrrolidin-3-yl}-L-cysteine or Cys (mal-oxa$_{12}$-cholesterol)
C$_{10}$ = S-[42-(cholest-5-en-3-yloxy)-2,42-dioxo-6,9,12,15,18,21,24,27,30,33,36,39-dodecaoxa-3-azadotetracont-1-yl]-L-cysteine or Cys (oxa$_{12}$-cholesterol)
C$_{11}$ = S-[78-(cholest-5-en-3-yloxy)-2,78-dioxo-6,9,12,15,18,21,24,27,30,33,36,39,42,45,48,51,54,57,60,63,66,69,72,75-tetracosaoxa-3-azaoctaheptacont-1-yl]-L-cysteine or Cys (oxa$_{24}$-cholesterol)
C12 = S-[38-(cholest-5-en-3-yloxy)-2-oxo-6,9,12,15,18,21,24,27,30,33,36-undecaoxa-3-azaoctatriacont-1-yl]-L-cysteine or Cys (oxa$_{12}$-O-cholesterol)
Ttds = 1-amino-4,7,10-trioxa-13-tridecanamine succinimic acid
γE = gamma glutamic acid Peptide OXM290 is the precursor for OXM301 and OXM291 to 294 are precursors for the remainder of the peptide analogs shown in Table 2. OXM301 is an analogue having D-Ser in amino acid position 2 for DPPIV resistance, substitution of Glu and Ala, respectively, for the Arg$_{17}$ and Arg$_{18}$ residues, and a C(Oxa$_4$-cholesterol) group (C$_7$) for improved pharmacokinetic properties in vivo. The substitutions at Arg$_{17}$ and Arg$_{18}$ were made to increase in vivo stability, since these residues are primary proteolytic cleavage sites.

OXM302 is a peptide analog that lacks the amino acid sequence RNRNNIA (SEQ ID NO:96) at the C-terminus (See commonly owned International Published Application No. WO2007/100535, which is incorporated herein in its entirety). Thus, OXM302 is one amino acid longer than the glucagon peptide by one lysine residue at the C-terminus. In OXM302, which has the structure HsQGTFTSDYSKYLD-SRRAQDFVQWLMNTKC$_7$-CONH$_2$ (SEQ ID NO:52) there is a D-Ser in amino acid position 2 for DPPIV resistance and a C(Oxa4-cholesterol) group (C$_7$) for improved pharmacokinetic properties in vivo.

OXM303 has the structure HsQGTFTSDYSKYLD-SEAAQDFVQWLMNTKC$_7$-CONH$_2$ (SEQ ID NO:53). The D-Ser in amino acid position 2 provides DPPIV resistance, substitution of Glu and Ala, respectively, for the Arg$_{17}$ and Arg$_{18}$ residues improves stability and a C(Oxa4-cholesterol) group (C$_7$) improves the peptide analog's pharmacokinetic properties in vivo.

OXM304 has the structure HsQGTFTSDYSKYLDSER-AQDFVQWLMNTKC$_7$-CONH$_2$ (SEQ ID NO:54). The D-Ser in position 2 provides DPPIV resistance, substitution of Glu for the Arg$_{17}$ residue improves stability and a C(Oxa4-cholesterol) group (C$_7$) improves the peptide analog's pharmacokinetic properties in vivo.

OXM305 has the structure HsQGTFTSDYSKYLDSER-AQDFVQWLMNTKC$_7$-CONH$_2$ (SEQ ID NO:55). The D-Ser in position 2 provides DPPIV resistance, substitution of Ala for the Arg$_{18}$ residue improves stability and a C(Oxa4-cholesterol) group (C$_7$) improves the peptide analog's pharmacokinetic properties in vivo.

OXM311 has the structure HsQGTFTSDYSKYLDSR-RAQDFVQWLMNTK-K(Palmitoyl)-CONH$_2$ (SEQ ID NO:56). The D-Ser in amino acid position 2 provides DPPIV resistance and the K(palmitoyl) group improves the peptide analog's pharmacokinetic properties in vivo.

OXM312 has the structure HsQGTFTSDYSKYLD-SEAAQDFVQWLMNTKK(Palmitoyl)-CONH$_2$ (SEQ ID NO:57). The D-Ser in amino acid position 2 provides DPPIV resistance, substitution of Glu and Ala, respectively, for the Arg$_{17}$ and Arg$_{18}$ residues improves stability and the K(palmitoyl) group improves the peptide analog's pharmacokinetic properties in vivo.

OXM314 has the structure HsQGTFTSDYSKYLDSR-RAQDFVQWLMNTK-Ttds-K(Palmitoyl)-CONH$_2$ (SEQ ID NO:58). The D-Ser in amino acid position 2 provides DPPIV resistance and the K(palmitoyl) group improves the peptide analog's pharmacokinetic properties in vivo. The Ttds (1-amino-4,7,10-trioxa-13-tridecanamine succinimic acid) is a linker that acts as a flexible and hydrophilic spacer between the peptide sequence and the K(palmitoyl) group.

OXM313 has the structure HsQGTFTSDYSKYLD-SEAAQDFVQWLMNTK-Ttds-K(Palmitoyl)-CONH$_2$ (SEQ ID NO:59). The D-Ser in amino acid position 2 provides DPPIV resistance, substitution of Glu and Ala, respectively, for the Arg$_{17}$ and Arg$_{18}$ residues improves stability and the Ttds-K(palmitoyl) group improves the peptide analog's pharmacokinetic properties in vivo.

OXM317 has the structure HsQGTFTSDYSKYLDSR-RAQDFVQWLMNTK-γE-C$_4$-CONH$_2$ (SEQ ID NO:60). In the peptide, there is a D-Ser in amino acid position 2 for DPPIV resistance, and a gamma glutamic residue linked to cholest-5-en-3-yl{[(2R)-3-amino-2-(amino)-3-oxopropyl]

thio}acetate (C₄) for improves pharmacokinetic properties in vivo. The gamma glutamic residue (γE) is a linker that acts as a flexible spacer between the peptide sequence and the C₄ group.

OXM318 has the structure HsQGTFTSDYSKYLD-SEAAQDFVQWLMNTK-γE-C₄-CONH₂ (SEQ ID NO:61). The D-Ser in amino acid position 2 provides DPPIV resistance, substitution of Glu and Ala, respectively, for the Arg₁₇ and Arg₁₈ residues improves stability and the γE-C₄ group improves the peptide analog's pharmacokinetic properties in vivo.

OXM319 has the structure HaQGTFTSDYSKYLD-SEAAQDFVQWLMNTKC₇-CONH₂ (SEQ ID NO:62). In the peptide, there is a Aib in amino acid position 2 for DPPIV resistance, and the C(Oxa₄-cholesterol) group (C₇) improves the peptide analog's pharmacokinetic properties in vivo.

OXM321 has the structure HsQGTFTSDYSKYLD-SEAAQDFVQWLMNTKRNRNNIA-γE-C₄-CONH₂ (SEQ ID NO:63). It is an analogue having D-Ser in amino acid position 2 for DPPIV resistance, substitution of Glu and Ala, respectively, for the Arg₁₇ and Arg₁₈ residues and a C(-cholesterol) group (C₄) improves pharmacokinetic properties in vivo. The substitutions at Arg₁₇ and Arg₁₈ were made to increase in vivo stability, since these residues are primary proteolytic cleavage sites. The gamma glutamic residue (γE) is a linker that acts as a flexible spacer between the peptide sequence and the C₄ group.

OXM323 has the structure HsQGTFTSDYSKYLD-SEAAQDFVQWLMNTKR-C₇-CONH₂ (SEQ ID NO:64). The D-Ser in position 2 provides DPPIV resistance, substitution of Glu and Ala for Arg₁₇ and Arg₁₈ residue provides a peptide with improved stability and the C(Oxa₄-cholesterol) group (C₇) provides a peptide with improved pharmacokinetic properties in vivo.

OXM325 has the structure HsQGTFTSDYSKYLD-SEAAQDFVQWLMNTKRNRNNIAC₇-CO₂H (SEQ ID NO:65). It is an analogue having D-Ser in amino acid position 2 for DPPIV resistance, substitution of Glu and Ala, respectively, for the Arg₁₇ and Arg₁₈ residues, and a C(Oxa₄-cholesterol) group (C₇) improves pharmacokinetic properties in vivo. The substitutions at Arg₁₇ and Arg₁₈ were made to increase in vivo stability, since these residues are primary proteolytic cleavage sites.

OXM327 has the structure HαQGTFTSDYSKYLDSERAQDFVQWLMNTKC₇-CONH₂ (SEQ ID NO:66). The Aib in position 2 provides DPPIV resistance, substitution of Glu for the Arg₁₇ residue provides a peptide with improved stability and the C(Oxa₄-cholesterol) group (C₇) provides improved pharmacokinetic properties in vivo.

OXM329 has the structure HαQGTFTSDYSKYLDSRRAQDFVQWLMNTK-γE-C₄-CO₂H (SEQ ID NO:67). The Aib in position 2 provides DPPIV resistance and a C(Oxa4-cholesterol) group (C₇) provides a peptide with improved pharmacokinetic properties in vivo. The gamma glutamic residue (γE) is a linker that acts as a flexible spacer between the peptide sequence and the C₄ group.

OXM330 has the structure HsQGTFTSDYSKYLD-SEAAQDFVQWLMNTKRNRNNIA-γE-K(Pam)-CONH₂ (SEQ ID NO:68). It is an analogue having D-Ser in amino acid position 2 for DPPIV resistance, substitution of Glu and Ala, respectively, for the Arg₁₇ and Arg₁₈ residues and a -K(palmitoyl) group improves the peptide analog's pharmacokinetic properties in vivo. The gamma glutamic residue (γE) is a linker that acts as a flexible spacer between the peptide sequence and the K(palmitoyl) group. The substitutions at Arg₁₇ and Arg₁₈ were made to increase in vivo stability, since these residues are primary proteolytic cleavage sites.

OXM345 has the structure HsQGTFTSDYSKYLDSR-RAQDFVQWLMNTK-γE-γE-C₄-COOH (SEQ ID NO:69). It was designed to contain D-Ser (s) at position 2, two gamma-glutamic acid at positions 31 and 32 as spacers between the peptide sequence, and the cholesterol group, one Cys(cholesterol) at position 33 (C₄).

OXM355 has the structure HsQGTFTSDYSSYLDSR-RAQDFVQWLMNTK-γE-C₄-COOH (SEQ ID NO:70). It was designed to contain D-Ser (s) at position 2, a Lys₁₂Ser substitution, one gamma-glutamic acid at position 31 as spacer between the peptide sequence, and the cholesterol one Cys(cholesterol) at position 32 (C₄). A serine in position 12 is present in the GLP-1 peptide sequence. Therefore, it is expected to have at least compatible potency at the GLP-1R. The substitution Lys₁₂Ser eliminates a positive charge which results in a pI of about 5.

OXM357 has the structure HsQGTFTSDYSKYLD-SRAAQDFVQWLMNTK-γE-C₄-COOH (SEQ ID NO:71). It was designed to contain D-Ser (s) at position 2, one gamma-glutamic acid at position 31 as spacer between the peptide sequence, and the cholesterol one Cys(cholesterol) (C₄) at position 32. OXM357 differs from OXM345 in having only one γ-Glu while OXM345 has two γ-Glu.

OXM359 has the structure HsQGTFTSDYSSYLDSR-RAQDFVQWLMNTK-γE-C₇-COOH (SEQ ID NO:72). It was designed to contain D-Ser (s) at position 2, a Lys₁₂Ser substitution, one gamma-glutamic acid at position 31 as spacer between the peptide sequence, and the cholesterol, one Cys(Oxa₄-cholesterol) at position 32 (C₇). Thus, OXM359 differs from OXM355 in having C₇ (cholesterol group with the tetraethylene glycol spacer) instead of C₄ (cholesterol without an ethylene glycol spacer).

OXM361 has the structure HsQGTFTSDYSKYLD-SRAAQDFVQWLMNTK-γE-C₇-COOH (SEQ ID NO:73). It was designed to contain D-Ser (s) at position 2, an Arg₁₈Ala substitution, one gamma-glutamic acid at position 31 as spacer between the peptide sequence, and the cholesterol, one Cys(Oxa₄-cholesterol) at position 32 (C₇ in the table). The Arg₁₈Ala substitution eliminates a positive charge which is important for the tuning of the optimal pI value to 5.

OXM373 has the structure HsQGTFTSDYSKYLDER-RAQDFVQWLMNTK-γE-C₄-COOH (SEQ ID NO:74). It was designed to contain D-Ser (s) at position 2, a Ser₁₆Glu substitution, one gamma-glutamic acid at position 31 as spacers between the peptide sequence, and the cholesterol, one Cys(cholesterol) at position 32 (C₄). The Glu at position 16 is present in the exendin-4 peptide so this substitution is expected to be at least compatible with GLP-1R activation.

OXM374 has the structure HsQGTFTSDYSKYLDER-RAQDFVQWLMNTK-γE-C₇-COOH (SEQ ID NO:75). It was designed to contain D-Ser (s) at position 2, a Ser₁₆Glu substitution, one gamma-glutamic acid at position 31 as spacer between the peptide sequence, and the cholesterol, one Cys(Oxa₄-cholesterol) at position 32 (C₇). Thus, the difference between OXM373 and 374 is due to the presence of the tetraethylene glycol spacer attached to the cholesterol group in OXM374.

OXM380 has the structure HsQGTFTSDYSKYLDSR-RAQDFVQWLMNTK-γE-γE-C₇-COOH (SEQ ID NO:76). It was designed to contain D-Ser (s) at position 2, two gamma-glutamic acid at positions 31 and 32 as spacer between the peptide sequence, and the cholesterol, one Cys(Oxa$_4$-cholesterol) (C$_7$) at position 33. OXM380 has the same peptide sequence of OXM345 but differs in the Oxa$_4$ spacer linked to the cholesterol group.

OXM381 has the structure HsQGTFTSDYSKYLDSR-RAQDFVQWLMNTK-γE-γE-C$_9$-COOH (SEQ ID NO:77). It was designed to contain D-Ser (s) at position 2, two gamma-glutamic acid at positions 31 and 32 as spacer between the peptide sequence, and the cholesterol, one Cys(maleimide-Oxa$_{12}$-cholesterol) (C$_9$) at position 33. OXM381 has the same peptide sequence of OXM345 and OXM380 differing in the maleimide-Oxa$_{12}$ spacer linked to the cholesterol. The structure of C$_9$ is shown below.

Cys(Oxa$_4$-cholesterol) (C$_7$) at position 33. OXM388 differs from OXM380 and 383 only with respect to the amino acid at position 2.

OXM392 has the structure HsQGTFTSDYSKYLD<u>E</u>RRA<u>K</u>DFVQWLMNTK-γE-γE-C$_{10}$-COOH (lactam bridge between <u>E</u> and <u>K</u>) (SEQ ID NO:80). It was designed to contain Ser (s) at position 2, Ser$_{16}$Glu and Gln$_{20}$Lys substitutions wherein the Glu$_{16}$ and Lys$_{20}$ are linked with a lactam bridge on the side chains, two gamma-glutamic acid

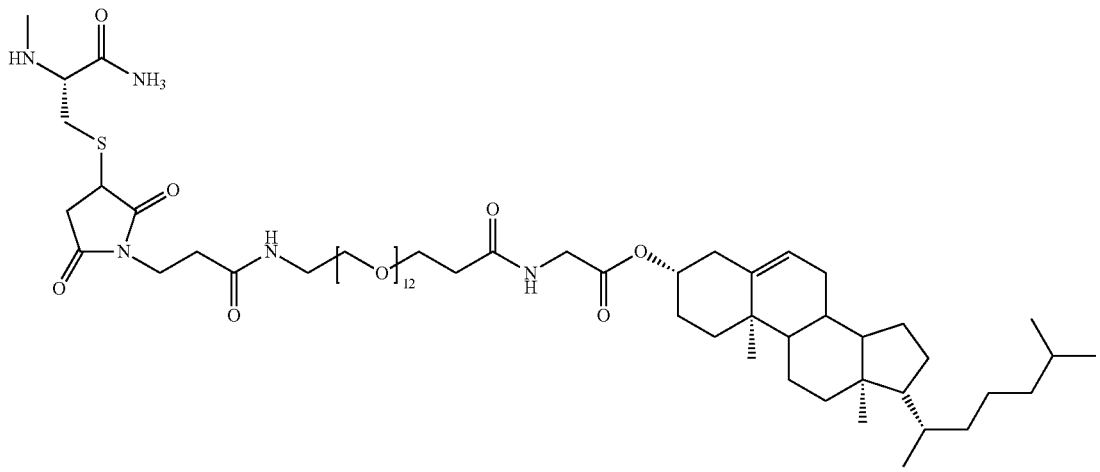

OXM383 has the structure HαQGTFTSDYSKYLDSRRAQDFVQWLMNTK-γE-γE-C$_7$-COOH (SEQ ID NO:78). It was designed to contain Aib (α) at position 2, two gamma-glutamic acid at positions 31 and 32 as spacer between the peptide sequence, and the cholesterol, one Cys(Oxa$_4$-cholesterol) (C$_7$) at position 33. OXM383 differs from OXM380 only with respect to the amino acid at position 2.

OXM388 has the structure H-Acb-QGTFTSDYSKYLD-SRRAQDFVQWLMNTK-γE-γE-C$_7$-COOH (SEQ ID NO:79). It was designed to contain Acb at position 2, two gamma-glutamic acid at positions 31 and 32 as spacer between the peptide sequence, and the cholesterol, one at positions 31 and 32 as spacer between the peptide sequence, and the cholesterol, one Cys(Oxa$_{12}$-cholesterol) (C$_{10}$) at position 33. The lactam bridge is between position i (16) and i+4 (20) and is meant to stabilize the alpha-helical conformation of the peptide and to stabilize the peptide against proteolytic degradation.

The C$_{10}$ group differs from the C$_9$ group for the thioether bond connecting the cysteine thiol group to the Oxa$_{12}$-cholesterol. In C$_9$ there is a maleimide thioether bond while in C$_{10}$ there is an acetamide thioether. The structure of C$_{10}$ is shown below.

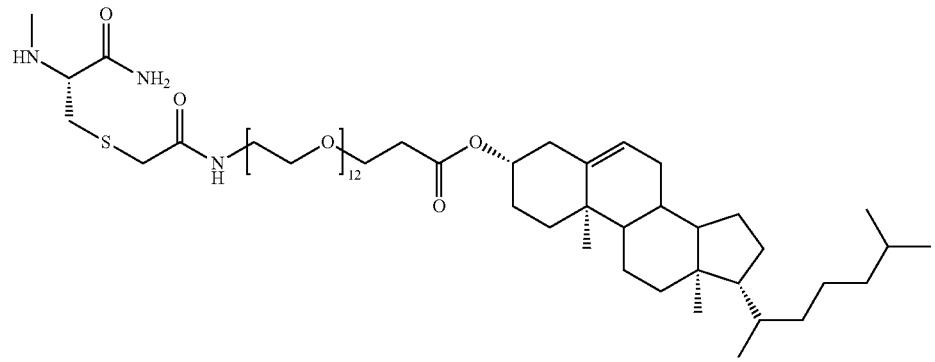

OXM395 has the structure HαQGTFTSDYSKYLD ERRA<u>K</u>DFVQWLMNTK-γE-γE-C$_{10}$-COOH (lactam bridge between <u>E</u> and <u>K</u>) (SEQ ID NO:81). It was designed to contain Aib (α) at position 2, Ser$_{16}$Glu and a Gln$_{20}$Lys substitutions wherein the Glu$_{16}$ and Lys$_{20}$ are linked with a lactam bridge between the side chains, two gamma-glutamic acid residues at positions 31 and 32 as spacer between the peptide sequence, and the cholesterol, one Cys(Oxa$_{12}$-cholesterol) (C$_{10}$) at position 33. The lactam bridge is between position 16(i) and 20 (i+4) and is meant to stabilize the peptide's alpha-helical conformation and to stabilize the peptide against proteolytic degradation.

OXM398 has the structure H-Acb-QGTFTSDYSKYLD ERRA<u>K</u>DFVQWLMNTK-γE-γE-C$_{10}$-COOH (lactam bridge between <u>E</u> and <u>K</u>) (SEQ ID NO:82). It was designed to contain Acb at position 2, Ser$_{16}$Glu and a Gln$_{20}$Lys substitutions wherein the Glu$_{16}$ and Lys$_{20}$ are linked with a lactam bridge between the side chains, two gamma-glutamic acid residues at positions 31 and 32 as spacer between the peptide sequence, and the cholesterol, one Cys(Oxa$_{12}$-cholesterol) (C$_{10}$) at position 33. The lactam bridge is between position 16 (i) and 20 (i+4) and is meant to stabilize the alpha-helical conformation of the peptide and to stabilize the peptide against proteolytic degradation.

OXM392, 395 and 398 differ only in the amino acid that is at position 2.

OXM399 has the structure HsQGTFTSDYSKYLDSR-RAQDFVQWLMNTK-γE-γE-C$_{10}$-COOH (SEQ ID NO:83). It was designed to contain D-Ser (s) at position 2, two gamma-glutamic acid residues at positions 31 and 32 as spacer between the peptide sequence, and the cholesterol, one Cys(Oxa$_{12}$-cholesterol) (C$_{10}$) at position 33. OXM399 differs from OXM392 only in that it lacks the lactam bridge present in OXM392.

OXM400 has the structure HαQGTFTSDYSKYLDSRRAQDFVQWLMNTK-γE-γE-C$_{10}$-COOH (SEQ ID NO:84). It was designed to contain Aib (α) at position 2, two gamma-glutamic acid residues at positions 31 and 32 as spacer between the peptide sequence, and the cholesterol, one Cys(Oxa$_{12}$-cholesterol) (C$_{10}$) at position 33. OXM400 differs from OXM395 only in that it lacks the lactam bridge present in OXM395.

OXM401 has the structure H-Acb-QGTFTSDYSKYLD-SRRAQDFVQWLMNTK-γE-γE-C$_{10}$-COOH (SEQ ID NO:85). It was designed to contain Acb at position 2, two gamma-glutamic acid at positions 31 and 32 as spacer between the peptide sequence, and the cholesterol, one Cys(Oxa$_{12}$-cholesterol) (C$_{10}$) at position 33. OXM401 differs from OXM398 only in that it lacks the lactam bridge present in OXM398. OXM399, OXM40, and 401 differ from each other in the amino acid at position 2.

OXM404 has the structure HsQGTFTSDYSKYLDSR-RAQDFVQWLMNTK-γE-γE-K(γE-palmitoyl)-CONH$_2$ (SEQ ID NO:86). It was designed to contain D-Ser (s) at position 2, two gamma-glutamic acid at positions 31 and 32 as spacer between the peptide sequence, and the palmitoyl group, one Lys(γE-palmitoyl) at position 33. The peptide in this embodiment is amidated at the C-terminus.

OXM406 has the structure HsQGTFTSDYSKYLDER-RAQDFVQWLMNTK-γE-γE-C$_{10}$-CONH$_2$ (SEQ ID NO:87). It was designed to contain D-Ser (s) at position 2, a Ser$_{16}$Glu substitution, two gamma-glutamic acid residues at positions 31 and 32 as spacer between the peptide sequence, and the cholesterol, one Cys(Oxa$_{12}$-cholesterol) (C$_{10}$) at position 33. The peptide in this embodiment is amidated at the C-terminus.

OXM407 has the structure HsQGTFTSDYSKYLDSR-RAK(γE-palmitoyl)DFVQWLMNTK-γE-γE-CONH$_2$ (SEQ ID NO:88). It was designed to contain D-Ser (s) at position 2, two gamma-glutamic acid residues at positions 31 and 32 as spacer between the peptide sequence, and the palmitoyl group, one Lys(γE-palmitoyl) at position 33. The peptide in this embodiment is amidated at the C-terminus.

OXM408 has the structure HsQGTFTSDYSKYLDSR-RAK(γE-γE-palmitoyl)DFVQWLMNTK-γE-CONH$_2$ (SEQ ID NO:89). It was designed to contain D-Ser (s) at position 2, one gamma-glutamic acid at positions 31, and a palmitoyl group linked to two γ-glutamic acid residues and to the side chain amino group of a lysine [Lys(γE-γE-palmitoyl)] at position 20. The peptide in this embodiment is amidated at the C-terminus.

OXM409 has the structure HsQGTFTSDK(γE-γE-palmitoyl)SKYLDSRRADFVQWLMNTK-CONH$_2$ (SEQ ID NO:89). It was designed to contain D-Ser (s) at position 2 and a palmitoyl group linked to two γ-glutamic acid residues and to the side chain amino group of a lysine [Lys(γE-γE-palmitoyl)] at position 10. The peptide in this embodiment is amidated at the C-terminus.

OXM410 has the structure HsQGTFTSDYSKYLDER-RAK(γE-γE-palmitoyl)DFVQWLMNTK-CONH$_2$ (SEQ ID NO:91). It was designed to contain D-Ser (s) at position 2, a Ser$_{16}$Glu substitution, and a palmitoyl group linked to two 7-glutamic acid residues and to the side chain amino group of a lysine [Lys(γE-γE-palmitoyl)] at position 20. The peptide in this embodiment is amidated at the C-terminus.

OXM411 has the structure HsQGTFTSDK(γE-γE-palmitoyl)SKYLDERRAQDFVQWLMNTK-CONH$_2$ (SEQ ID NO:92). It was designed to contain D-Ser (s) at position 2, a Ser$_{16}$Glu substitution and a palmitoyl group linked to two γ-glutamic acid residues and to the side chain amino group of a lysine [Lys(γE-γE-palmitoyl)] at position 10. The peptide in this embodiment is amidated at the C-terminus.

OXM412 has the structure HsQGTFTSDYSKYLDSR-RAQDFVQWLMNTK-γE-γE-C$_{11}$-COOH (SEQ ID NO:93). It was designed to contain D-Ser (s) at position 2, two gamma-glutamic acid residues at positions 31 and 32 as spacer between the peptide sequence, and the cholesterol, one Cys(Oxa$_{24}$-cholesterol) (C$_{11}$) at position 33. OXM412 differs from OXM399 for the length of the Oxa spacer linked to the cholesterol group. The structure of C$_{11}$ is shown below.

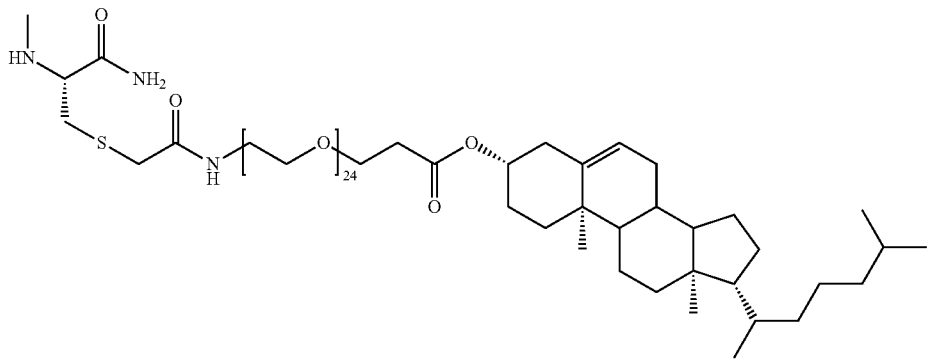

OXM413 has the structure HαDGTFTSDYSKYLDSRRAQDFVK(DOTA)WLmNTK-γE-γE-C$_{10}$-CONH$_2$ (SEQ ID NO:94). It was designed as a peptide for imaging to target GLP-1R in vivo. The sequence contains Aib at position 2, an Asp at position 3 to give selectivity on the GLP-1R, a Lys(DOTA) at position 24, a Met(O) at position 27, two gamma-glutamic acid residues at positions 31 and 32 as spacer between the peptide sequence, and the cholesterol, one Cys(Oxa$_{12}$-cholesterol) (C$_{10}$) at position 33. The peptide in this embodiment is amidated at the C-terminus. The structure of Fmoc-Lys(DOTA)-OH is shown below.

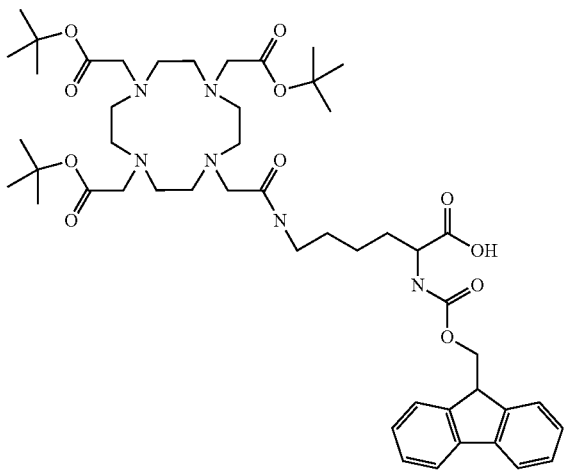 [SMILES: CC(C)(C)OC(=O)CN1CCN(CC(=O)NCCCCC(NC(=O)OCC2c3ccccc3-c3ccccc32)C(=O)O)CCN(CC(=O)OC(C)(C)C)CCN(CC(=O)OC(C)(C)C)CC1]

OXM414 has the structure HsQGTFTSDK(γE-palmitoyl)SKYLDERRAQDFVQWLMNTK-γE-CONH$_2$ (SEQ ID NO:95). It was designed to contain D-Ser (s) at position 2, two γ-glutamic acids at positions 31, a Ser$_{16}$Glu substitution and a palmitoyl group linked to the side chain amino group of a lysine [Lys(palmitoyl)] at position 10. The peptide in this embodiment is amidated at the C-terminus.

OXM415 has the structure HsQGTFTSDK(palmitoyl)SKYLDERRAQDFVQWLMNTK-γE-γE-CONH$_2$ (SEQ ID NO:96). It was designed to contain D-Ser (s) at position 2, one γ-glutamic acid at positions 31, a Ser$_{16}$Glu substitution and a palmitoyl group linked to one γ-glutamic acid residue and to the side chain amino group of a lysine [Lys(γE-palmitoyl)] at position 10. The peptide in this embodiment is amidated at the C-terminus.

OXM416 has the structure HαQGTFTSDK(γE-γE-palmitoyl)SKYLDERRAQDFVQWLMNTK-CONH$_2$ (SEQ ID NO:97). It was designed to contain Aib (α) at position 2, a Ser$_{16}$Glu substitution and a palmitoyl group linked to two γ-glutamic acid residues and to the side chain amino group of a lysine [Lys(γE-γE-palmitoyl)] at position 10. The peptide in this embodiment is amidated at the C-terminus.

OXM417 has the structure H-Acb-QGTFTSDK(γE-γE-palmitoyl)SKYLDERRAQDFVQWLMNTK-CONH$_2$ (SEQ ID NO:98). It was designed to contain Acb at position 2, a Ser$_{16}$Glu substitution and a palmitoyl group linked to two γ-glutamic acid residues and to the side chain amino group of a lysine [Lys(γE-γE-palmitoyl)] at position 10. The peptide in this embodiment is amidated at the C-terminus.

OXM418 has the structure HsQGTFTSDK(γE-γE-palmitoyl)SKYLDαRRAQDFVQWLMNTK-γE-CONH$_2$ (SEQ ID NO:99). It was designed to contain D-Ser (s) at position 2, one gamma-glutamic acid at positions 31, a Ser$_{16}$Aib (α) substitution and a palmitoyl group linked to two γ-glutamic acid residues and to the side chain amino group of a lysine [Lys(γE-γE-palmitoyl)] at position 10. The peptide in this embodiment is amidated at the C-terminus.

OXM419 has the structure HαQGTFTSDYSKYLDSRRAQDFVQWLMNTK-γE-γE-K(γE-palmitoyl)-CONH$_2$ (SEQ ID NO:100). It was designed to contain Aib (α) at position 2, two gamma-glutamic acid at positions 31 and 32 as spacer between the peptide sequence, and the palmitoyl group, one Lys(γE-palmitoyl) at position 33. The peptide in this embodiment is amidated at the C-terminus.

OXM420 has the structure H-Acb-QGTFTSDYSKYLDSRRAQDFVQWLMNTK-γE-γE-K(γE-palmitoyl)-CONH$_2$ (SEQ ID NO:101). It was designed to contain Acb at position 2, two gamma-glutamic acid at positions 31 and 32 as spacer between the peptide sequence, and the palmitoyl group, one Lys(γE-palmitoyl) at position 33. The peptide in this embodiment is amidated at the C-terminus.

OXM421 has the structure HsQGTFTSDYSKYLDSRRAQDFVQWLMNTK-γE-γE-C$_{12}$-COOH (SEQ ID NO:102). It was designed to contain D-Ser (s) at position 2, two gamma-glutamic acid residues at positions 31 and 32 as spacer between the peptide sequence, and the cholesterol, one Cys(Oxa$_{12}$-O-cholesterol) (C$_{12}$) at position 33. The Cys(Oxa$_{12}$-O-cholesterol) differs from Cys(Oxa$_{12}$-cholesterol) in having the cholesterol linked through an ether bond to the Oxa$_{12}$ spacer. The ether bond can confer more stability towards the ester bond present in the Cys(Oxa$_{12}$-cholesterol) or C$_{11}$ group. The structure of Cys(oxa$_{12}$-O-cholesterol) is shown below.

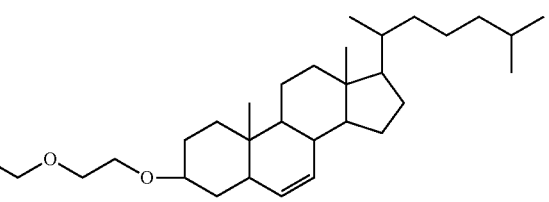
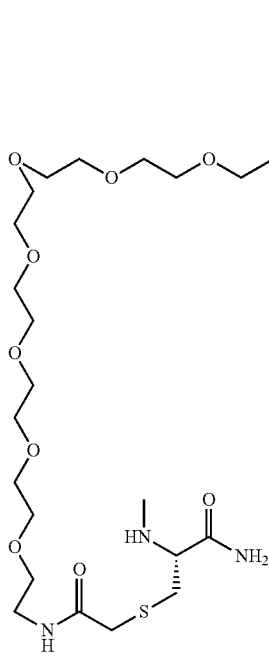

Pharmaceutical Compositions

Further provided are pharmaceutical compositions comprising a therapeutically effective amount of one or more of the OXM analogs disclosed herein for the treatment of a metabolic disorder in an individual. Such disorders include, but are not limited to, obesity, metabolic syndrome or syndrome X, type II diabetes, complications of diabetes such as retinopathy, hypertension, dyslipidemias, cardiovascular disease, gallstones, osteoarthritis, and certain forms of cancers. The obesity-related disorders herein are associated with, caused by, or result from obesity.

"Obesity" is a condition in which there is an excess of body fat. The operational definition of obesity is based on the Body Mass Index (BMI), calculated as body weight per height in meters squared (kg/m2). "Obesity" refers to a condition whereby an otherwise healthy subject has a Body Mass Index (BMI) greater than or equal to 30 kg/m2, or a condition whereby a subject with at least one co-morbidity has a BMI greater than or equal to 27 kg/m2. An "obese subject" is an otherwise healthy subject with a Body Mass Index (BMI) greater than or equal to 30 kg/m2 or a subject with at least one co-morbidity with a BMI greater than or equal to 27 kg/m2. A "subject at risk for obesity" is an otherwise healthy subject with a BMI of 25 kg/m2 to less than 30 kg/m2 or a subject with at least one co-morbidity with a BMI of 25 kg/m2 to less than 27 kg/m2.

The increased risks associated with obesity occur at a lower Body Mass Index (BMI) in Asians. In Asian countries, including Japan, "obesity" refers to a condition whereby a subject with at least one obesity-induced or obesity-related co-morbidity that requires weight reduction or that would be improved by weight reduction, has a BMI greater than or equal to 25 kg/m2. In Asian countries, including Japan, an "obese subject" refers to a subject with at least one obesity-induced or obesity-related co-morbidity that requires weight reduction or that would be improved by weight reduction, with a BMI greater than or equal to 25 kg/m2. In Asian countries, a "subject at risk of obesity" is a subject with a BMI of greater than 23 kg/m2 to less than 25 kg/m2.

As used herein, the term "obesity" is meant to encompass all of the above definitions of obesity.

Obesity-induced or obesity-related co-morbidities include, but are not limited to, diabetes, non-insulin dependent diabetes mellitus—type 2, impaired glucose tolerance, impaired fasting glucose, insulin resistance syndrome, dyslipidemia, hypertension, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

"Treatment" (of obesity and obesity-related disorders) refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

"Prevention" (of obesity and obesity-related disorders) refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "diabetes," as used herein, includes both insulin-dependent diabetes mellitus (IDDM, also known as type I diabetes) and non-insulin-dependent diabetes mellitus (NIDDM, also known as Type II diabetes). Type I diabetes, or insulin-dependent diabetes, is the result of an absolute deficiency of insulin, the hormone which regulates glucose utilization. Type II diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type II diabetics are also obese. The compounds of the present invention are useful for treating both Type I and Type II diabetes. The compounds are especially effective for treating Type II diabetes. The compounds of the present invention are also useful for treating and/or preventing gestational diabetes mellitus.

U.S. Pat. No. 6,852,690, which is incorporated herein in its entirety, discloses methods for enhancing metabolism of nutrients comprising administering to a non-diabetic patient a formulation comprising a nutritively effective amount of one or more nutrients or any combination thereof and one or more insulinotropic peptides. The OXM peptide analogs disclosed herein are insulinotropic and can be administered to patients with a disturbed glucose metabolism such as insulin resistance but no overt diabetes, as well as patients who for any reason cannot receive nutrition through the alimentary canal. Such patients include surgery patients, comatose patients, patients in shock, patients with gastrointestinal disease, patients with digestive hormone disease, and the like. In particular, obese patients, atherosclerotic patients, vascular disease patients, patients with gestational diabetes, patients with liver disease such as liver cirrhosis, patients with acromegaly, patients with glucorticoid excess such as cortisol treatment or Cushings disease, patients with activated counterregulatory hormones such as would occur after trauma, accidents and surgery and the like, patients with hypertriglyceridemia and patients with chronic pancreatitis can be readily and suitably nourished according to the invention without subjecting the patient to hypo- or hyperglycemia. In particular, the administration to such a patient aims to provide a therapy to as rapidly as possible deliver the nutritional and caloric requirements to the patient while maintaining his plasma glucose below the so-called renal threshold of about 160 to 180 milligrams per deciliter of glucose in the blood. Although normal patients not having glucose levels just below the renal threshold can also be treated according to the invention as described above, patients with disturbed glucose metabolism such as hyperglycemic patients whose plasma glucose level is just above the renal threshold also find the therapy suitable for their condition. In particular, such patients who have a degree of hyperglycemia below the renal threshold at intermittent intervals can receive a combination treatment of nutrients plus insulinotropic peptides according to any of the following regimens. Normal patients not suffering from such hyperglycemia can also be treated using the peptide analogs disclosed herein.

The OXM analogs disclosed herein may be used in a pharmaceutical composition when combined with a pharmaceutically acceptable carrier. Such compositions comprise a therapeutically-effective amount of one or more of the OXM analogs disclosed herein and a pharmaceutically acceptable carrier. Such a composition may also be comprised of (in addition to the OXM analog disclosed herein and a carrier) diluents, fillers, salts, buffers, stabilizers, solubilizers, and other materials well known in the art. Compositions comprising the OXM analogs disclosed herein can be administered, if desired, in the form of salts provided the salts are pharmaceutically acceptable. Salts may be prepared using standard procedures known to those skilled in the art of synthetic organic chemistry.

The term "individual" is meant to include humans and companion or domesticated animals such as dogs, cats, horses, and the like. Therefore, the compositions comprising formula I are also useful for treating or preventing obesity and obesity-related disorders in cats and dogs. As such, the term "mammal" includes companion animals such as cats and dogs.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. It will be understood that, as used herein, references to the OXM analogs disclosed herein are meant to also include the pharmaceutically acceptable salts.

As utilized herein, the term "pharmaceutically acceptable" means a non-toxic material that does not interfere with the effectiveness of the biological activity of the active ingredient(s), approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils. The characteristics of the carrier will depend on the route of administration. The OXM analogs disclosed herein may be in multimers (for example, heterodimers or homodimers) or complexes with itself or other peptides. As a result, pharmaceutical compositions of the invention may comprise one ore more OXM analogs disclosed herein in such multimeric or complexed form.

As used herein, the term "therapeutically effective amount" means the total amount of each active component of the pharmaceutical composition or method that is sufficient to show a meaningful patient benefit, i.e., treatment, healing, prevention or amelioration of the relevant medical condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially, or simultaneously.

The pharmacological composition can comprise one or more OXM analogs disclosed herein; one or more OXM analogs disclosed herein and one or more other agents for treating a metabolic disorder; or the pharmacological composition comprising the one or more OXM analogs disclosed herein can be used concurrently with a pharmacological composition comprising an agent for treating a metabolic disorder. Such disorders include, but are not limited to, obesity, metabolic syndrome or syndrome X, type II diabetes, complications of diabetes, hypertension, dyslipidemias, cardiovascular disease, gallstones, osteoarthritis, and certain forms of cancers.

When the pharmacological composition comprises another agent for treating a metabolic disorder or the treatment includes a second pharmacological composition comprising an agent for treating a metabolic disorder, the agent includes, but are not limited to, cannabinoid (CB1) receptor antagonists, glucagon like peptide 1 (GLP-1) receptor agonists, lipase inhibitors, leptin, tetrahydrolipstatin, 2-4-dinitrophenol, acarbose, sibutramine, phentamine, fat absorption blockers, simvastatin, mevastatin, ezetimibe, atorvastatin, sitagliptin, metformin, orlistat, Qnexa, topiramate, naltrexone, bupriopion, phentermine, losartan, losartan with hydrochlorothiazide, and the like.

Suitable agents of use in combination with a compound of the present invention, include, but are not limited to:
(a) neuromedin U receptor agonist as disclosed in Published International Application No. WO2007/109135.
(b) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73, 945; and MOR 14, and the like; (7) alpha-amylase inhibitors such as tendamistat, trestatin, and A1-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin suspension (lente and ultralente); insulin glargine, insulin zinc suspension (lente and ultralente); Lys-Pro insulin, GLP-1 (17-36), GLP-1 (73-7) (insulintropin); GLP-1 (7-36)-NH2 exenatide/Exendin-4, Exenatide LAR, Linaglutide, AVE0010, CJC 1131, BIM51077, CS 872, THO318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), naveglitazar, muraglitazar, peliglitazar, tesaglitazar (GALIDA), reglitazar (JTT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14) other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl] pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promoters such as those disclosed in WO 03/007990; (21) fixed combinations of PPARγ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (also called RUP3; SNORF 25) such as RUP3, HGPRBMY26, PFI 007, SNORF 25; (25) adenosine receptor 2B antagonists such as ATL-618, ATl-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002;

(c) lipid lowering agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, rosuvastatin, simvastatin, rosuvastatin (ZD-4522), and the like, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, benzafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid®, and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), (16) PPARγ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), 58921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (d) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (e) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191, 160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521, 283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (GlaxoSmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358, 951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316, 243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. No. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8- tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin, saxagliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Technologies), PEGylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like.

Specific compounds that can be used in combination with the OXM analogs disclosed herein include specific CB1 antagonists/inverse agonists include those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl) {3-[(1S)-1-(3,5-difluorophenyl)-2-hydroxy-2-methylpropyl]azetidin-1-yl}methyl)benzonitrile, 3-((S)-(4-chlorophenyl) {3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl)benzonitrile, 3-((1S)-1-{[(1S)-(3-cyanophenyl)(4-cyanophenyl)methyl]azetidin-3-yl}-2-fluoro-2-methylpropyl)-5-fluorobenzonitrile, 3-[(S)-(4-chlorophenyl) (3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl) {3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1, 2,4-oxadiazol-3-yl)phenyl]-2-methylpropyl}azetidin-1-yl) methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-(S)-(4-cyanophenyl) [3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl) [3-(1,3,4-oxadiazol-2-yl)phenyl]methyl}azetidin-3-yl)-2-fluoro-2-methylpropyl]-5-fluorobenzonitrile, 3-[(1S)-1-{1-(S)-(4-chlorophenyl)[3-(1,3,4-oxadiazol-2-yl)phenyl] methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl] methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl] azetidin-1-yl}[3-(5-oxo-4,5-dihydro-1,3,4-oxadiazol-2-yl) phenyl]methyl}-benzonitrile, ACOMPLIA (rimonabant, N-(1-piperidinyl)-5-(4-chlorophenyl)-1-(2,4-dichlorophenyl)-4-methylpyrazole-3-carboxamide, SR141716A), 3-(4-chlorophenyl-N'-(4-chlorophenyl)sulfonyl-N-methyl-4-phenyl-4,5-dihydro-1H-pyrazole-1-carboxamide (SLV-319), taranabant, N-[(1S,2S)-3-(4-Chlorophenyl)-2-(3-cyanophenyl)-1-methylpropyl]-2-methyl-2-[[5-(trifluoromethyl)-2-pyridinyl]oxy]propanamide, and pharmaceutically acceptable salts thereof.

Specific NPY5 antagonists that can be used in combination with the OXM analogs disclosed herein include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6-azaisobenzofuran-1 (3H),1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

Specific ACC-1/2 inhibitors that can be used in combination with the OXM analogs disclosed herein include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{[(8-cyclopropyl-4-methoxyquinolin-2-yl)carbonyl]-4-oxospiro [chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro [chroman-2,4'-piperidin]-4-one; and pharmaceutically acceptable salts and esters thereof. Specific MCH1R antagonist compounds that can be used in combination with the OXM analogs disclosed herein include: 1-{4-[(1-ethylazetidin-3-yl)oxy]phenyl}-4-[(4-fluorobenzyl)oxy]pyridin-2 (1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2 (1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl) oxy]phenyl}pyridin-2(1H)-one, and 4-[(5-chloropyridin-2-yl)methoxy]-1-(4-{[(2S)-1-ethylazetidin-2-yl] methoxy}phenyl)pyridin-2(1H)-one, or a pharmaceutically acceptable salt thereof.

A specific DPP-IV inhibitor that can be used in combination with the OXM analogs disclosed herein is 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, or a pharmaceutically acceptable salt thereof.

Specific H3 (histamine H3) antagonists/inverse agonists that can be used in combination with the OXM analogs disclosed herein include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d] pyrimidin-4(3H)-one, 2-ethyl-3-(4-{3-[(3S)-3-methylpiperidin-1-yl]propoxy}phenyl)pyrido[2,3-d] pyrimidin-4(3H)-one 2-methyl-3-(4-{3-[(3S)-3-methylpiperidin-1-yl]propoxy}phenyl)pyrido[4,3-d] pyrimidin-4(3H)-one, 3-{4-[(1-cyclobutyl-4-piperidinyl) oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)- quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methyl-pyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with the OXM analogs disclosed herein include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with the OXM analogs disclosed herein include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl) ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof.

Additionally, other peptide analogs and mimetics of the incretin hormone glucagon-like peptide 1 (GLP-1), may also be of use in combination with the OXM analogs disclosed herein.

Methods of administrating the pharmacological compositions comprising the one or more OXM analogs disclosed herein to an individual include, but are not limited to, intradermal, intramuscular, intraperitoneal, intravenous, subcutaneous, intranasal, epidural, and oral routes. The compositions can be administered by any convenient route, for example by infusion or bolus injection, by absorption through epithelial or mucocutaneous linings (for example, oral mucosa, rectal and intestinal mucosa, and the like), ocular, and the like and can be administered together with other biologically-active agents. Administration can be systemic or local. In addition, it may be advantageous to administer the composition into the central nervous system by any suitable route, including intraventricular and intrathecal injection. Intraventricular injection may be facilitated by an intraventricular catheter attached to a reservoir (for example, an Ommaya reservoir). Pulmonary administration may also be employed by use of an inhaler or nebulizer, and formulation with an aerosolizing agent. It may also be desirable to administer the one or more OXM analogs disclosed herein locally to the area in need of treatment; this may be achieved by, for example, and not by way of limitation, local infusion during surgery, topical application, by injection, by means of a catheter, by means of a suppository, or by means of an implant.

Various delivery systems are known and can be used to administer the OXM analogs disclosed herein including, but not limited to, encapsulation in liposomes, microparticles, microcapsules; minicells; polymers; capsules; tablets; and the like. In one embodiment, the OXM analogs disclosed herein may be delivered in a vesicle, in particular a liposome. In a liposome, the OXM analogs disclosed herein are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,837,028 and U.S. Pat. No. 4,737,323. In yet another embodiment, the OXM analogs disclosed herein can be delivered in a controlled release system including, but not limited to: a delivery pump (See, for example, Saudek, et al., New Engl. J. Med. 321: 574 (1989) and a semi-permeable polymeric material (See, for example, Howard, et al., J. Neurosurg. 71: 105 (1989)). Additionally, the controlled release system can be placed in proximity of the therapeutic target (for example, the brain), thus requiring only a fraction of the systemic dose. See, for example, Goodson, In: *Medical Applications of Controlled Release*, 1984. (CRC Press, Bocca Raton, Fla.).

The amount of the compositions comprising one or more of the OXM analogs disclosed herein which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. Ultimately, the attending physician will decide the amount of the composition with which to treat each individual patient. Initially, the attending physician will administer low doses of the composition and observe the patient's response. Larger doses of the composition may be administered until the optimal therapeutic effect is obtained for the patient, and at that point the dosage is not increased further. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases. However, suitable dosage ranges for intravenous administration of the compositions comprising the one or more OXM analogs disclosed herein are generally about 5-500 micrograms (µg) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient. Ultimately the attending physician will decide on the appropriate duration of therapy using compositions comprising the one or more OXM analogs disclosed herein of the present invention. Dosage will also vary according to the age, weight and response of the individual patient.

Further provided is a pharmaceutical pack or kit, comprising one or more containers filled with one or more of the ingredients of the pharmaceutical compositions and OXM analogs disclosed herein. Optionally associated with such container(s) may be a notice in the form prescribed by a governmental agency regulating the manufacture, use or sale of pharmaceuticals or biological products, which notice reflects approval by the agency of manufacture, use or sale for human administration.

All references disclosed herein are incorporated herein in their entirety.

The following examples are intended to promote a further understanding of the present invention.

Example 1

The synthesis of the Oxyntomodulin (OXM) analogs was essentially as follows. The OXM analogs shown in Table 2 below were synthesized by solid phase using Fmoc/t-Bu chemistry on a peptide multisynthesizer APEX 396 (Advanced Chemtech) using a 40-well reaction block. Each peptide was synthesized in a single well. For peptide amides, 0.1 g of an aminomethylated polystyrene LL (100-200 mesh, 0.41 mmol/g) (Novabiochem) resin derivatized with a modified Rink linker p-[(R,S)-α-[9H-Fluoren-9-yl-methoxyformamido]-2,4-dimethoxybenzyl]-phenoxyacetic acid (Rink, H., 1987, *Tetrahedron Lett.* 28:3787-3789; Bernatowicz, M. S. et al., 1989, *Tetrahedron Lett.* 30:4645-4667) was used. All the amino acids were dissolved at a 0.5 M concentration in a solution of 0.5M HOBt (Hydroxybenzotriazole) in DMF. The acylation reactions were performed for 45 minutes with six-fold excess of activated amino acid over the resin free amino groups. The amino acids were activated with equimolar amounts of HBTU (2-(1H-benzotriazole-1-yl)-1,1,3,3-tetramethyluronium hexafluorophosphate) and a two-fold molar excess of DIEA (N,N-diisopropylethylamine).

Alternatively, the peptides were synthesized by solid phase using Fmoc/t-Bu chemistry on a Pioneer Peptide Synthesizer (Applied Biosystems). In this case, 0.1 g of a resin Fmoc-Linker AM-Champion, 1% cross-linked (Biosearch Technologies, Inc.) and a PEG-PS-based resin derivatized with a modified Rink linker p-[(R,S)-α-[9H-Fluoren-9-yl-methoxyformamido]-2,4-dimethoxybenzyl]-phenoxyacetic acid (Rink, H., 1987, *Tetrahedron Lett.* 28:3787-3789; Bernatowicz, M. S. et al., 1989, *Tetrahedron Lett.* 30:4645-4667) was used. All the acylation reactions were performed for 60 minutes with a four-fold excess of activated amino acid over the resin free amino groups following the end of peptide assembly on the synthesizer; double coupling was performed for N-terminal Aib and His.

The side chain protecting groups were: OMpe (O-3-Methyl-pent-3-yl) for Asp; tert-butyl for Glu, Ser, D-Ser, Thr and Tyr; trityl for Asn, Cys, Gln, and His; and, tert-butoxy-carbonyl for Lys, Trp; and, 2,2,4,6,7-pentamethyl-dihydrobenzofuran-5-sulfonyl for Arg.

For OXM110 and OXM177, Lysine-Palmitoyl was manually acylated by reaction with equimolar amounts of HBTU (2-(1H-benzotriazole-1-yl)-1,1,3,3-tetramethyluronium hexafluorophosphate) and a 2-fold molar excess of DIEA (N,N-diisopropylethylamine). The acylation reaction was performed for 120 minutes with a three-fold excess of activated acylant over the resin free amino groups.

At the end of the synthesis, the dry peptide-resins were individually treated with 20 mL of the cleavage mixture, 88% trifluoroacetic acid (TFA), 5% phenol, 2% triisopropylsilane and 5% water (Sole, N. A. and G. Barany, 1992, *J. Org. Chem.* 57:5399-5403) for 1.5 hours at room temperature. Each resin was filtered and the solution was added to cold methyl-t-butyl ether in order to precipitate the peptide. After centrifugation, the peptide pellets were washed with fresh cold methyl-t-butyl ether to remove the organic scavengers. The process was repeated twice. Final pellets were dried, resuspended in $H_2O$, 20% acetonitrile, and lyophilized.

The crude peptides were purified by reverse-phase HPLC using preparative Waters RCM Delta-Pak™ $C_{-4}$ cartridges (40×200 mm, 15 µm) and using as eluents (A) 0.1% TFA in water and (B) 0.1% TFA in acetonitrile. The following gradient of eluent B was used: 20%-20% over five minutes and 20%-35% over 20 minutes for the OXM229 (the peptide thiolated precursor of OXM36 and OXM115), OXM29 (the thiolated precursor of OXM70 and OXM216), OXM208 (the peptide thiolated precursor of OXM212), and OXM209 (the peptide thiolated precursor of OXM213).

For peptides OXM110 and 177, the following gradient of eluent B was used: 32%-32% over five minutes and 32%-42% over 20 minutes flow rate 80 mL/min. Analytical HPLC was performed on a Alliance Waters Chromatograph, with a ACE C-4 (300 A), 3 um column, 150×4.6 mm, (CPS analitica p/n ACE-213-1546), at 45 C.°, using $H_2O$, 0.1% TFA (A) and $CH_3CN$, 0.1% TFA (B) as solvents and the following linear gradient: 20%-20% B (in five minutes)—35% B (in 20 minutes)-80% B (in two minutes), flow 1 mL/min. The purified peptide was characterized by electrospray mass spectrometry on a Micromass LCZ platform.

Example 2

Synthesis of Oxyntomodulin (OXM) cholesterylated analogs OXM36, OXM70, OXM115, OXM212, OXM213, and OXM216 was as follows.

The reactions were run under conditions that permit the formation of a thioether bond. The cholesterylated OXM peptides were then isolated using reverse-phase HPLC and characterized on a Micromass LCZ platform. The analogs OXM36, 70, 212, and 213 were synthesized from the thiol containing OXM peptide precursor OXM229, OXM208, and 209, respectively, by reaction with the bromo derivative, cholest-5-en-3-yl bromoacetate having the structure

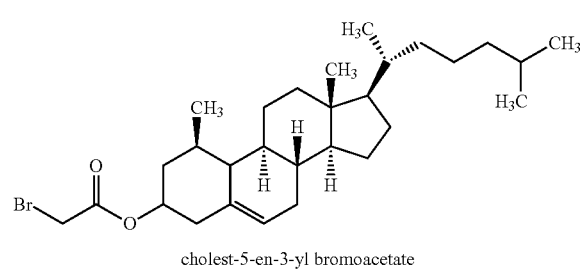

cholest-5-en-3-yl bromoacetate to produce conjugates attached via a thioether bond. Briefly, 30 mg of peptide precursor were dissolved in one mL of DMSO (conc. 30 mg/mL) and a one molar excess of cholest-5-en-3-yl bromoacetate dissolved in THF (conc. 20 mg/mL) was added. Then 1% by volume of DIPEA (N,N-diisopropyl-ethylamine) was added to the mixture; after 30 minutes of incubation, the peptide solution was purified by RP-HPLC and characterized on a Micromass LCZ platform.

The peptides OXM115 and 216 were synthesized from the thiol containing OXM peptide precursor OXM229 and OXM29 to produce analogs by reaction with the bromo derivative, cholest-5-en-3-yl 1-bromo-2-oxo-6,9,12,15-tetraoxa-3-azaoctadecan-18-oate

Example 3

PEGylation reactions were run under conditions permitting thioester bond formation. The PEGylated OXM peptide was then isolated using reverse-phase HPLC or ion exchange chromatography and size exclusion chromatography (SEC). PEGylated OXM analogs were characterized using RP-HPLC, HPLC-SEC and MALDI-Tof Mass Spectrometry.

OXM33, 34, 35, 36 and 54 peptides were synthesized from the thiol-containing OXM peptide precursor OXM229 to produce analogs with PEG covalently attached via a thioether bond.

Synthesis of OXM33

10 mg of peptide precursor (2.2 μmoles) were dissolved in 0.2 mL of HEPES 0.1M pH 7.3, Guanidinium Chloride 6M, 2 mM EDTA. 22 mg of MPEG-MAL-5000 (NEKTAR 2F2MOH01) (4.4 μmoles) dissolved in 0.4 mL HEPES 0.1M, pH 7.3 (1:2 mole/mole ratio of peptide to PEG) was added to this solution. After 1 hour incubation, the PEGylated peptide was purified by RP-HPLC and characterized by MALDI-TOF.

Synthesis of OXM34

10 mg of peptide precursor (2.2 μmoles) were dissolved in 0.2 mL of HEPES 0.1M pH 7.3, Guanidinium Chloride 6M, 2 mM EDTA. 80 mg of MPEG-MAL-20K (NEKTAR 2F2M0P01) (4.0 μmoles) dissolved in 0.5 mL HEPES 0.1M, pH 7.3 (1:1.8 mole/mole ratio of peptide to PEG) was added to this solution. After 1 hour incubation, the PEGylated peptide was purified by RP-HPLC and characterized by MALDI-TOF.

Synthesis of OXM35

10 mg of peptide precursor (0.92 μmoles) were dissolved in 0.4 mL of HEPES 0.1M pH 7.3, Guanidinium Chloride 6M, 2 mM EDTA. 70 mg of MPEG2-MAL-40K (NEKTAR 2D3Y0T01) (1.7 μmoles) dissolved in 0.8 mL HEPES 0.1M, pH 7.3 in a 1:1.8 mole/mole ratio of peptide to PEG was added to this solution. After 1 hour incubation, the PEGylated peptide was purified by RP-HPLC and characterized by MALDI-TOF.

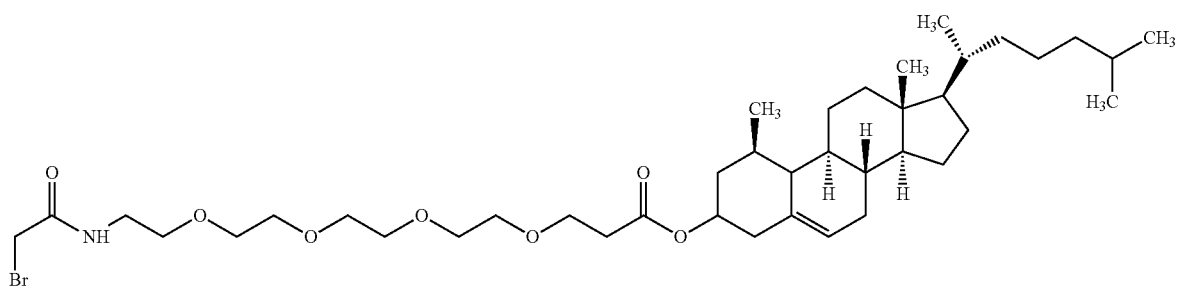

cholest-5-en-3-yl 1-bromo-2-oxo-6,9,12,15-tetraoxa-3-azaoctadecan-18-oate to produce conjugates attached via a thioether bond. Briefly, 30 mg of peptide precursor were dissolved in 1 mL of DMSO (conc. 30 mg/mL) and a one molar excess of cholest-5-en-3-yl 1-bromo-2-oxo-6,9,12,15-tetraoxa-3-azaoctadecan-18-oate dissolved in THF (conc. 20 mg/mL) was added. Then 3% by volume of DIPEA (N,N-diisopropyl-ethylamine) was added to the mixture; after 30 minutes of incubation, the peptide solution was purified by RP-HPLC and characterized on a Micromass LCZ platform.

The control peptide OXM54, was prepared by incubating the thiol containing peptide precursor with 10 eq. of iodoacetamide in 0.1 M TrisHCl pH 7.5, 6M guanidinium chloride. After 30 minutes incubation the peptide was purified by RP-HPLC and characterized by electrospray mass spectrometry.

Synthesis of OXM103, OXM105, OXM107, OXM113

10 mg of the corresponding peptide precursors (2.26 μmoles) were dissolved in 2 mL of urea 8M, HEPES 0.1M pH 7.3, 2 mM EDTA. 109 mg of MPEG2-MAL-40K (NEKTAR 2D3Y0T01) (2.71 µmoles) dissolved in H$_2$O (1:1.2 mole/mole ratio of peptide to PEG) was added to this solution. After 1 hour incubation, the PEGylated peptide solution was acidified to 1% acetic acid and purified by cation exchange chromatography (IXC) on TSK CM-650S with a linear gradient of NaCl in sodium acetate 50 mM pH 4.8. The IXC purified PEGylated-peptide was further purified by SEC and characterized by MALDI-TOF Synthesis of OXM109

10 mg of the corresponding peptide precursors (2.25 µmoles) were dissolved in 2 ml urea 8M, HEPES 0.1M pH 7.3, 2 mM EDTA. 108 mg of MPEG2-MAL-40K (NEKTAR 2D3Y0T01) (2.7 µmoles) dissolved in 2 mL H$_2$O (1:1.2 mole/mole ratio of peptide to PEG) was added to this solution. After 1 hour incubation, the PEGylated peptide solution was acidified to 1% acetic acid and purified by cation exchange chromatography (IXC) on TSK CM-650S with a linear gradient of NaCl in sodium acetate 50 mM pH 4.8. The IXC purified PEGylated-peptide was further purified by SEC and characterized by MALDI-TOF.

Example 4

The OXM peptide analogs that that display full agonistic activity on the GLP-1 and the Glucagon receptors and shown in Table 2 were synthesized as follows.

The peptides OXM290, 291, 292, 293 and 294 that are precursors of OXM301, OXM302, OXM303, OXM304 and OXM305 (See Table 2) were synthesized by solid phase using Fmoc/t-Bu chemistry on a peptide multisynthesizer Simphony Protein Technologies Inc. For peptide amides, 0.5 g of a resin Aminomethylated polystyrene LL (100-200 mesh, 0.41 mmol/g) (Novabiochem) resin derivatized with a modified Rink linker p-[(R,S)-α-[9H-Fluoren-9-yl-methoxyformamido]-2,4-dimethoxybenzyl]-phenoxyacetic acid (Rink, Tetrahedron Lett. 28:3787-3789 (1987); Bernatowicz et al., Tetrahedron Lett. 30:4645-4667 (1989)) was used. All the amino acids were dissolved at a 0.5 M concentration in a solution of 0.5 M HOBt (Hydroxybenzotriazole) in DMF. The acylation reactions were performed for 60 minutes with 8-fold excess of activated amino acid over the resin free amino groups. The amino acids were activated with equimolar amounts of HBTU (2-(1H-benzotriazole-1-yl)-1,1,3,3-tetramethyluronium hexafluorophosphate), solution 0.5 M in DMF, and a 2-fold molar excess of DIEA (N,N-diisopropylethylamine), solution 2 M in NMP.

The side chain protecting groups were: OMpe (O-3-Methyl-pent-3-yl) for Asp; tert-butyl for Glu, Ser, D-Ser, Thr and Tyr; trityl for Asn, Cys, Gln and His; tert-butoxycarbonyl for Lys, Trp; and, 2,2,4,6,7-pentamethyldihydrobenzofuran-5-sulfonyl for Arg; Boc-His(Trt)-OH was used in the synthesis.

At the end of the synthesis, the dry peptide-resins were individually treated with 25 mL of the cleavage mixture, 82.5% trifluoroacetic acid (TFA), 5% phenol, 5% thioanisole, 2.5% Ethandithiole, and 5% water for 1.5 hours at room temperature. Each resin was filtered and the volume of the solution was reduced then added to cold methyl-t-butyl ether in order to precipitate the peptide. After centrifugation, the peptide pellets were washed with fresh cold methyl-t-butyl ether to remove the organic scavengers. The process was repeated twice. Final pellets were dried, resuspended in H$_2$O, 20% acetonitrile, and lyophilized.

The crude peptides were purified by reverse-phase HPLC using preparative Waters RCM Delta-Pak™ C$_{-4}$ cartridges (40×200 mm, 15 µm) and using as eluents (A) 0.1% TFA in water and (B) 0.1% TFA in acetonitrile. The following gradient of eluent B was used: 22%-22% over 5 min and 22%-32% over 20 min for OXM301 precursor, 22%-22% over 5 min and 22%-35% over 20 min for OXM302 precursor, 25%-25% over 5 min and 25%-40% over 20 min for OXM303 precursor, 25%-25% over 5 min and 25%-35% over 20 min for OXM304 precursor and OXM305 precursor, flow rate 80 mL/min, wavelength 214 nm. Analytical HPLC was performed on a Alliance Waters Chromatograph, with a ACE C-4 (300 A), 3 um column, 150×4.6 mm, (CPS analitica p/n ACE-213-1546), at 45° C., using H$_2$O, 0.1% TFA (A) and CH3CN, 0.1% TFA (B) as solvents and the following linear gradient: 25%-25% B (in 5 min)-40% B (in 20 min)-80% B (in 2 minutes), flow 1 mL/min. The purified peptides were characterized by electrospray mass spectrometry on a Micromass LCZ platform.

Synthesis of C$_7$ conjugates was as follows. The peptides OXM301, OXM302, OXM303, OXM304, and OXM305 were synthesized from the thiol containing OXM peptide precursor OXM290-294 respectively to produce derivatives with the C$_7$ group covalently attached via the thioether group of the cysteine residue at the C-terminus. As an example of derivatization of the precursor: 40 mg of peptide precursor were dissolved in 1.33 mL of DMSO (conc. 30 mg/mL) and a 2.1 molar excess of cholest-5-en-3-yl 1-bromo-2-oxo-6,9,12,15-tetraoxa-3-azaoctadecan-18-oate dissolved in THF (conc. 30 mg/mL) was added. Then, 5% by volume of DIPEA (N,N-diisopropyl-ethylamine) was added to the mixture; after 30 minutes of incubation, was quenched by the drop-wise addition of ammonium acetate (solution of 1 M in water) until turbidity of the solution.

The solution was then directly loaded onto a reverse-phase Waters RCM Delta-Pak™ C$_{-4}$ cartridges (20×200 mm, 15 µm, 300 A) using as eluent 0.5 M ammonium acetate, 20% MetOH, 25% acetonitrile in water, pH 7.8, at 5 mL/min. An isocratic elution was run for 15 minutes with this buffer at 30 mL/min. Then the eluents were changed to: (A) 0.2% acetic acid, 20% MetOH in water (B) 0.2% acetic acid, 20% MetOH in acetonitrile and then the following gradient was run: 25% (B)-35% (B) in 5'—70% (B) in 20'—80% (B) in 2'—80% (B) for 3', flow 30 mL/min, wavelength 230 nm.

The final peptides were characterized on an Alliance Waters Chromatograph, with a ACE C-4 (300 A), 3 um column, 150×4.6 mm, (CPS analitica p/n ACE-213-1546), at 45° C., using H$_2$O, 0.1% TFA (A) and CH$_3$CN, 0.1% TFA (B) as solvents and the following linear gradient: 40%-40% B (in 5 min)—70% B (in 20 min)—80% B (in 2 min), flow 1 mL/min. The peptides were characterized by electrospray mass spectrometry on a Micromass LCZ platform.

Example 5

Peptides OXM237-OXM308 and OXM345-OXM414 were synthesized by solid phase using Fmoc/t-Bu chemistry on a peptide multisynthesizer Simphony Protein Technologies Inc. For peptide amides 0.5 g of a resin Aminomethylated thioethers LL (100-200 mesh, 0.41 mmol/g) (Novabiochem) resin derivatized with a modified Rink linker p-[(R,S)-α-[9H-Fluoren-9-yl-methoxyformamido]-2,4-di-methoxybenzyl]-phenoxyacetic acid (Rink, H., 1987, *Tetrahedron Lett.* 28:3787-3789; Bernatowicz, M. S. et al., 1989, *Tetrahedron Lett.* 30:4645-4667) was used. For peptide acids 0.5 g of a resin Aminomethylated thioether LL (100-200 mesh, 0.41 mmol/g) (Novabiochem) resin derivatized with 4-hydroxymethylphenoxyacetic acid. All the amino acids were dissolved at a 0.5 M concentration in a solution of 0.5M HOBt (Hydroxybenzotriazole) in DMF. The acylation reactions were performed for 60 min with 8-fold excess of activated amino acid over the resin free amino groups. The amino acids were activated with equimolar amounts of HBTU (2-(1H-benzotriazole-1-yl)-1,1,3,3-tetramethyluronium hexafluorophosphate), solution 0.5 M in DMF, and a 2-fold molar excess of DIEA (N,N-diisopropylethylamine), solution 2M in NMP.

The side chain protecting groups were: Ompe (O-3-Methyl-pent-3-yl) for Asp; tert-butyl for Glu, Ser, D-Ser, Thr and Tyr; trityl for Asn, Cys, Gln and His; tert-butoxycarbonyl for Lys, Trp; and, 2,2,4,6,7-pentamethyldihydrobenzofuran-5-sulfonyl for Arg; Boc-His(Trt)-OH was used in the synthesis.

For peptides OXM392, 395 and 398, Glu16 and Lys20 were incorporated as Glu(Oall) and Lys(Alloc). At the end of the assembly the resins were dried, the protecting groups of Glu(Oall) and Lys(Alloc) were removed and the lactam bridge was formed by incubating the resin with 5 molar excess of HBTU and 10 molar excess of DIPEA.

For lipidated peptides such as OXM404, 407, 408, 410, 411, 414, 415, 416, 417, 418, 419, 420 the lysine to be derivatized on the side chain was incorporated as Lys (Alloc). At the end of the assembly the Alloc protecting group was removed and the synthesis was completed by condensation of the γ-carboxyglutamic acid residues and the palmitic acid using HBTU and DIPEA as activators.

At the end of the synthesis, the dry peptide-resins were individually treated with 25 mL of the cleavage mixture, 82.5% trifluoroacetic acid (TFA), 5% phenol, 5% thioanisole, 2.5% ethandithiole and 5% water for 1.5 hours at room temperature. Each resin was filtered and the volume of the solution was reduced then added to cold methyl-t-butyl ether in order to precipitate the peptide. After centrifugation, the peptide pellets were washed with fresh cold methyl-t-butyl ether to remove the organic scavengers. The process was repeated twice. Final pellets were dried, resuspended in $H_2O$, 20% acetonitrile, and lyophilized.

The crude peptides were purified by reverse-phase HPLC using preparative Waters RCM Delta-Pak™ $C_{-4}$ cartridges (40×200 mm, 15 μm) and using as eluents (A) 0.1% TFA in water and (B) 0.1% TFA in acetonitrile. Analytical HPLC was performed on a Alliance Waters Chromatograph, with a ACE C-4 (300 A), 3 um column, 150×4.6 mm, (CPS analitica p/n ACE-213-1546), at 45° C., using $H_2O$, 0.1% TFA (A) and CH3CN, 0.1% TFA (B) as solvents. The purified peptides were characterized by electrospray mass spectrometry on a Micromass LCZ platform.

Synthesis of $C_5$ conjugates was a follows. The peptide OXM238 was synthesized from a thiol containing OXM peptide precursor to produce derivatives with the acetamide covalently attached via the thioethers group of the cysteine residue at the C-terminus. As an example of derivatization of the precursor: 50 mg of peptide precursor were dissolved in Tris HCl buffer 0.25 M, EDTA 2 mM, Urea 6M pH 8.3 (conc. 30 mg/mL) and a 10 molar excess of iodoacetamide dissolved in DMSO (conc. 30 mg/mL) was added. After 30 minutes the reaction is complete. The solution is acidified with acetic acid and purified on preparative HPLC.

Synthesis of $C_4$ conjugates was as follows. The peptides OXM345, OXM355, OXM357, OXM373 were synthesized from the thiol containing OXM peptide precursors respectively to produce derivatives with the cholesterol group covalently attached via the thioethers group of the cysteine at the C-terminus. As an example of derivatization of the precursor: 40 mg of peptide precursor were dissolved in DMSO (conc. 30 mg/mL) and a 2.1 molar excess of cholest-5-en-3-yl 1-bromo-2-oxo-6,9,12,15-tetraoxa-3-azaoctadecan-18-oate dissolved in THF (conc. 30 mg/mL) was added. Then 5% by volume of DIPEA (N,N-diisopropyl-ethylamine) was added to the mixture; after 30 min of incubation, was quenched by the drop-wise addition of ammonium acetate (solution of 1 M in water) until turbidity of the solution was reached.

The solution was then directly loaded onto a reverse-phase Waters RCM Delta-Pak™ $C_{-4}$ cartridges (20×200 mm, 15 μm, 300 A) using as eluent 0.5 M ammonium acetate, 20% MetOH, 25% acetonitrile in water, pH 7.8, at 5 mL/min. An isocratic elution was run for 15 min with this buffer at 30 mL/min. Then the eluents were changed to: (A) 0.2% acetic acid, 20% MetOH in water (B) 0.2% acetic acid, 20% MetOH in acetonitrile.

The final peptides were characterized on an Alliance Waters Chromatograph, with a ACE C-4 (300 A), 3 um column, 150×4.6 mm, (CPS analitica p/n ACE-213-1546), at 45° C., using $H_2O$, 0.1% TFA (A) and CH3CN, 0.1% TFA (B) as solvents. The peptides were characterized by electrospray mass spectrometry on a Micromass.

Synthesis of $C_7$ conjugates was as follows. The peptides OXM359, OXM361, OXM374, OXM380, OXM383 and OXM388 were synthesized from the thiol containing OXM peptide precursor to produce derivatives with the Oxa4-cholesterol covalently attached via a thioether bond to the cysteine residue at the C-terminus. As an example of derivatization of the precursor: 25 mg of peptide precursor were dissolved in 1.33 mL of DMSO (conc. 30 mg/mL) and a 1.1 molar excess of cholest-5-en-3-yl 1-bromo-2-oxo-6,9,12,15-tetraoxa-3-azaoctadecan-18-oate dissolved in THF (conc. 30 mg/mL) was added. Then 5% by volume of DIPEA (N,N-diisopropyl-ethylamine) was added to the mixture; after 30 min of incubation, was quenched by the drop-wise addition of ammonium acetate (solution of 1 M in water) until turbidity of the solution was reached.

The solution was then directly loaded onto a reverse-phase Waters RCM Delta-Pak™ $C_{-4}$ cartridges (20×200 mm, 15 μm, 300 A) using as eluent 0.5 M ammonium acetate, 20% MetOH, 25% acetonitrile in water, pH 7.8, at 5 mL/min. An isocratic elution was run for 15 min with this buffer at 30 mL/min. Then the eluents were changed to: (A) 0.2% acetic acid, 20% MetOH in water (B) 0.2% acetic acid, 20% MetOH in acetonitrile and then the following gradient was run: 25% (B)-35% (B) in 5'—70% (B) in 20'—80% (B) in 2'—80% (B) for 3', flow 30 mL/min, wavelength 230 nm.

The final peptides were characterized on an Alliance Waters Chromatograph, with a ACE C-4 (300 A), 3 um column, 150×4.6 mm, (CPS analitica p/n ACE-213-1546), at 45° C., using $H_2O$, 0.1% TFA (A) and CH3CN, 0.1% TFA (B) as solvents. The peptides were characterized by electrospray mass spectrometry on a Micromass LCZ platform.

Synthesis of $C_9$ conjugates was as follows. The peptide OXM381 was synthesized from the thiol containing OXM peptide precursor to produce derivatives with the Oxa12-cholesterol covalently attached via the maleimide thioether bond to the cysteine residue at the C-terminus. As an example of derivatization of the precursor: 25 mg of peptide precursor were dissolved in DMSO (conc. 30 mg/mL) and a 1.5 molar excess of cholest-5-en-3-yl N-[43-(2,5-dioxo-2, 5-dihydro-1H-pyrrol-1-yl)-41-oxo-4,7,10,13,16,19,22,25, 28,31,34,37-dodecaoxa-40-azatritetracontan-1-oyl]glycinate dissolved in THF (conc. 20 mg/mL) was added. Then 2% by volume of DIPEA (N,N-diisopropyl-ethylamine) was added to the mixture; after 4-6 hours of incubation, the reaction was quenched with glacial acetic acid and directly loaded on reverse-phase HPLC and purified. The final peptide was characterized on an Alliance Waters Chromatograph, with a ACE C-4 (300 A), 3 um column, 150×4.6 mm, (CPS analitica p/n ACE-213-1546), at 45° C., using $H_2O$, 0.1% TFA (A) and CH3CN, 0.1% TFA (B) as solvents. The peptides were characterized by electrospray mass spectrometry on a Micromass LCZ platform.

Synthesis of $C_{10}$ conjugates was as follows. The peptides OXM392, 395, 398, 399, 400, and 401 were synthesized from the thiol containing OXM peptide precursors to produce derivatives with the Oxa12-cholesterol covalently attached via a thioether bond to the cysteine residue at the C-terminus. As an example of derivatization of the precursor: 25 mg of peptide precursor were dissolved in DMSO (conc. 30 mg/mL) and a 1.5 molar excess of cholest-5-en-3-yl 1-bromo-2-oxo-6,9,12,15,18,21,24,27,30,33,36,39-dodecaoxa-3-azadotetracontan-42-oate in THF (conc. 20 mg/mL) was added. Then 2% by volume of DIPEA (N,N-diisopropyl-ethylamine) was added to the mixture; after 4-6 hours of incubation, the reaction was quenched with glacial acetic acid and directly loaded on reverse-phase HPLC and purified. The final peptide was characterized on an Alliance Waters Chromatograph, with a ACE C-4 (300 A), 3 um column, 150×4.6 mm, (CPS analitica p/n ACE-213-1546), at 45° C., using $H_2O$, 0.1% TFA (A) and CH3CN, 0.1% TFA (B) as solvents. The peptides were characterized by electrospray mass spectrometry on a Micromass LCZ platform.

Synthesis of $C_{11}$ conjugates was as follows. The peptides OXM412 was synthesized from the thiol containing OXM peptide precursor to produce derivatives with the Oxa24-cholesterol covalently attached via a thioether bond to the cysteine residue at the C-terminus. As an example of derivatization of the precursor: 25 mg of peptide precursor were dissolved in DMSO (conc. 30 mg/mL) and a 1.5 molar excess of cholest-5-en-3-yl 1-bromo-2-oxo-6,9,12,15,18,21,24,27,30,33,36,39,42,45,48,51,54,57,60,63,66,69,72,75-tetracosaoxa-3-azaoctaheptacontan-78-oate in THF (conc. 20 mg/mL) was added. Then 2% by volume of DIPEA (N,N-diisopropyl-ethylamine) was added to the mixture; after 4-6 hours of incubation, the reaction was quenched with glacial acetic acid and directly loaded on reverse-phase HPLC and purified.

The final peptide was characterized on an Alliance Waters Chromatograph, with a ACE C-4 (300 A), 3 um column, 150×4.6 mm, (CPS analitica p/n ACE-213-1546), at 45° C., using $H_2O$, 0.1% TFA (A) and CH3CN, 0.1% TFA (B) as solvents. The peptides were characterized by electrospray mass spectrometry on a Micromass LCZ platform.

Synthesis of $C_{12}$ conjugates was as follows. The peptides OXM421 was synthesized from the thiol containing OXM peptide precursor to produce derivatives with the Oxa12-O-cholesterol covalently attached via a thioether bond to the cysteine residue at the C-terminus. As an example of derivatization of the precursor: 25 mg of peptide precursor were dissolved in DMSO (conc. 30 mg/mL) and a 1.5 molar excess of cholest-5-en-3-yl 1-bromo-2-oxo-6,9,12,15,18,21,24,27,30,33,36-undecaoxa-3-azaoctatriacont-78-oate in THF (conc. 20 mg/mL) was added. Then 2% by volume of DIPEA (N,N-diisopropyl-ethylamine) was added to the mixture; after 4-6 hours of incubation, the reaction was quenched with glacial acetic acid and directly loaded on reverse-phase HPLC and purified.

The final peptide was characterized on an Alliance Waters Chromatograph, with a ACE C-4 (300 A), 3 um column, 150×4.6 mm, (CPS analitica p/n ACE-213-1546), at 45° C., using $H_2O$, 0.1% TFA (A) and CH3CN, 0.1% TFA (B) as solvents. The peptides were characterized by electrospray mass spectrometry on a Micromass LCZ platform.

Example 6

Table 3 shows the structures for the native OXM and OXM analogs that are disclosed herein.

TABLE 3

OXM Peptide Analogs

| SEQ ID NO. | Name | Structure |
|---|---|---|
| 1 | OXM (native) | HSQGTFTSDYSKYLDSRRAQDFVQWLMNTKRNRNNIA |
| 2 | OXM8 (Q3E) | HSEGTFTSDYSKYLDSRRAQDFVQWLMNTKRNRNNIA |
| 3 | OXM9 (Q3D) | HSDGTFTSDYSKYLDSRRAQDFVQWLMNTKRNRNNIA |
| 4 | OXM29 | HαQGTFTSDYSKYLDSRRAQDFVQWLMNTKRNRNNIAC-CONH$_2$ |
| 5 | OXM33 | HsQGTFTSDYSKYLDSRRAQDFVQWLMNTKRNRNNIAC$_1$-CONH$_2$ |
| 6 | OXM34 | HsQGTFTSDYSKYLDSRRAQDFVQWLMNTKRNRNNIAC$_2$-CONH$_2$ |
| 7 | OXM35 | HsQGTFTSDYSKYLDSRRAQDFVQWLMNTKRNRNNIAC$_3$-CONH$_2$ |
| 8 | OXM36 | HsQGTFTSDYSKYLDSRRAQDFVQWLMNTKRNRNNIAC$_4$-CONH$_2$ |
| 9 | OXM67 | HαQGTFTSDYSKYLDSRRAQDFVQWLMNTKRNRNNIAC$_1$-CONH$_2$ |
| 10 | OXM68 | HαQGTFTSDYSKYLDSRRAQDFVQWLMNTKRNRNNIAC$_2$-CONH$_2$ |

TABLE 3-continued

OXM Peptide Analogs

| SEQ ID NO. | Name | Structure |
|---|---|---|
| 11 | OXM69 | HαQGTFTSDYSKYLDSRRAQDFVQWLMNTKRNRNNIAC₃-CONH₂ |
| 12 | OXM70 | HαQGTFTSDYSKYLDSRRAQDFVQWLMNTKRNRNNIAC₄-CONH₂ |
| 13 | OXM99 | HαQGTFTSDYSKYLDSRRAQDFVQWLmNTKRNRNNIAC₃-CONH₂ |
| 14 | OXM100 | HαQGTFTSDYSKYLDSRRAQDFVQWLmNTKRNRNNIAC₆-CONH₂ |
| 15 | OXM103 | HαQGTFTSDYSKYLDSRRAC₃DFVQWLMNTKRNRNNIA-CONH₂ |
| 16 | OXM105 | HαQGTFTSDYSKYLDSRRAQC₃FVQWLMNTKRNRNNIA-CONH₂ |
| 17 | OXM107 | HαQGTFTSDYSKYLDSRRAQDFVC₃WLmNTKRNRNNIA-CONH₂ |
| 18 | OXM109 | HαQGTFTSDYSKYLDSRRAQDFVQWLC₃TKRNRNNIA-CONH₂ |
| 19 | OXM110 | HsQGTFTSDYSKYLDSRRAQDFVQWLMNTKRNRNNIAK(palmitoyl)-CONH₂ |
| 20 | OXM113 | H₂αQGTFTSDYSKYLDSRRAQDFVQWLmNTKRNRNNIAC₃-CONH₂ |
| 21 | OXM115 | HsQGTFTSDYSKYLDSRRAQDFVQWLMNTKRNRNNIAC₇-CONH₂ |
| 22 | OXM121 | HαQGTFTSDYC₃KYLDSRRAQDFVQWLmNTKRNRNNIA-CONH₂ |
| 23 | OXM124 | HαQGTFTSDYSC₃YLDSRRAQDFVQWLmNTKRNRNNIA-CONH₂ |
| 24 | OXM177 | HαQGTFTSDYSKYLDSRRAQDFVQWLMNTKRNRNNIAK(palmitoyl)-CONH₂ |
| 25 | OXM208 | HαQGTFTSDYSKYLDSRRAQDFVQWLnNTKRNRNNIAC-CONH₂ |
| 26 | OXM209 | HαQGTFTSDYSKYLDSRRAQDFVQWLoNTKRNRNNIAC-CONH₂ |
| 27 | OXM212 | HαQGTFTSDYSKYLDSRRAQDFVQWLnNTKRNRNNIAC₄-CONH₂ |
| 28 | OXM213 | HαQGTFTSDYSKYLDSRRAQDFVQWLoNTKRNRNNIAC₄-CONH₂ |
| 29 | OXM216 | HαQGTFTSDYSKYLDSRRAQDFVQWLMNTKRNRNNIAC₇-CONH₂ |
| 30 | OXM229 (OXM33-36 precursor) | HsQGTFTSDYSKYLDSRRAQDFVQWLMNTKRNRNNIAC-CONH₂ |
| 31 | OXM237 | HsQGTFTSDYS KYLDSRRAQDFVQWLmNTKRNRNNIA-C₇-CONH₂ |
| 32 | OXM238 | HsQGTFTSDYSKYLDSRRAQDFVQWLmNTKRNRNNIA-C₅-CONH₂ |
| 33 | OXM259 | H-Acx-QGTFTSDYSKYLDSRRAQDFVQWLMNTKRNRNNIA-CONH₂ |
| 34 | OXM260 | H-Abu-QGTFTSDYSKYLDSRRAQDFVQWLMNTKRNRNNIA-CONH₂ |
| 35 | OXM261 | H-(D-Abu)-QGTFTSDYSKYLDSRRAQDFVQWLMNTKRNRNNIA-CONH₂ |
| 36 | OXM262 | H-Nva-QGTFTSDYSKYLDSRRAQDFVQWLMNTKRNRNNIA-CONH₂ |
| 37 | OXM263 | H-Cpa-QGTFTSDYSKYLDSRRAQDFVQWLMNTKRNRNNIA-CONH₂ |

TABLE 3-continued

OXM Peptide Analogs

| SEQ ID NO. | Name | Structure |
|---|---|---|
| 38 | OXM264 | H-Prg-QGTFTSDYSKYLDSRRAQDFVQWLMNTKRNRNNIA-CONH$_2$ |
| 39 | OXM265 | H-Alg-QGTFTSDYSKYLDSRRAQDFVQWLMNTKRNRNNIA-CONH$_2$ |
| 40 | OXM266 | H-(2-Cha)-QGTFTSDYSKYLDSRRAQDFVQWLMNTKRNRNNIA-CONH$_2$ |
| 41 | OXM267 | H-(Dtbg)-QGTFTSDYSKYLDSRRAQDFVQWLMNTKRNRNNIA-CONH$_2$ |
| 42 | OXM268 | H-Vg-QGTFTSDYSKYLDSRRAQDFVQWLMNTKRNRNNIA-CONH$_2$ |
| 43 | OXM306 | H-Acp-QGTFTSDYSKYLDSRRAQDFVQWLMNTKRNRNNIA-CONH$_2$ |
| 44 | OXM307 | H-Acb-QGTFTSDYSKYLDSRRAQDFVQWLMNTKRNRNNIA-CONH$_2$ |
| 45 | OXM308 | H-Acpe-QGTFTSDYSKYLDSRRAQDFVQWLMNTKRNRNNIA-CONH$_2$ |
| 46 | OXM290 | HsQGTFTSDYSKYLDSEAAQDFVQWLMNTKRNRNNIAC-CONH$_2$ |
| 47 | OXM291 | HsQGTFTSDYSKYLDSRRAQDFVQWLMNTKC-CONH$_2$ |
| 48 | OXM292 | HsQGTFTSDYSKYLDSEAAQDFVQWLMNTKC-CONH$_2$ |
| 49 | OXM293 | HsQGTFTSDYSKYLDSERAQDFVQWLMNTKC-CONH$_2$ |
| 50 | OXM294 | HsQGTFTSDYSKYLDSRAAQDFVQWLMNTKC-CONH$_2$ |
| 51 | OXM301 | HsQGTFTSDYSKYLDSEAAQDFVQWLMNTKRNRNNIAC$_7$-CONH$_2$ |
| 52 | OXM302 | HsQGTFTSDYSKYLDSRRAQDFVQWLMNTKC$_7$-CONH$_2$ |
| 53 | OXM303 | HsQGTFTSDYSKYLDSEAAQDFVQWLMNTKC$_7$-CONH$_2$ |
| 54 | OXM304 | HsQGTFTSDYSKYLDSERAQDFVQWLMNTKC$_7$-CONH$_2$ |
| 55 | OXM305 | HsQGTFTSDYSKYLDSRAAQDFVQWLMNTKC$_7$-CONH$_2$ |
| 56 | OXM311 | HsQGTFTSDYSKYLDSRRAQDFVQWLMNTKK(Palmitoyl)-CONH$_2$ |
| 57 | OXM312 | HsQGTFTSDYSKYLDSEAAQDFVQWLMNTKK(Palmitoyl)-CONH$_2$ |
| 58 | OXM314 | HsQGTFTSDYSKYLDSRRAQDFVQWLMNTK-Ttds-K(Palmitoyl)-CONH$_2$ |
| 59 | OXM313 | HsQGTFTSDYSKYLDSEAAQDFVQWLMNTK-Ttds-K(Palmitoyl)-CONH$_2$ |
| 60 | OXM317 | HsQGTFTSDYSKYLDSRRAQDFVQWLMNTK-γE-C$_4$-CONH$_2$ |
| 61 | OXM318 | HsQGTFTSDYSKYLDSEAAQDFVQWLMNTK-γE-C$_4$-CONH$_2$ |
| 62 | OXM319 | HαQGTFTSDYSKYLDSEAAQDFVQWLMNTKC$_7$-CONH$_2$ |
| 63 | OXM321 | HsQGTFTSDYSKYLDSEAAQDFVQWLMNTKRNRNNIA-γE-C$_4$-CONH$_2$ |
| 64 | OXM323 | HsQGTFTSDYSKYLDSEAAQDFVQWLMNTKR-C$_7$-CONH$_2$ |
| 65 | OXM325 | HsQGTFTSDYSKYLDSEAAQDFVQWLMNTKRNRNNIAC$_7$-COOH |
| 66 | OXM327 | HαQGTFTSDYSKYLDSERAQDFVQWLMNTKC$_7$-CONH$_2$ |
| 67 | OXM329 | HαQGTFTSDYSKYLDSRRAQDFVQWLMNTK-γE-C$_4$-COOH |

TABLE 3-continued

OXM Peptide Analogs

| SEQ ID NO. | Name | Structure |
|---|---|---|
| 68 | OXM330 | HsQGTFTSDYSKYLDSEAAQDFVQWLMNTKRNRNNIA-γE-K(Palmitoyl)-CONH$_2$ |
| 69 | OXM345 | HsQGTFTSDYSKYLDSRRAQDFVQWLMNTK-γE-γE-C$_4$-COOH |
| 70 | OXM355 | HsQGTFTSDYSSYLDSRRAQDFVQWLMNTK-γE-C$_4$-COOH |
| 71 | OXM357 | HsQGTFTSDYSKYLDSRAAQDFVQWLMNTK-γE-C$_4$-COOH |
| 72 | OXM359 | HsQGTFTSDYSSYLDSRRAQDFVQWLMNTK-γE-C$_7$-COOH |
| 73 | OXM361 | HsQGTFTSDYSKYLDSRAAQDFVQWLMNTK-γE-C$_7$-COOH |
| 74 | OXM373 | HsQGTFTSDYSKYLDERRAQDFVQWLMNTK-γE-C$_4$-COOH |
| 75 | OXM374 | HsQGTFTSDYSKYLDERRAQDFVQWLMNTK-γE-C$_7$-COOH |
| 76 | OXM380 | HsQGTFTSDYSKYLDSRRAQDFVQWLMNTK-γE-γE-C$_7$-COOH |
| 77 | OXM381 | HsQGTFTSDYSKYLDSRRAQDFVQWLMNTK-γE-γE-C$_9$-COOH |
| 78 | OXM383 | Hα QGTFTSDYSKYLDSRRAQDFVQWLMNTK-γE-γE-C$_7$-COOH |
| 79 | OXM388 | H-Acb-QGTFTSDYSKYLDSRRAQDFVQWLMNTK-γE-γE-C$_7$-COOH |
| 80 | OXM392 | HsQGTFTSDYSKYLDERRAKDFVQWLMNTK-γE-γE-C$_{10}$-COOH (lactam bridge between E and K) |
| 81 | OXM395 | Hα QGTFTSDYSKYLDERRAKDFVQWLMNTK-γE-γE-C$_{10}$-COOH (lactam bridge between E and K) |
| 82 | OXM398 | H-Acb-QGTFTSDYSKYLDERRAKDFVQWLMNTK-γE-γE-C$_{10}$-COOH (lactam bridge between E and K) |
| 83 | OXM399 | HsQGTFTSDYSKYLDSRRAQDFVQWLMNTK-γE-γE-C$_{10}$-COOH |
| 84 | OXM400 | Hα QGTFTSDYSKYLDSRRAQDFVQWLMNTK-γE-γE-C$_{10}$-COOH |
| 85 | OXM401 | H-Acb-QGTFTSDYSKYLDSRRAQDFVQWLMNTK-γE-γE-C$_{10}$-COOH |
| 86 | OXM404 | HsQGTFTSDYSKYLDSRRAQDFVQWLMNTK-γE-γE-K(yE-palmitoyl)-CONH$_2$ |
| 87 | OXM406 | HsQGTFTSDYSKYLDERRAQDFVQWLMNTK-γE-YE-C$_{10}$-CONH$_2$ |
| 88 | OXM407 | HsQGTFTSDYSKYLDSRRAK(γE-palmitoyl)DFVQWLMNTK-yEyE-CONH$_2$ |
| 89 | OXM408 | HsQGTFTSDYSKYLDSRRAK(γE-γE-palmitoyl)DFVQWLMNTK-γE-CONH$_2$ |
| 90 | OXM409 | HsQGTFTSDK(γE-γE-palmitoyl)SKYLDSRRAQDFVQWLMNTK-CONH$_2$ |
| 91 | OXM410 | HsQGTFTSDYSKYLDERRAK(γE-γE-palmitoyl)DEVQWLMNTK-CONH$_2$ |
| 92 | OXM411 | HsQGTFTSDK(γE-γE-palmitoyl)SKYLDERRAQDFVQWLMNTK-CONH$_2$ |
| 93 | OXM412 | HsQGTFTSDYSKYLDSRRAQDFVQWLMNTK-γE-γE-C$_{11}$-COOH |
| 94 | OXM413 | Ha DGTFTSDYSKYLDSRRAQDFVK(DOTA)WLmNTK-γE-γE-C$_{10}$-CONH$_2$ |
| 95 | OXM414 | HsQGTFTSDK(γE-palmitoyl)SKYLDERRAQDFVQWLMNTK-γE-CONH$_2$ |
| 96 | OXM415 | HsQGTFTSDK(palmitoyl)SKYLDERRAQDFVQWLMNTK-γE-γE-CONH$_2$ |

TABLE 3-continued

OXM Peptide Analogs

| SEQ ID NO. | Name | Structure |
|---|---|---|
| 97 | OXM416 | H$\alpha$QGTFTSDK($\gamma$E-$\gamma$E-palmitoyl)SKYLDERRAQDFVQWLMNTK-CONH$_2$ |
| 98 | OXM417 | H-Acb-QGTFTSDK($\gamma$E-$\gamma$E-palmitoyl)SKYLDERRAQDFVQWLMNTK-CONH$_2$ |
| 99 | OXM418 | H$s$QGTFTSDK($\gamma$E-$\gamma$E-palmitoyl)SKYLD$a$RRAQDFVQWLMNTK-$\gamma$E-CONH$_2$ |
| 100 | OXM419 | H$\alpha$QGTFTSDYSKYLDSRRAQDFVQWLMNTK-$\gamma$E-$\gamma$E-K(yE-palmitoyl)-CONH$_2$ |
| 101 | OXM420 | H-Acb-QGTFTSDYSKYLDSRRAQDFVQWLMNTK-$\gamma$E-$\gamma$E-K($\gamma$E-palmitoyl)-CONH$_2$ |
| 102 | OXM421 | H$s$QGTFTSDYSKYLDSRRAQDFVQWLMNTK-$\gamma$E-$\gamma$E-C$_{12}$-COOH |
| 111 | MM102 | H$s$QGTFTSDK($\gamma$E-$\gamma$E-palmitoyl)SKYLD$\alpha$RRAQDFVQWLMNTE-$\gamma$E-CONH$_2$ |
| 112 | MM103 | H$s$QGTFTSDK($\gamma$E-$\gamma$E-palmitoyl)SKYLD$\alpha$RRAQDFVQWLMNTk-$\gamma$E-CONH$_2$ |
| 113 | MM111 | H$s$QGTFTSDK(yE-$\gamma$E-palmitoyl)SKYLDERRAQDFVQWLMNTK-yE-CONH$_2$ |
| 114 | MM113 | H$s$QGTFTSDK($\gamma$E-$\gamma$E-palmitoyl)SKYLD$\alpha$RRAQDFVQWLMNTE-$\gamma$E-CONH$_2$ |
| 115 | MM114 | H$s$QGTFTSDK(E-E-palmitoyl)SKYLDERRAQDFVQWLMNTK-$\gamma$E-CONH$_2$ |
| 116 | MM115 | H$s$QGTFTSDK(R-R-palmitoyl)SKYLDERRAQDFVQWLMNTK-$\gamma$E-CONH$_2$ |
| 117 | MM116 | H$s$QGTFTSDK(X-X-palmitoyl)SKYLDERRAQDFVQWLMNTK-$\gamma$E-CONH$_2$ |
| 118 | MM117 | H$s$QGTFTSDK(e-e-palmitoyl)SKYLDERRAQDFVQWLMNTK-$\gamma$E-CONH$_2$ |
| 119 | MM121 | H$s$QGTFTSDK(yE-$\gamma$E-myristoyl)SKYLD$\alpha$RRAQDFVQWLMNTK-$\gamma$E-CONH$_2$ |
| 120 | MM127 | H$s$QGTFTSDK(yE-$\gamma$E-palmitoyl)SKYLD$\alpha$RAAQDFVQWLMDTK-$\gamma$E-CONH$_2$ |
| 121 | MM132 | H$s$QGTFTSDK(yE-$\gamma$E-stearoyl)SKYLD$\alpha$RRAQDFVQWLMNTK-$\gamma$E-CONH$_2$ |

$\alpha$ = $\alpha$-aminoisobutyric acid (Aib); s = D-Ser; n = L-norleucine (Nle), o = O-methyl-homoserine; m = methionine sulfoxide; H2 = desamino-His ($\Delta$NH2-H); Acx = 1-Amino-1-cyclohexane carboxylic acid; Abu = $\alpha$-aminobutyric acid; D-Abu = D-$\alpha$-aminobutyric acid; Nva = Aminovaleric acid; Cpa = $\beta$-cyclopropyl-alanine; Prg = propargylglycine; Alg = Allylglycine; 2-Cha = 2-Amino-2-cyclohexyl-propanoic acid; D-tbg = D-tertbutylglycine; Vg = Vinylglycine; Acp = 1-Amino-1-cyclopropane carboxylic acid; Acb = 1-Amino-1-cyclobutane carboxylic acid; Acpe = 1-Amino-1-cyclopentane carboxylic acid;
k = D-lys; e = D-Glu; X = homocysteic acid; $\gamma$e = D-gamma glutamic acid;
$C_1$ = Cys(mPEG)5 kDa;
$C_2$ = Cys(mPEG)20 kDa;
$C_3$ = Cys(mPEG)$_2$40 kDa, each corresponding to a cysteine residue PEGylated via the side-chain thiol with linear methoxyPEG (mPEG) or branched mPEG1[(mPEG)2] of the indicated MW;
$C_4$ = Cys(cholest-5-en-3-yl{[(2R)-3-amino-2-(amino)-3-oxopropyl]thio}acetate);
$C_5$ = Cys(CH$_2$CONH$_2$), corresponding to a cysteine residue in which the side-chain thiol was reacted with iodoacetamide;
$C_6$ = Cys(mPEG)$_2$60 kDa, each corresponding to a cysteine residue PEGylated via the side-chain thiol with linear methoxyPEG (mPEG) or branched mPEG2mPEG [(mPEG)$_2$] of the indicated MW;
$C_7$= Cys(cholest-5-en-3-yl 1-{[(2R)-3-amino-2-(amino)-3-oxopropyl]thio}-2-oxo-6,9,12,15-tetraoxa-3-azaoctadecan-18-oate]) or Cys(Oxa4-cholesterol));
$C_8$= Cys(N-ethylmaleimidyl).
$C_9$ = S-{1-[46-(cholest-5-en-3-yloxy)-3,43,46-trioxo-7,10,13,16,19,22,25,28,31,34,37,40-dodecaoxa-4,44-diazahexatetracont-1-yl]-2,5-dioxopyrrolidin-3-yl}-L-cysteine or Cys (maloxa$_{12}$-cholesterol)
$C_{10}$ = S-[42-(cholest-5-en-3-yloxy)-2,42-dioxo-6,9,12,15,18,21,24,27,30,33,36,39-dodecaoxa-3-azadotetracont-1-yl]-L-cysteine or Cys (oxa$_{12}$-cholesterol)

TABLE 3-continued

OXM Peptide Analogs

SEQ
ID
NO.  Name      Structure

C11 = S-[78-(cholest-5-en-3-yloxy)-2,78-dioxo-
6,9,12,15,18,21,24,27,30,33,36,39,42,45,48,51,54,57,60,63,66,69,72,75-tetra-
cosaoxa-3-azaoctaheptacont-1-yl]-L-cysteine or Cys (oxa24-cholesterol)
C12 = S-[38-(cholest-5-en-3-yloxy)-2-oxo-6,9,12,15,18,21,24,27,30,33,36-undecaoxa-
3-azaoctatriacont-1-yl]-L-cysteine or Cys (oxa12-O-cholesterol)
Ttds = 1-amino-4,7,10-trioxa-13-tridecanamine succinimic acid
yE = gamma glutamic acid
palmitoyl = C16 fatty acid residue
myristoyl = C14 fatty acid residue
stearoyl = C18 fatty acid residue

Example 7

The ability of GLP-1R/GCGR co-agonists to reduce body weight and food intake and improve glycemic control is demonstrated.

We initially screened peptides in fluorescence cell based assays that measure production of cyclic-AMP (cAMP), using CHO cell lines stably expressing either recombinant human GLP-1R or human GCGR. Determination of Mouse and human GLP-1R and GCGR Agonist Activity was essentially as follows. CHO cells stably expressing mouse or human GLP-1R or GCGR were grown in Iscove's Modified Dulbecco's Medium (IMDM), 10% FBS, 1 mM L-glutamine, penicillin-streptomycin (100 µ/mL) and 750 µg G418/mL for three-four days before harvesting using Enzymefree Dissociation Media (EFDM, Specialty Media). To determine GLP-1R and GCGR activity, OXM and OXM-Q3E were diluted in assay buffer and were incubated with cells in the absence or presence of 10% mouse plasma, respectively, for 30 min at room temperature. The assay was terminated with the addition of the LANCE kit Detection buffer as per the manufacturer's instructions. The plates were held an additional hour at room temperature, then increasing cAMP levels were detected by a decrease in TR-FRET signal as measured in an EnVision counter (PerkinElmer) in comparison to a standard curve of cAMP as per the manufacturer's instructions. Data were analyzed using the linear and non-linear regression analysis software, GraphPad Prism.

Evaluation of the utility of a dual GLP-1R/GCGR co-agonists (OXM mimetic) versus a GLP-1R selective agonist (GLP-1 mimetic) was as follows. First, in order to evaluate the therapeutic utility of a dual GLP-1R/GCGR agonist (OXM mimetic), a matched peptide that was selective for only the GLP-1 receptor (GLP-1 mimetic), yet differs from native OXM by only one amino acid was identified. This peptide differed from native OXM by having a Glutamic acid (E) residue at position 3 instead of Glutamine (Q). A second GLP-1 mimetic was identified that had an aspartic acid residue (D) in place of the Q. The efficacy of the GLP-1 mimetic and the OXM mimetic in improving metabolic control in rodents were compared. These peptides and human OXM were synthesized and purified by GL Biochem (Shanghai) Ltd.

In Table 4, the in vitro potencies and receptor binding affinities of native OXM and OXM-Q3E and OXM-Q3D peptides. Mutation of the third residue from the neutral Q to an acidic residue, e.g., D or E significantly reduces the potency of native oxyntomodulin to bind the glucagon receptor, while having minimal effect on the potency for the GLP-1 receptor.

TABLE 4

| Peptide | GLP-1R $IC_{50}$ (nM) | GLP-1R $EC_{50}$ (nM) | GCGR $IC_{50}$ (nM) | GCGR $EC_{50}$ (nM) | % Activation of GCGR | Selectivity |
|---|---|---|---|---|---|---|
| OXM | 93 | 9.2 | 7.7 | 0.6 | 87 | +/+ |
| OXM-Q3E | 237 | 12.4 | ND | 1635 | 17 | +/0 |
| OXM-Q3D | Not tested | 2.3 | Not tested | 3398 | 1 | +/0 |

We further evaluated the ability of native OXM and OXM-Q3E (GLP-1-mimetic) to interact with the GCGR in vivo, both in an ex vivo glycogenolysis study and an in vivo GCGR receptor occupancy assay. As demonstration of in vivo efficacy for peptides is often confounded by inadequate pharmacokinetic properties, the perfused liver assay offers an alternative ex vivo method of assessing test peptides for activity in the functioning organ of interest.

Animals for the In Vivo Assays:

Lean or diet-induced obese 10-12-week-old male C57BL/6 mice were purchased from Taconic Farms (Germantown, N.Y.) and housed in individual Tecniplast cages in a conventional SPF facility. Mice were maintained on either regular chow (Teklad 7012: 13.4% kcal from fat; Harlan Teklad) or high fat diet (D12492: 60% kcal from fat; Research Diets, Inc.) with ad libitum access to water in a 12-h light/12-h dark cycle unless stated otherwise. Intraperitoneal glucose tolerance test. Male C57BL/6N mice were distributed by weight into treatment groups (n=6/group). On the morning of study, food was removed and mice were s.c. administered with vehicle (sterile water) OXM or OXM-Q3E at 0.01, 0.03, 0.1, 0.3, 1 or 3 mg/kg. 10 min prior the glucose challenge. Blood glucose concentrations were determined at T=−10 min and T=0 min (baseline). Mice were then immediately challenged, intraperitoneally, with D-glucose (2 g/kg). One group of vehicle-treated mice was challenged with 0.9% saline as a negative control. Blood glucose levels were determined from tail bleeds taken at 20, 40 and 60 min after D-glucose challenge. The blood glucose excursion profile from T=0 to T=60 min was used to integrate the area under the curve (AUC) for each treatment. Percent inhibition values for each treatment were generated from the AUC data normalized to the saline-challenged controls. Areas under the curve (AUC)

for glucose (AUC glucose) was calculated using the trapezoidal method. Statistics. Statistical analysis was done using unpaired 2-tailed Student's t test. P values<0.05 were reported as significant.

Liver Glycogenolysis Assay.

Humanized GCGR mice (C57B/6N) were anesthetized (Nembutal IP, 50 mg/kg) in the middle of the dark cycle. The portal vein was then cannulated and the liver was excised and perfused with a preoxygenated Krebs-Henseleit bicarbonate buffered solution for 5-10 minutes which initially was not recirculated to wash out any endogenous substrates. The liver was then placed into a 20 mm NMR tube and the initial Krebs solution was exchanged for a Krebs-BSA perfusate (approx. 72 ml, 2.5% BSA), which was recirculated. $^{31}$P NMR spectroscopy was performed initially to examine the ATP and inorganic phosphate (Pi) levels to assess hepatic viability. A $^{13}$C NMR-visible pool of glycogen was then created by the addition of the gluconeogenic substrate [2-$^{13}$C] Pyruvate and ammonium chloride (~7 mM and 1 mM, respectively) to the perfusate, and the amount of $^{13}$C glycogen contained in the liver was monitored in real time via the C1 resonance of the glucosyl units in glycogen. After 45 minutes, OXM, OXM-Q3E, glucagon or vehicle was perfused and the subsequent response of glycogen levels was used to assess GCGR activation (Bergans et al., NMR Biomed. 16: 36-46, (2003)). Glucose dependent insulin secretion (GDIS). To measure GDIS, mouse pancreatic islets were isolated by the collagenase method using the procedure of pancreatic duct cannulation and density gradient purification (Mu et al., Diabetes 55: 1695-704, (2006)) and were incubated with 2 or 16 mmol/L glucose. Insulin was measured in aliquots of the incubation buffer by enzyme linked immunosorbent assay with a commercial kit (ALPCO diagnostics, Windham, N.H.). Animal study protocols were reviewed and approved by the Merck Research Laboratories Institutional Animal Care and Use Committee in Rahway, N.J.

Figure 1B:
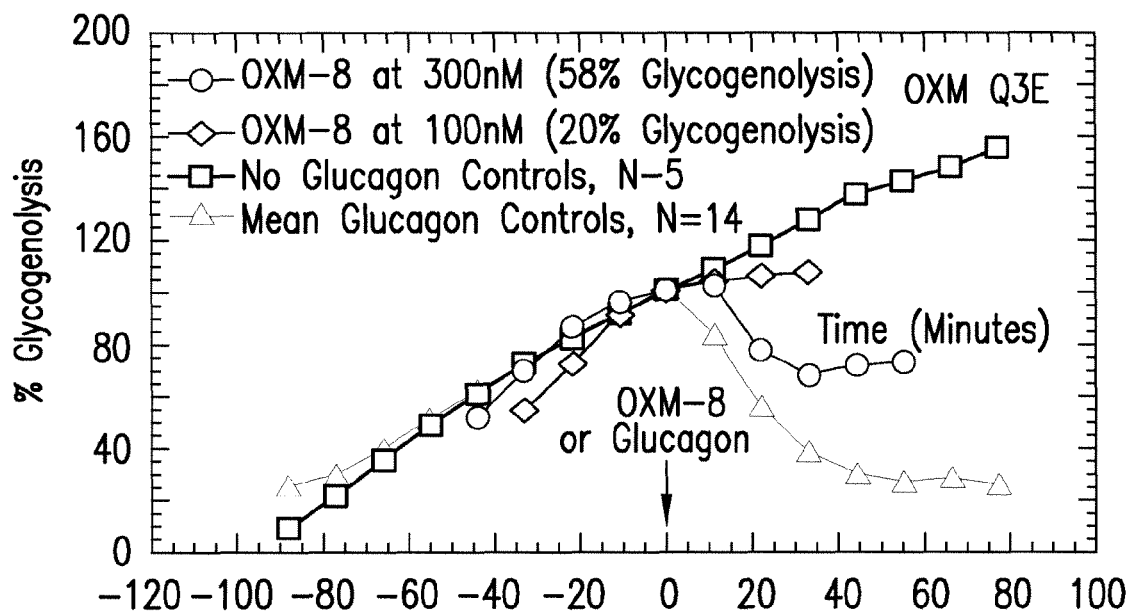

$^{13}$C-NMR spectroscopy was used to non-invasively monitor glycogen and glucose levels in response to acute treatment with novel oxyntomodulin analogs in real time. Mice expressing human GCGR were anesthetized (Nembutal IP, 50 mg/kg) at approximately the middle of the dark cycle. The portal vein was then cannulated and tied off and the liver was excised. The liver was then placed into a 20 mm NMR tube and the initial Krebs solution was exchanged for a Krebs-BSA perfusate, which was recirculated. $^{31}$P NMR spectroscopy was performed initially to examine the ATP and inorganic phosphate (Pi) levels in the liver which can be used to assess hepatic viability. A $^{13}$C NMR-visible pool of glycogen was then created by the addition of the gluconeogenic substrate [2-$^{13}$C] Pyruvate+NH$_4$Cl and the amount of glycogen contained in the liver was monitored in real time via the C1 resonance of the glucosyl units in glycogen. After approximately 45 minutes, OXM or an OXM peptide analog was infused and the subsequent response of glycogen levels was used to assess human GCGR activation. The area of the C1 resonance of the glucosyl units in glycogen is plotted over time in FIG. 1 for livers that received either the OXM peptide analogs, 50 pM glucagon, or media. As can be seen below, native OXM induces glycogenolysis in a dose dependent fashion and induces full glycogenolysis at 1.5 nM and has an approximate EC$_{50}$ of 0.5 nM, in comparison, OXM-Q3E induced only about 58% at 300 nM, consistent with its poor GCGR agonist potency.

Figure 2:
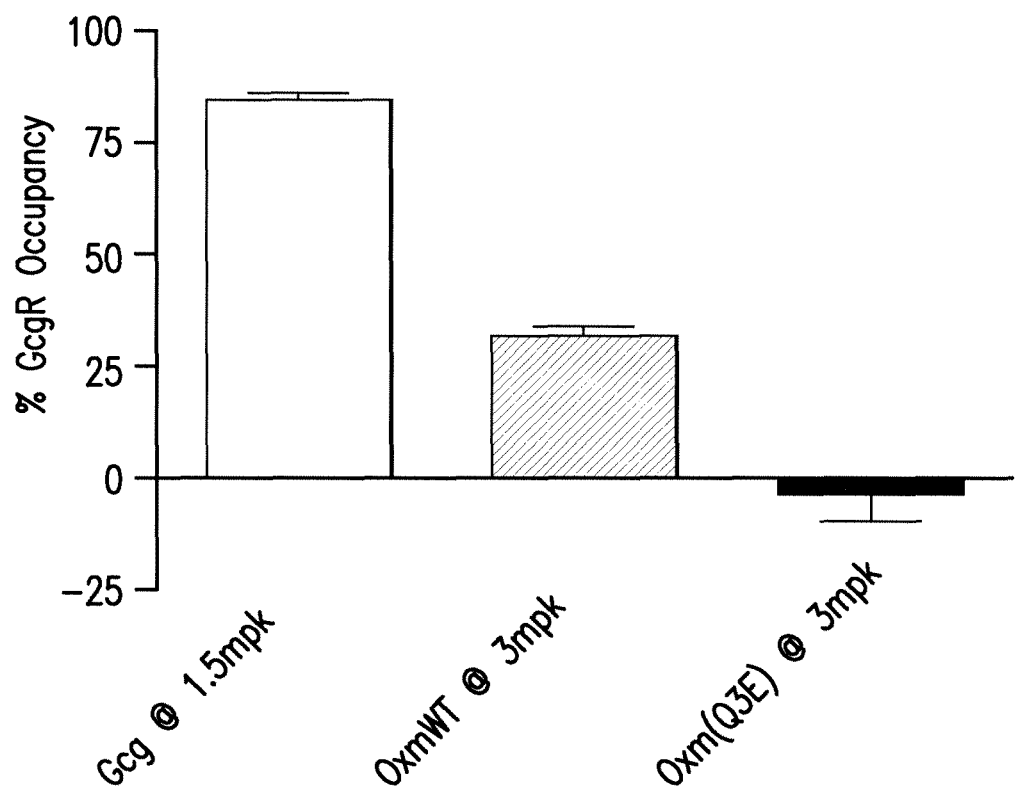
FIG. 2 shows the results of an in vivo GCG Receptor occupancy experiment showing that glucagon (GCG) at 1.5 mpk gave 84% GCGR occupancy and 3 mpk OXM gave 31% GCGR occupancy but that OXM-Q3E gave 0% GCGR occupancy.

Given the ability of OXM to stimulate a robust glycogenolysis response, we further examined the in vivo GCGR receptor occupancy of OXM and OXM-Q3E in a competition assay in wild-type mice. Three cohorts of mice were dosed with either vehicle (total counts), vehicle and cold glucagon (non-specific binding), or OXM-Q3E subcutaneously. About 15 minutes post dose, $^{125}$I-glucagon was administered intra-venously and about 15 minutes later, the liver was collected and total radioactivity assayed. As shown in FIG. 2, glucagon (GCG) at 1.5 mpk gave 84% GCGR occupancy, 3 mpk OXM gave 31% GCGR occupancy, and OXM-Q3E gave 0% GCGR occupancy.

Using the matched peptides, OXM, OXM-Q3E, we investigated both acute and chronic pharmacological effects of co-agonism of both receptors in a chronic hyperglycemic clamp and a chronic food intake (FI) and body weight (BW) study (Table 5) and in an acute intraperitoneal glucose tolerance test (IPGTT, FIG. 3). While both peptides effectively improved glucose tolerance, OXM-Q3E out-performed native OXM in reducing glucose excursion in both lean and diet induced obesity (DIO) mouse models. However, the native peptide proved superior at reducing food intake and body weight (ΔBW: −6% for OXM vs −2.4% for OXM-Q3E at 5 mg/kg) in DIO mice, an effect attributed to co-agonism of the GCGR. In both acute and chronic paradigms, native OXM did not cause increased glucose excursion.

TABLE 5

Pharmacodynamic endpoints following a 14 day chronic infusion of OXM and OXM-Q3E to evaluate food intake and body weight effects.

| Measurement | Vehicle | OXM 0.5 mg/kg | OXM 1.5 mg/kg | OXM 5 mg/kg | OXM-Q3E 0.5 mg/kg | OXM-Q3E 1.5 mg/kg | OXM-Q3E 5 mg/kg |
|---|---|---|---|---|---|---|---|
| Cumulative weight change (g) | 1.07 | 0.54 | −3.5 | −5.32 | −0.21 | −1.27 | −0.21 |
| Cumulative food intake change (kcal) | 228 | 223 | 206 | 199 | 215 | 213 | 207 |

Hyperglycemic Clamp Study.

DIO mice (16 wk on high fat diet) were anesthetized with xylazine and ketamine and catheterized through the right internal jugular vein 3 days before the in vivo studies. 25% glucose was infused and adjusted for the duration of the experiment to maintain hyperglycemia. Due to the short half-life of the peptides (both are rapidly inactivated by dipeptidyl peptidase IV and renally cleared (Zhu et al., J. Biol. Chem. 278: 22418-23, (2003))), vehicle, OXM (~16 µg/kg/min) and OXM-Q3E (~16 µg/kg/min) were infused intravenously during the last 60 minutes of the study. The venous catheter was used for infusion, and blood samples were collected from the tail vein. Each animal was monitored for food intake and weight gain after surgery to ensure complete recovery. Hyperglycemic clamps were performed in conscious, unrestrained, catheterized mice as previously described (Pocai et al., Nature. 43: 1026-31, (2005)). Briefly, plasma glucose was measured by OneTouch glucometer every 10 minutes during the 2 hour period. Twenty-five percent glucose (D-glucose, Sigma) was infused i.v. and the rate was adjusted periodically to clamp the plasma glucose levels (~20 mM). One hour after the beginning of the infusion, OXM (~16 µg/kg/min), OXM-Q3E (16 µg/kg/min) and vehicle (sterile saline) were administered for the rest of the period. Glucose infusion rate (GIR) was adjusted to body weight.

Figure 3A:
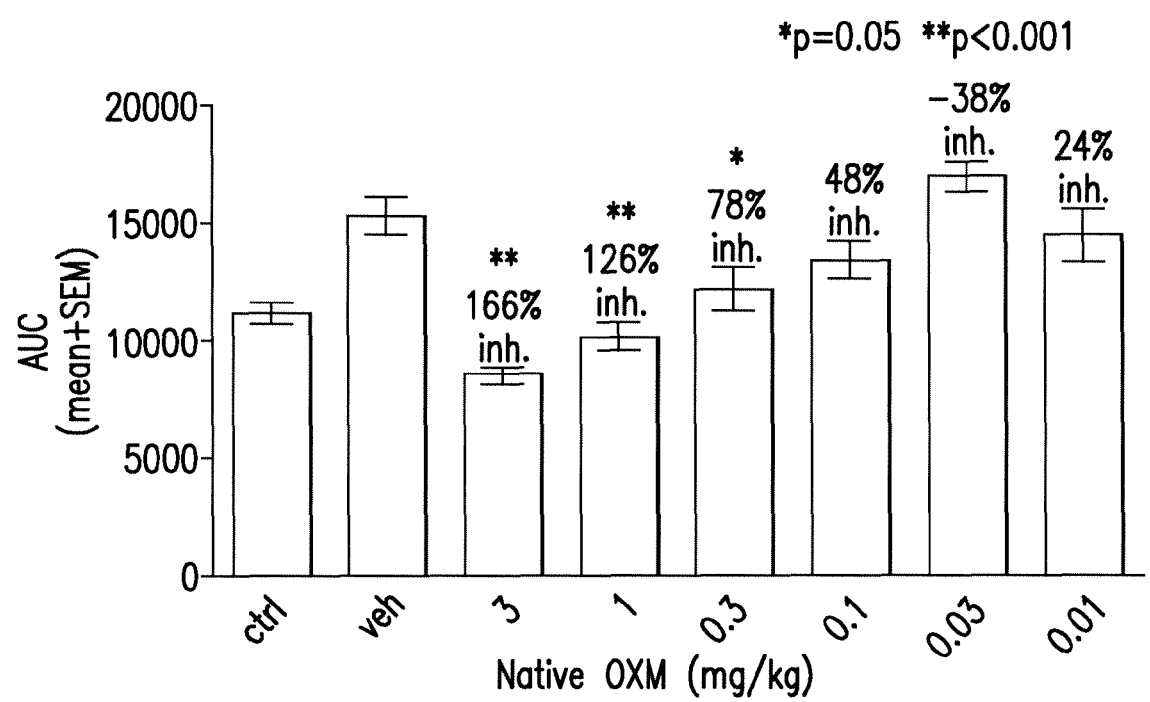
FIGS. 3A and 3B show the blood glucose levels and glucose infusion rates, respectively, in response to OXM and OXM-Q3E.
Figure 3B:
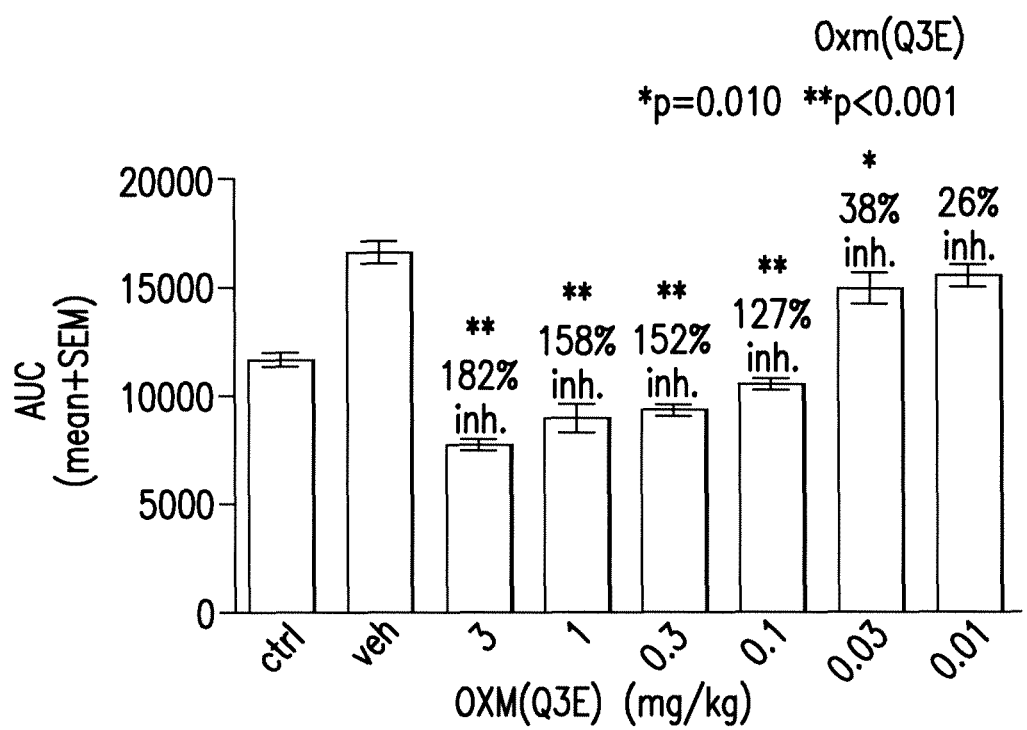

The results of the hyperglycemic clamp assay are shown in FIGS. 3A and 3B. Blood glucose levels were maintained at about 20 mmol/L during the clamp. In OXM-Q3E treated animals, a quick and robust increase in glucose infusion (GIR, glucose infusion rate) was required to maintain hyperglycemia compared with vehicle-treated mice (GIR0-60 55±4 vs 6±2 mg/kg/min; OXM-Q3E vs vehicle; p<0.05). OXM also increased the glucose infusion rate required to maintain hyperglycemia (GIR0-60=40±4 vs 6±2 mg/kg/min; OXM vs vehicle, p<0.05) but the increase in GIR was about 30% lower than that in the OXM-Q3E group (GIR0-60=40±4 vs 55±4 mg/kg/min; OXM vs OXM-Q3E respectively, p<0.05), and the glucose lowering effect was delayed (by about 10 minutes) compared to OXM-Q3E treated mice, *p<0.05 vs vehicle.

Figure 4A:
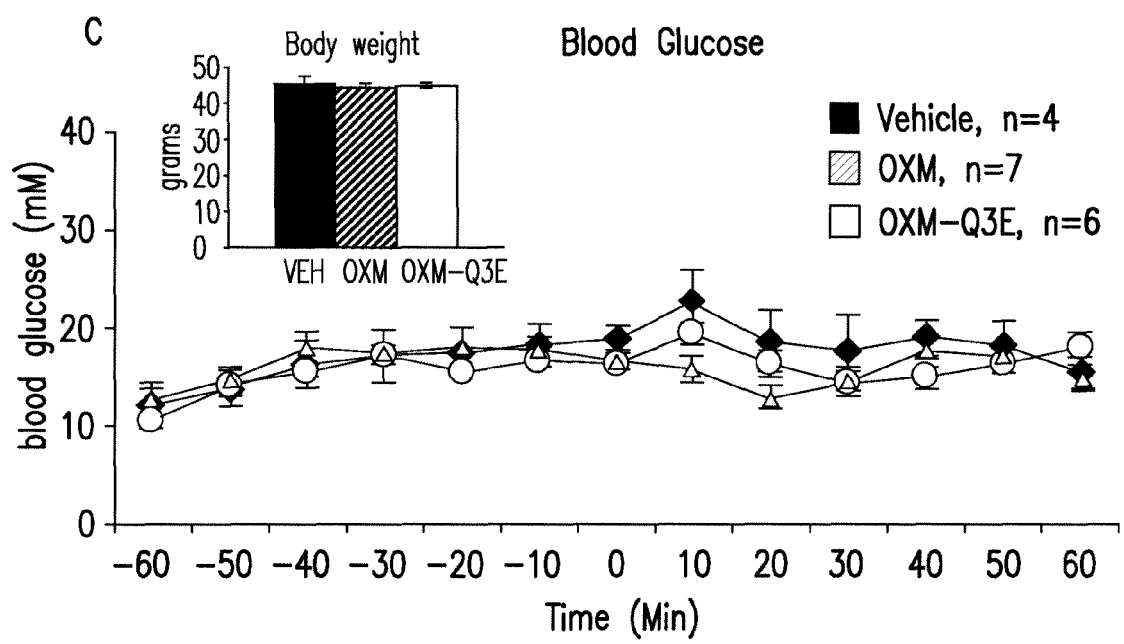
FIGS. 4A and 4B show the results of an intraperitoneal glucose tolerance test (IPGTT) in lean mice for subcutaneous (s.c.) administration of OXM and OXM-Q3E.
Figure 4B:
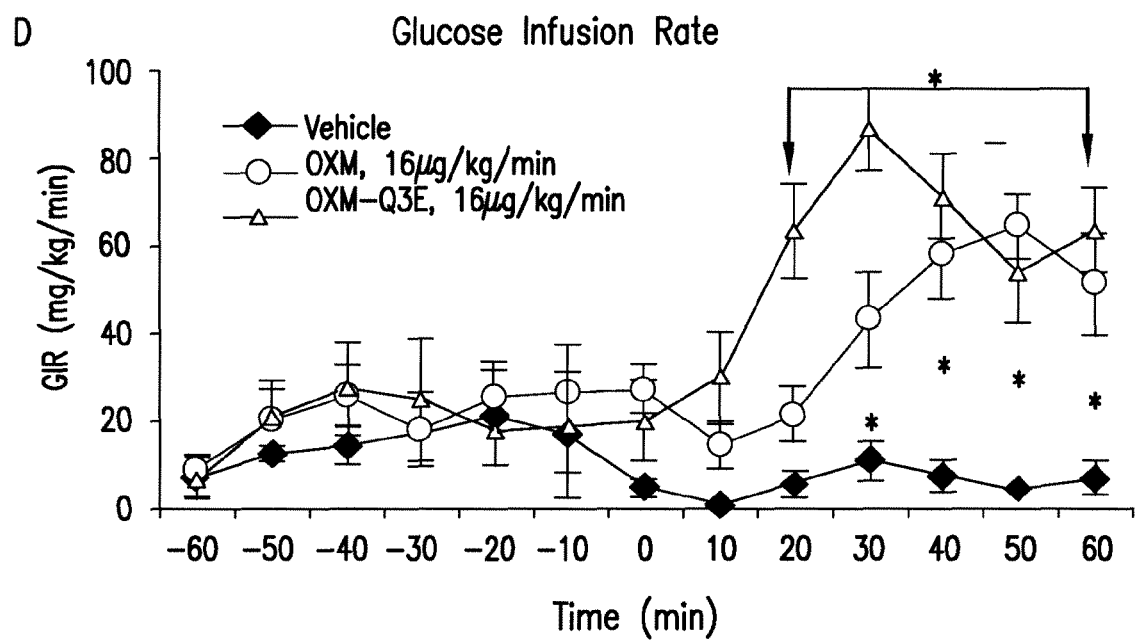

The effect of OXM or OXM-Q3E on glucose excursion in C57BL/6N lean mice was compared. FIGS. 4A and 4B show that both native and OXM peptide analogs reduce glucose excursion. The subcutaneous administration of either peptide, prior to dextrose challenge (Plasma $C_{max}$) in an intraperitoneal glucose tolerance test (IPGTT), significantly reduced blood glucose excursion in a dose-dependent manner. A comparison of the minimal effective dose indicates that OXM-Q3E is about 10-fold more effective at reducing glucose than native peptide (in vivo $EC_{50}$ 0.055 nM and 0.38 nM respectively).

Example 8

Native OXM has an in vivo half-life ($t_{1/2}$) of about 8 to 12 minutes in humans, unsuitable for sustained pharmacological therapy. Therefore, we investigated the addition of bulky substituents to the peptide to reduce renal clearance.

Various molecular weight PEG moieties or N-ethyl maleimide were conjugated to the OXM peptide at various locations throughout the molecule, by conjugation to the side chain of an introduced cysteine residue. Positions that were investigated for conjugation with either Cys-N-ethyl maleimide or a Cys-PEG moiety are underlined in the following amino acid sequence for OXM (SEQ ID NO:1) or placed at the C-terminus of the OXM.

HSQGT FTSDY SKYLDSRRAQDFVQW LMNTK RNRNN IA

Unexpectedly, PEGylation (5 to 80 kDa) appeared to severely diminish the ability of the peptide analog to activate either the GCGR or both GLP-1R and GCGR. In some cases, introduction of an N-ethyl maleimide-capped cysteine residue was sufficient to significantly reduce activity. The results are shown in Table 6).

TABLE 6

| Peptide Analog | Conjugate/Position | GLP-1R EC50 (nM) | GCGR EC50 (nM) | % Activation of GCGR | GCGR + 10% serum (nM), fold shift | Receptor Selectivity |
|---|---|---|---|---|---|---|
| OXM33 | 5K-PEG/$C_{38}$ | 115 | 75.3 | 78 | — | 0/0 |
| OXM34 | 20K-PEG/$C_{38}$ | 195 | 616 | 61 | — | 0/0 |
| OXM35 | 40K-PEG/$C_{38}$ | 716 | 142 | 71 | — | 0/0 |
| OXM67 | 5K-PEG/$C_{38}$ | 5.8 | 138 | 73 | — | +/0 |
| OXM68 | 20K-PEG/$C_{38}$ | 8.3 | 601 | 58 | — | +/0 |
| OXM69 | 40K-PEG/$C_{38}$ | 6 | >1000 | 46 | — | +/0 |
| OXM99 | 40K-PEG/$C_{38}$ | 7.4 | >1000 | 66 | — | +/0 |
| OXM100 | 60K-PEG/$C_{38}$ | 22.5 | >1000 | 22 | — | ~/0 |
| OXM103 | 40K-PEG/$C_{20}$ | 6.2 | 203 | 75 | — | +/0 |
| OXM105 | 40K-PEG/$C_{21}$ | 28.5 | 648 | 21 | — | ~/0 |
| OXM107 | 40K-PEG/$C_{24}$ | 29.7 | >1000 | 30 | — | ~/0 |
| OXM109 | 40K-PEG/$C_{28}$ | 7.6 | >1000 | 65 | — | +/0 |
| OXM113 | 40K-PEG/$C_{38}$ | 93.3 | >1000 | 58 | — | 0/0 |
| OXM121 | 40K-PEG/$C_{11}$ | >125 | ND | — | — | 0/0 |
| OXM124 | 40K-PEG/$C_{12}$ | >100 | ND | — | — | 0/0 |

Example 9

As an alternative to PEGylation, we evaluated several lipidated OXM peptide analogs for improvements in the pharmacokinetic profile.

We initially conjugated the peptides with a cholesterol group via the cysteine side chain and again measured their ability to stimulate cAMP production in GLP-1R and GCGR transfected cell lines. C-terminal conjugation was the most favorable location for conjugation and OXM analogs with low nanomolar receptor potencies were identified. Unexpectedly, analysis of these peptides in the ex vivo liver perfusion glycogenolysis assay indicated that the in vitro GCGR agonist potency was not correctly reflecting GCGR activation in the liver (See OXM70 in FIG. 5). Measurement of agonist potency in 10 to 20% plasma added to the in vitro cell assay revealed a significant "serum shift" that effectively reduced the potency of the molecule by more than >40-fold (See Table 7), suggesting that the cholesteroylated molecules bound to lipid and/or protein in the plasma, reducing the effective concentration.

TABLE 7

In vitro potencies of selected lipidated OXM peptide analogs

| Peptide | Conjugate/Position | GLP-1R EC50 (nM) | GCGR EC50 (nM) | % Activation of GCGR | GCGR + 10% plasma (nM), (fold shift) | Plasma Shifted Selectivity |
|---|---|---|---|---|---|---|
| OXM36 | Cholesterol/$C_{38}$ | 0.1 | 12.1 | 107 | ?? | +/+ |
| OXM70 | Cholesterol/$C_{38}$ | 0.15 | 2.4 | 104 | 169 (70x) | +/0 |
| OXM212 | Cholesterol/$C_{38}$ | 0.6 | 11.3 | 115 | 1034 (92x) | +/0 |
| OXM213 | Cholesterol/$C_{38}$ | 0.3 | 27.6 | 107 | 1209 (44x) | +/0 |
| OXM110 | Palmitoyl/$K_{38}$ | 0.7 | 0.31 | 104 | 6.9 (23x) | +/+ |
| OXM115 | Oxa4-Chol/$C_{38}$ | 0.08 | 0.33 | 100 | 0.64 (2x) | +/+ |
| OXM177 | Palmitoyl/$K_{38}$ | 0.1 | 0.59 | 93 | 3 (5x) | +/+ |
| OXM216 | Oxa4-Chol/$C_{38}$ | 3.1 | 0.63 | 93 | 12 (19x) | +/+ |
| OXM229 | $C_{38}$ Precursor | ? | ? | ? | Not tested | ? |
| OXM208 | $C_{38}$ Precursor | ? | ? | ? | Not tested | ? |
| OXM209 | $C_{38}$ Precursor | ? | ? | ? | Not tested | ? |

Figure 5A:
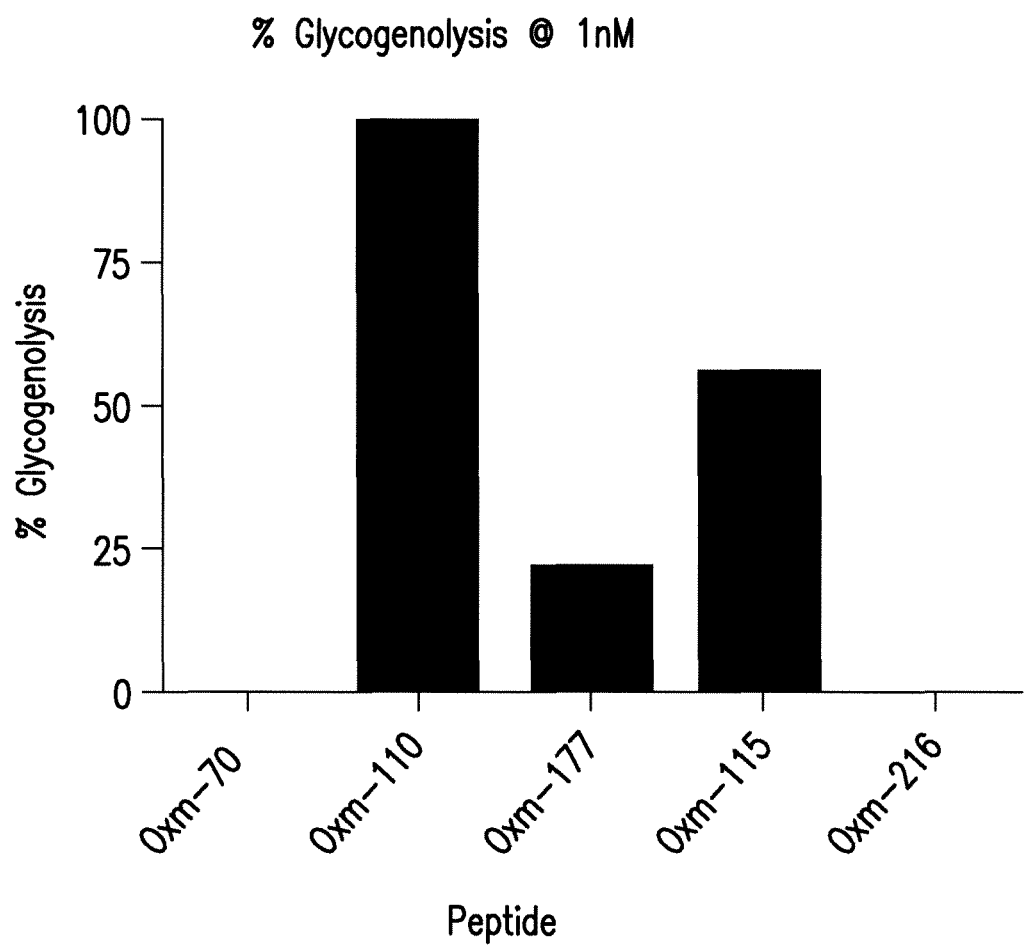
FIG. 5A shows ex vivo measurement of glycogenolysis in perfused liver in the presence of OXM70, OXM110, OXM177, OXM115, and OXM216.
Figure 5B:
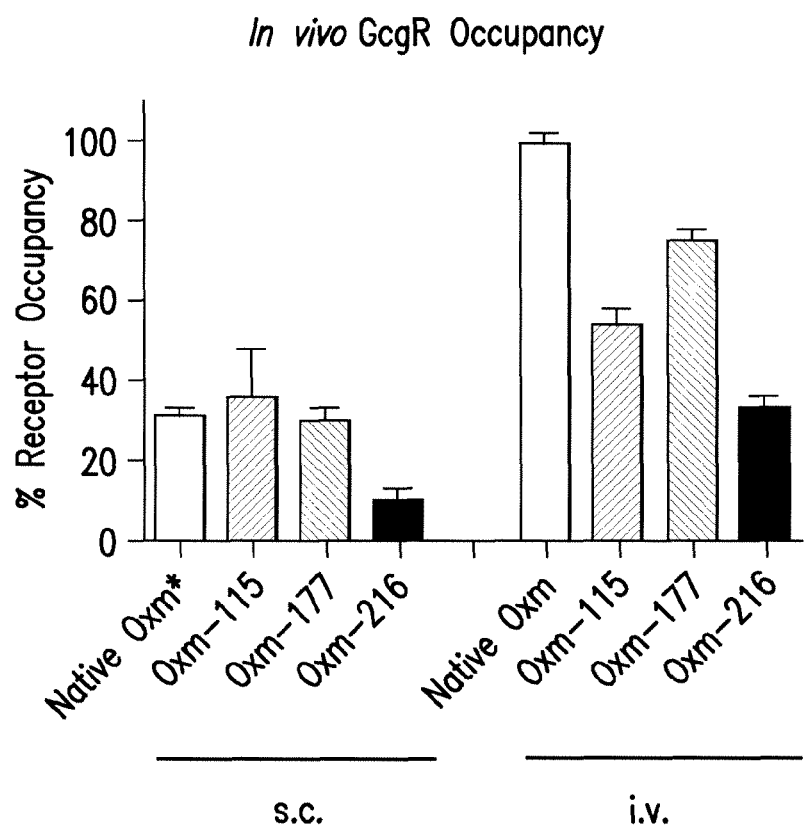
FIG. 5B shows GGCR occupancy following subcutaneous (s.c.) or intravenous (i.v.) administration of the OXM70, OXM110, OXM177, OXM115, and OXM216 compared to native OXM in a competition assay in wild-type mice.

FIG. 5A shows ex vivo measurement of glycogenolysis in perfused liver in the presence of OXM70, OXM110, OXM177, OXM115, and OXM216. FIG. 5B shows GGCR occupancy following subcutaneous (s.c.) or intravenous (i.v.) administration of the OXM70, OXM110, OXM177, OXM115, and OXM216 compared to native OXM in a competition assay in wild-type mice.

Example 10

In order to mitigate the effects of plasma binding on receptor engagement we employed a modified strategy to improve the pharmacokinetics by incorporating a hydrophilic linker between the peptide and the cholesterol group. Addition of a tetra-ethoxy linker (Oxa4) between the cholesterol moiety and the peptide significantly reduced the effect observed above when plasma was added to the cell based assay, i.e., reduced the "serum shift" to as little as 2 fold as shown in Table 8. Furthermore, substituting either aminoisobutyric acid (Aib) or D-Serine (D-Ser) at amino acid position two further improved both GLP-1R and GCGR affinity. We confirmed these in vitro observations in both the ex vivo glycogenolysis assay and the GCG receptor binding assay (See Table 8), obtaining results that confirmed that conjugation of a hydrophilically linked cholesterol group or an acyl chain resulted in identification of molecules that efficiently engaged and activated the GCGR.

the analogs containing either acyl groups or a hydrophilic linker were significantly more efficacious than the other site-specific lipidated OXM analogs in reducing food intake and body weight in this model.

Figure 6A:
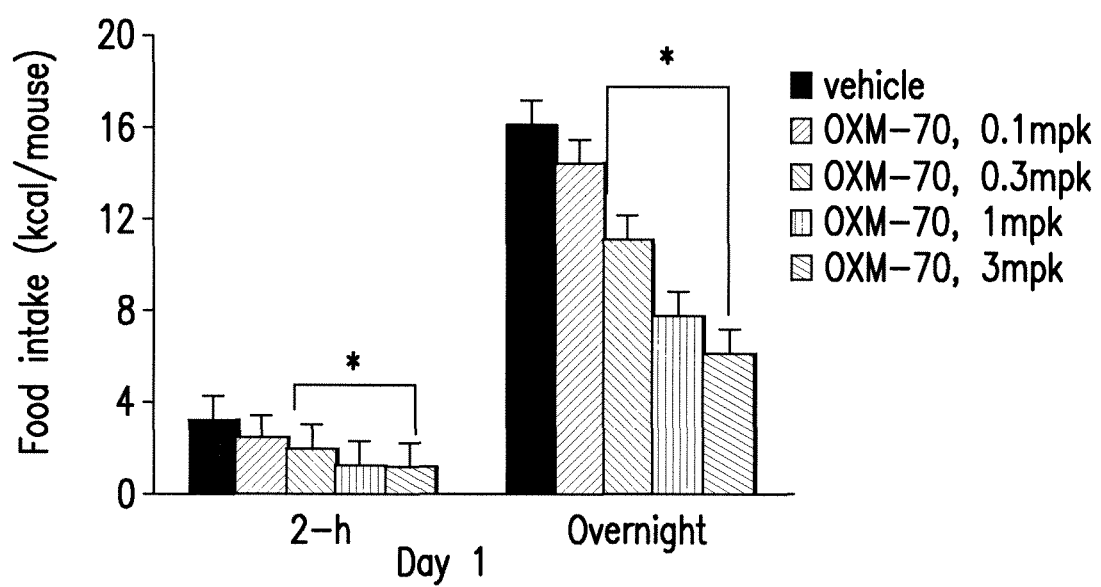
FIGS. 6A and 6B summarize the acute in vivo efficacy of OXM70 on reducing food intake and body weight in established DIO mice. Food intake was measured about two hours and 18 hours later. Body weight changes at 18 hours (overnight) were also measured *P<0.05 vs. vehicle, n=5-6 per group).
Figure 6B:
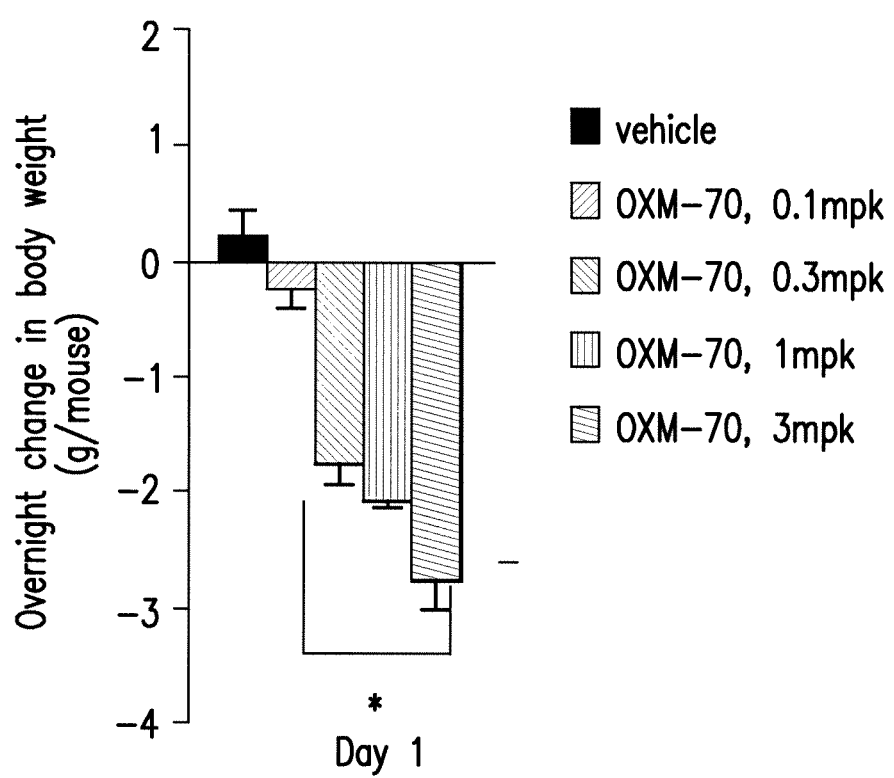
Figure 7A:
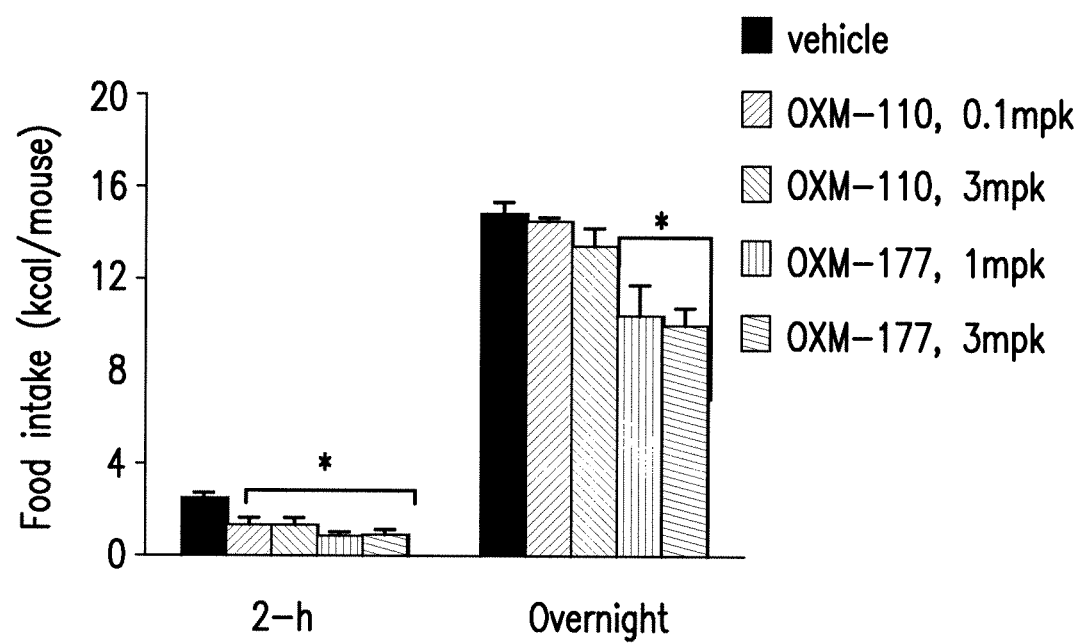
FIGS. 7A and 7B summarize the acute in vivo efficacy of OXM110 and OXM177 on reducing food intake and body weight in established DIO mice. Food intake was measured about two hours and 18 hours later. Body weight changes at 18 hours (overnight) were also measured *P<0.05 vs. vehicle, n=5-6 per group).
Figure 7B:
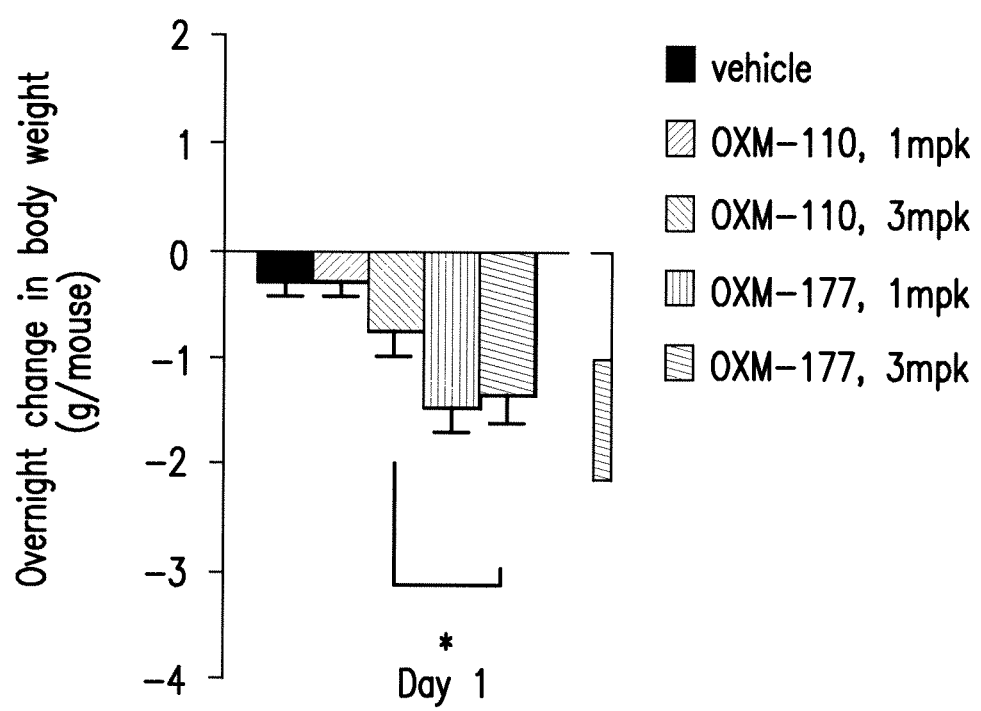
Figure 8A:
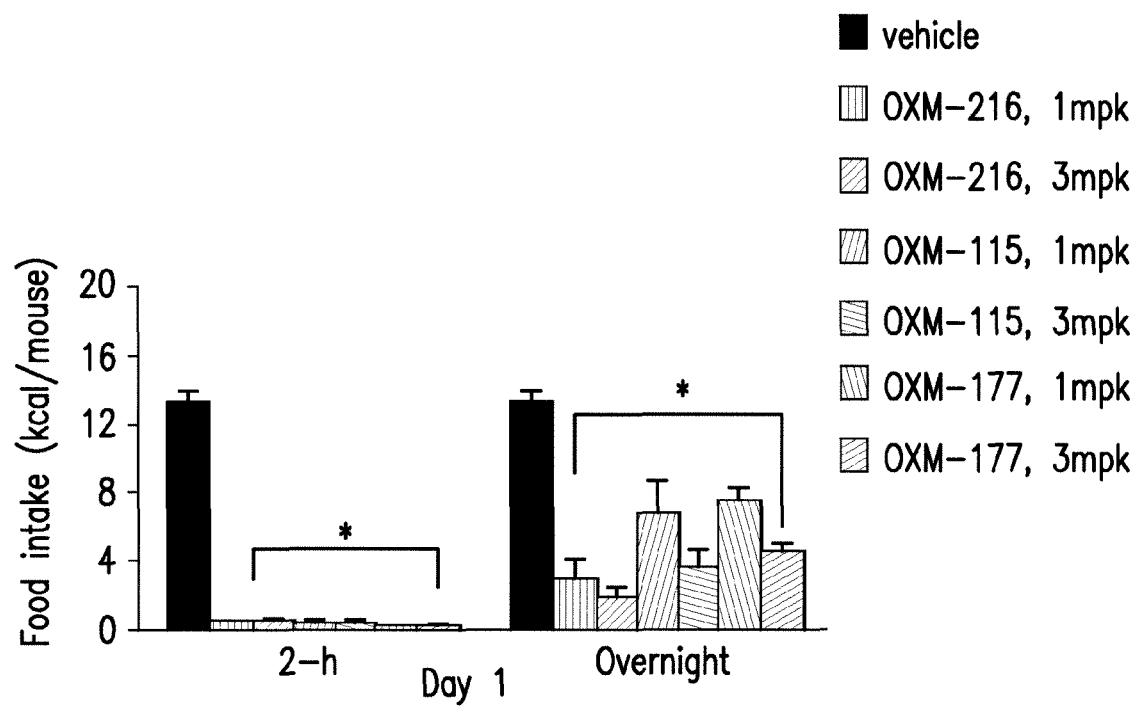
FIGS. 8A and 8B summarize the acute in vivo efficacy of OXM216, OXM115, and OXM177 on reducing food intake and body weight in established DIO mice. Food intake was measured about two hours and 18 hours later. Body weight changes at 18 hours (overnight) were also measured *P<0.05 vs. vehicle, n=5-6 per group).
Figure 8B:
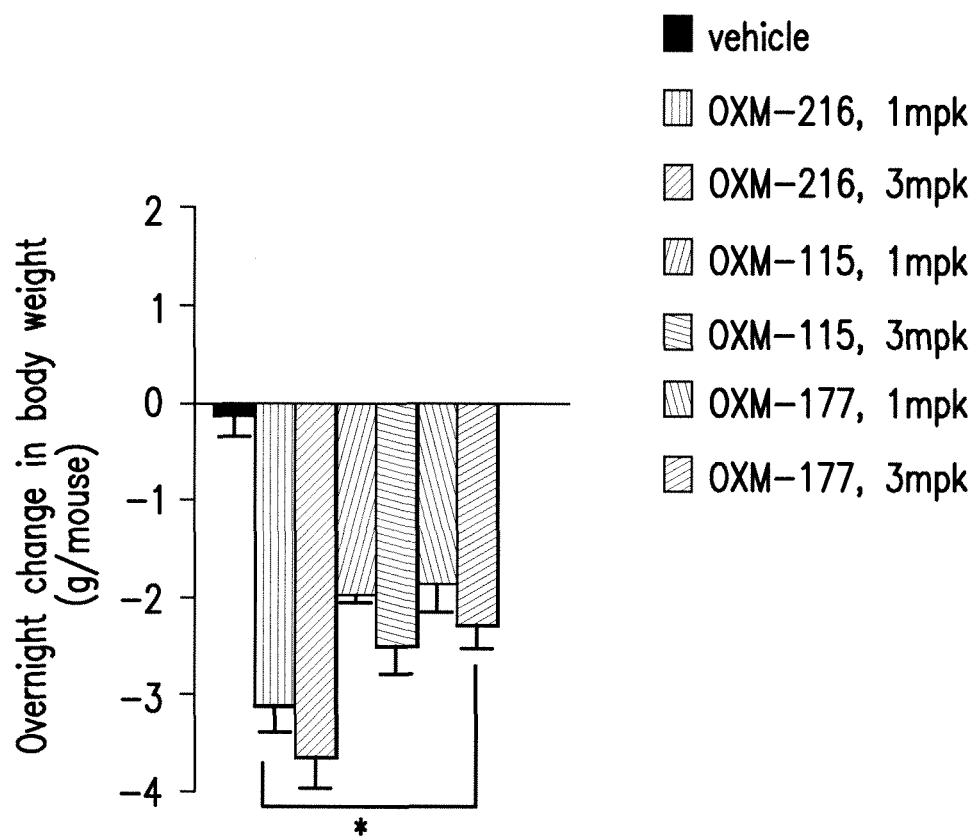

FIGS. 6A and 6B summarize the acute in vivo efficacy of OXM70 on reducing food intake and body weight in established DIO mice. FIGS. 7A and 7B summarize the acute in vivo efficacy of OXM110 and OXM177 on reducing food intake and body weight in established DIO mice. FIGS. 8A and 8B summarizes the acute in vivo efficacy of OXM216, OXM115, and OXM177 on reducing food intake and body weight in established DIO mice. In all three experiments, Ad libitum fed, DIO male C57BL/6 mice (about 51 g each) were weighed and dosed ip with either vehicle (water) or OXM analog OXM70, OXM110, OXM177, OXM216, or OXM115 about 30 minutes prior to the onset of the dark phase. Food intake was measured about two hours and 18 hours later. Body weight changes at 18 hours (overnight) were also measured *P<0.05 vs. vehicle, n=5-6 per group).

Chronic Food Intake & Body Weight Effects

To determine the chronic effects of the analogs on energy and glucose metabolism, studies were performed in an established diet induced obesity (DIO) mouse model. Ad libitum fed male C57BL/6N wild-type mice (n=6 per group, mean body weight ~50 g) were dosed with vehicle, OXM115, OXM177, OXM110 at 3 or 10 mg/kg every other

TABLE 8

Summary of Measurements of GGCR interaction of various lipidated peptides

| Analog | Substitution at position two | Conjugation | % Glycogenolysis | 100% Glycogenolysis | % RO @ 3 mpk s.c. |
|---|---|---|---|---|---|
| Oxm-70 | Aib | Cholesterol | ~0% @ 10 nM | 100% @ 100 nM | ~0 |
| Oxm-110 | D-Ser | Palmitoyl | 100% @ 1 nM | 100% @ 10 nM | Not tested |
| Oxm-177 | Aib | Palmitoyl | 21% @ 1 nM | 100% @ 4 nM | 30(±3) |
| Oxm-115 | D-Ser | Oxa4-Chol | 55% @ 0.3 nM | 100% @ 3 nM | 36(±12) |
| Oxm-216 | Aib | Oxa4-Chol | 0% @ 10 nM | 88% @ 100 nM | 10(±3) |

Figure 9A:
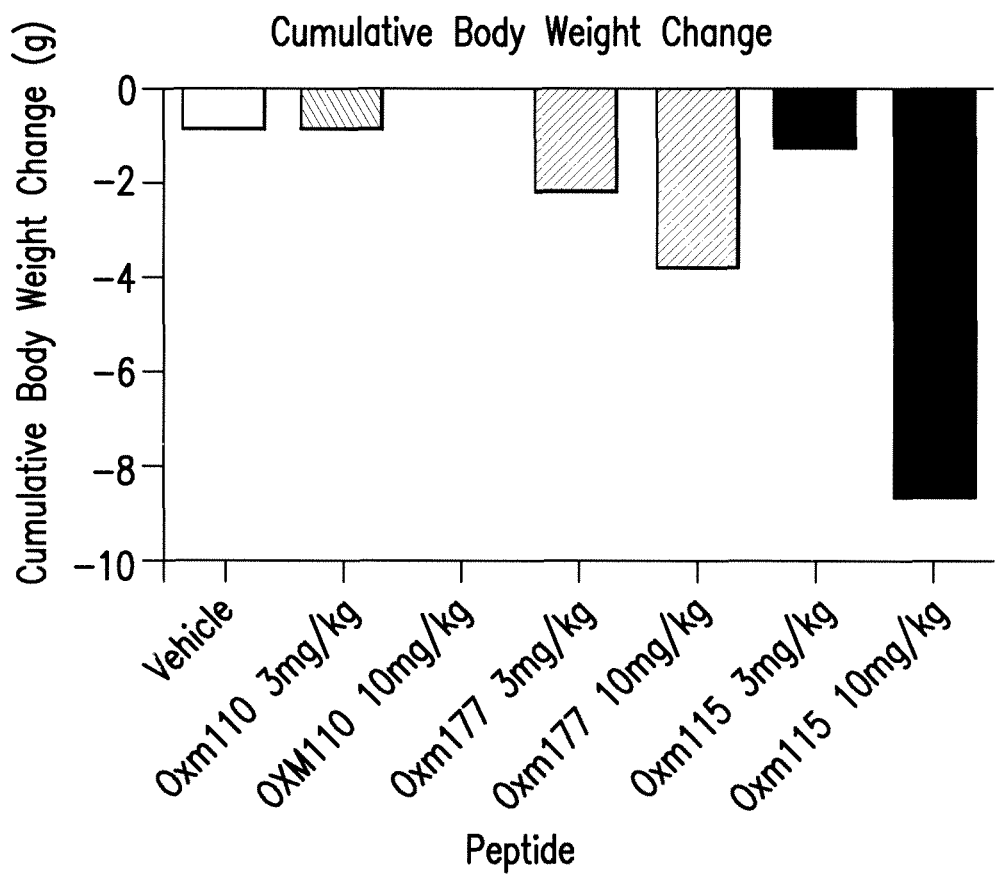
FIGS. 9A-D shows the pharmacological end points of a chronic body weight and food intake study in DIO mice for OXM peptide analogs OXM110, OXM177, and OXM115.
Figure 9B:
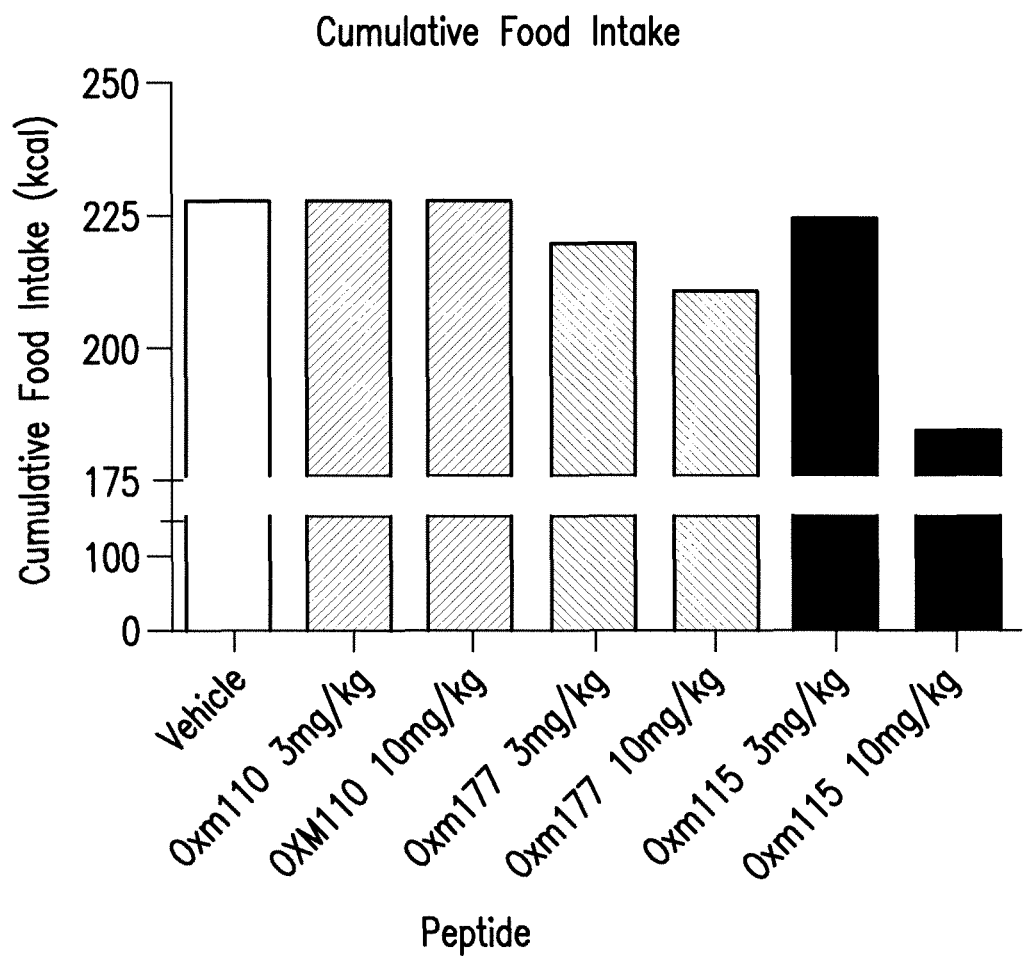
Figure 9C:
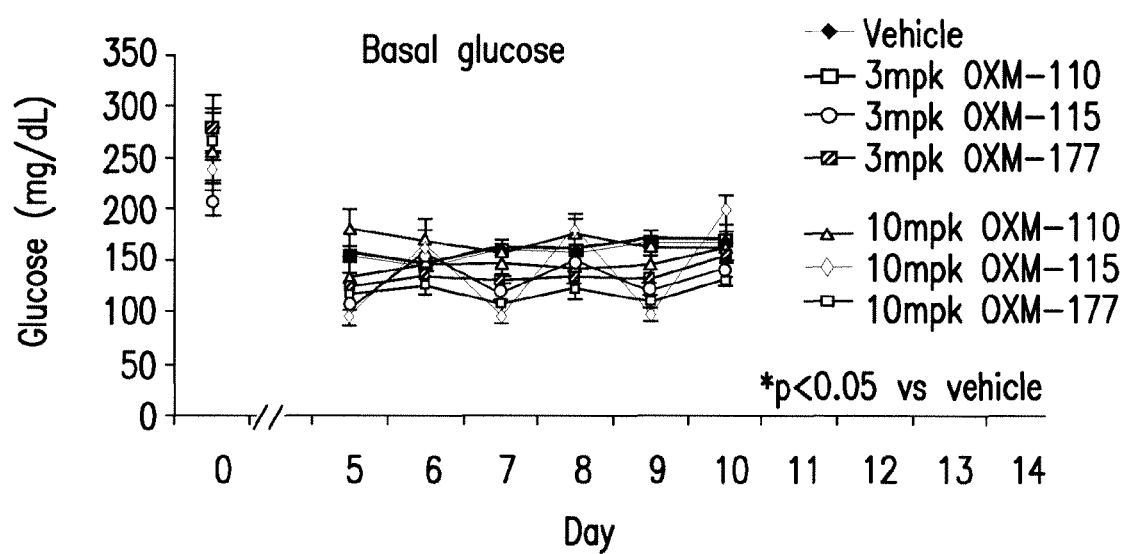

Pharmacodynamic analysis of selected analogs. We evaluated the efficacy of various lipidated peptides to reduce body weight, food intake (DIO mice) and improve glycemic control (lean mice) following both acute and chronic administration. As shown in FIGS. 6 through 9, following a single subcutaneous dose, the lipidated molecules significantly reduce food intake and body weight both acutely and with sustained efficacy. As predicted from the in vitro analysis, day (Q2D) during the course of a 14-consecutive-day study. Body weight, food intake and basal glucose levels were measure daily. As shown in FIGS. 9A and 9B, chronic treatment with the lipidated analogs significantly reduced body weight and food intake in a dose dependent manner throughout the duration of the study. FIG. 9C shows the basal glucose over the time period of the study in response to the various peptides.

Figure 9D:
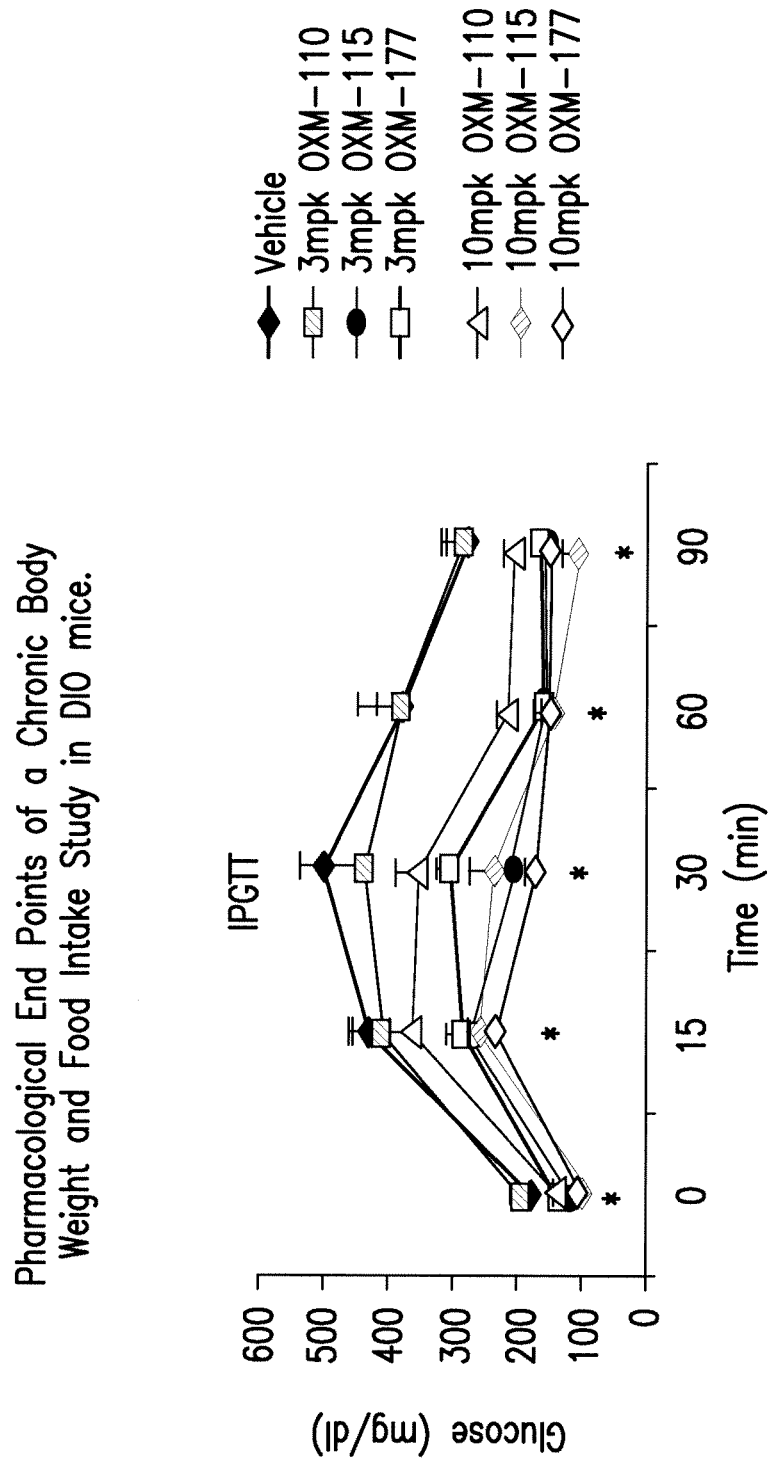
Figure 10:
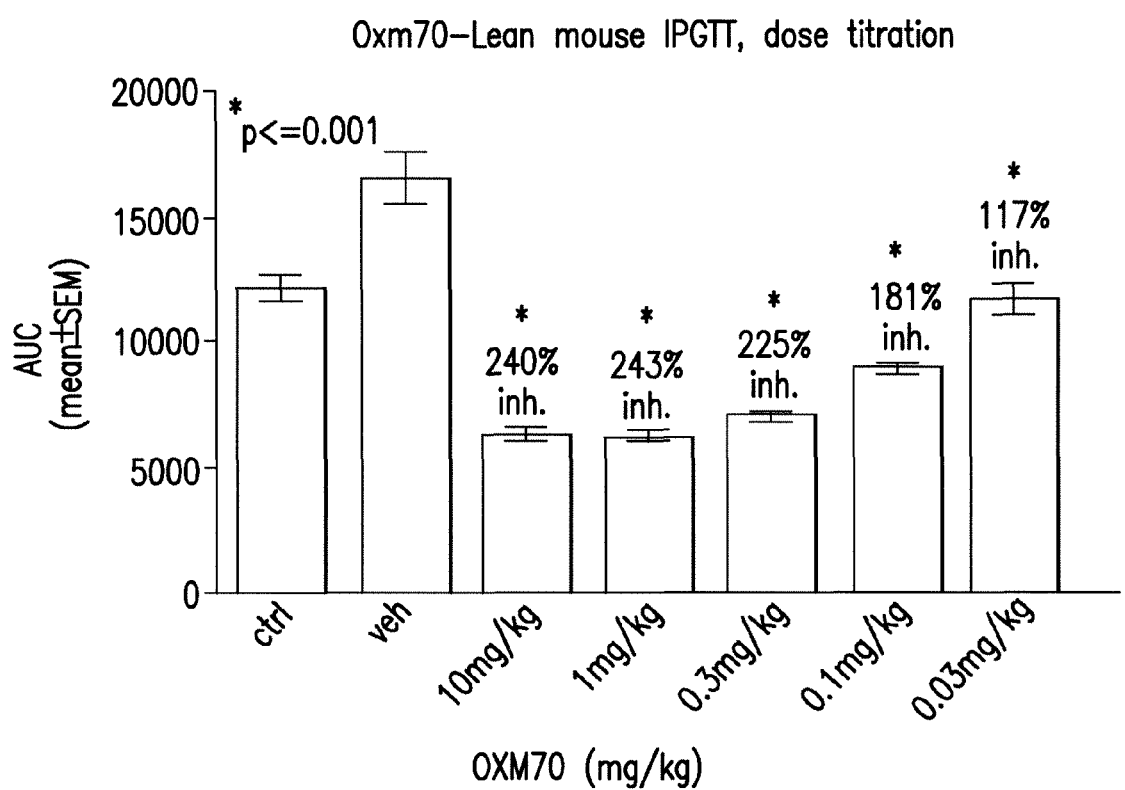
FIG. 10 shows the results of an intraperitoneal glucose tolerance test (IPGTT) in lean mice for subcutaneous administration of OXM70.
Figure 11:
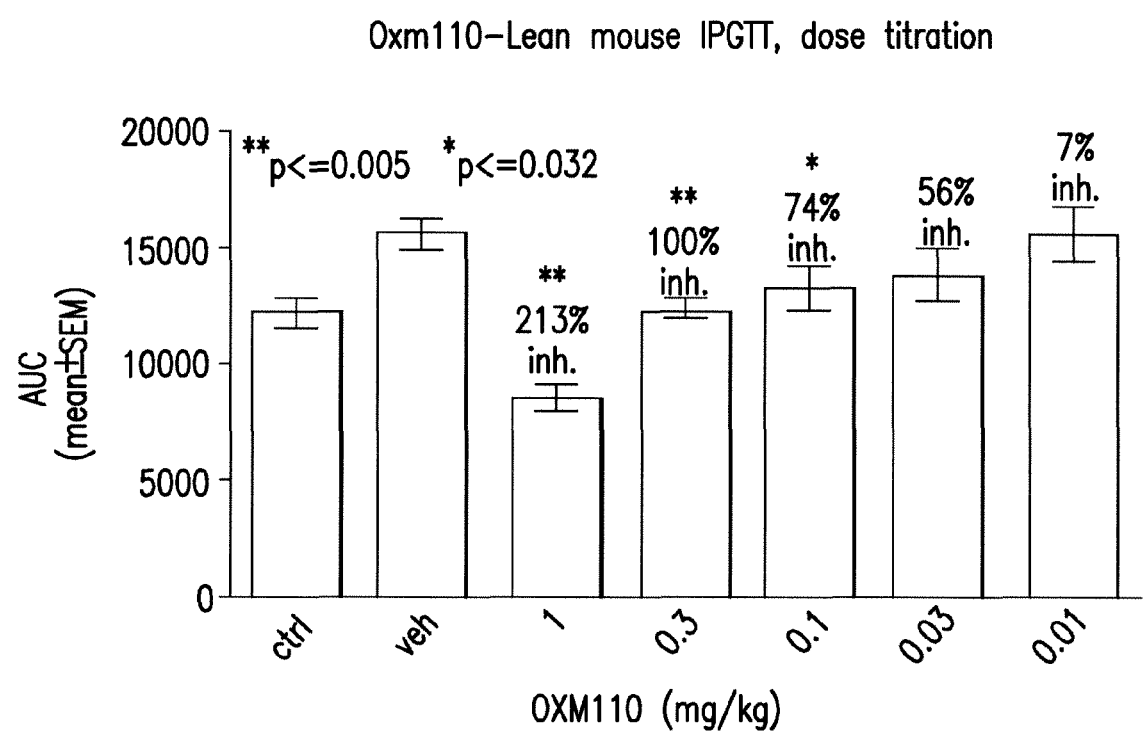
FIG. 11 shows the results of an intraperitoneal glucose tolerance test (IPGTT) in lean mice for subcutaneous administration of OXM110.
Figure 12:
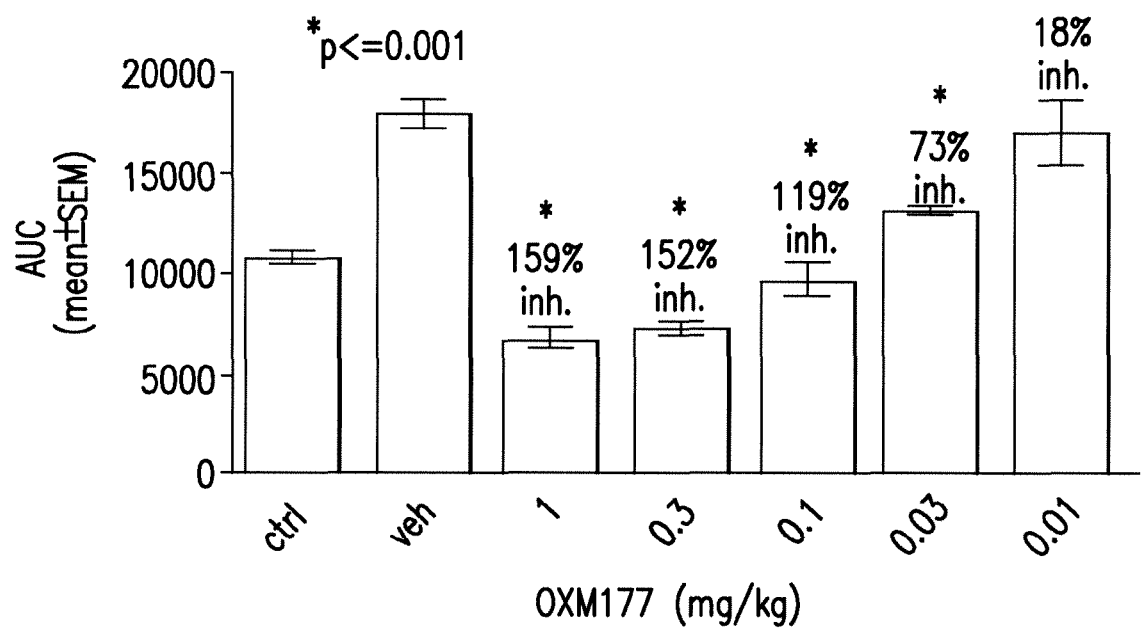
FIG. 12 shows the results of an intraperitoneal glucose tolerance test (IPGTT) in lean mice for subcutaneous administration of OXM177.
Figure 13:
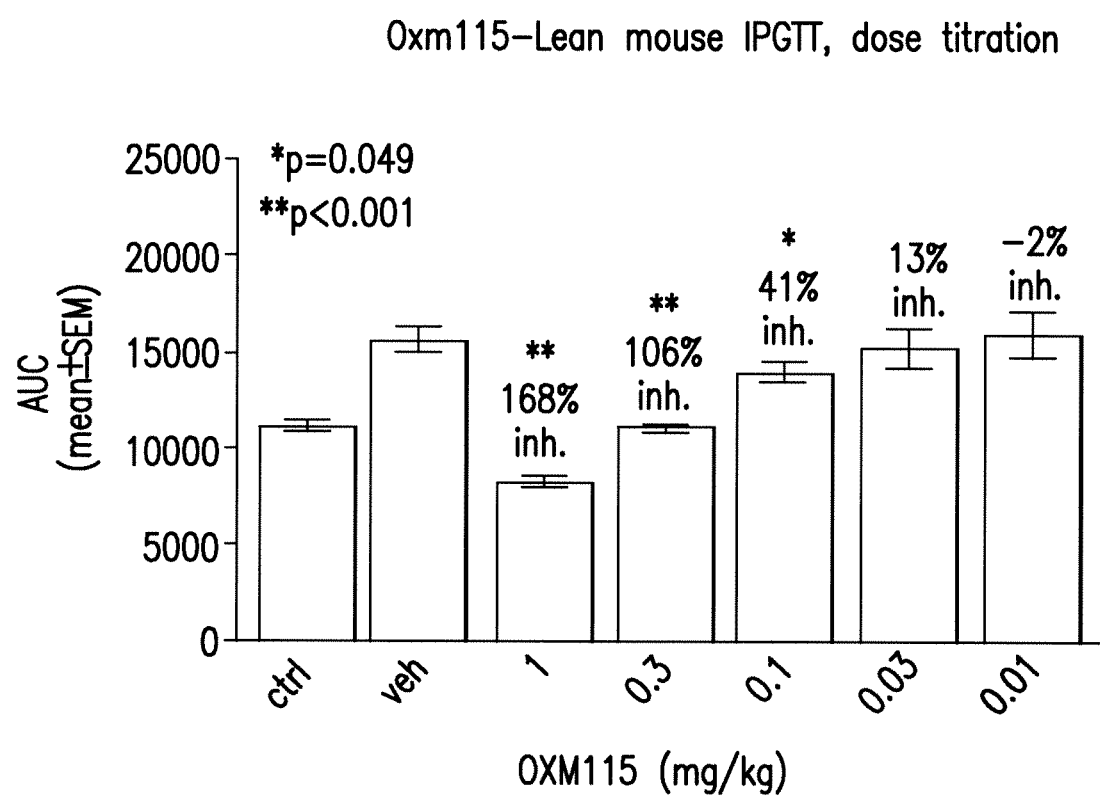
FIG. 13 shows the results of an intraperitoneal glucose tolerance test (IPGTT) in lean mice for subcutaneous administration of OXM115.

All the lipidated peptides tested significantly reduced basal glucose in a dose dependent manner throughout the duration of the study compared with day 0 of the chronic study and with vehicle-treated animals in the same day (p<0.05). An IPGTT was carried out on day 13, showed that glucose tolerance was improved following chronic administration of the lipidated analogs, in a dose dependent manner (FIG. 9D).

Improvement Glucose Tolerance

As shown in FIGS. 10 through 13, in C57BL/6N lean mice IPGTT, the subcutaneous administration of the OXM peptide analogs, prior to dextrose challenge timed appropriately to correspond to the Plasma $C_{max}$, significantly reduced blood glucose excursion in a dose-dependent manner, for all lipidated analogs tested.

Metabolic Rate Effects

Figure 14A:
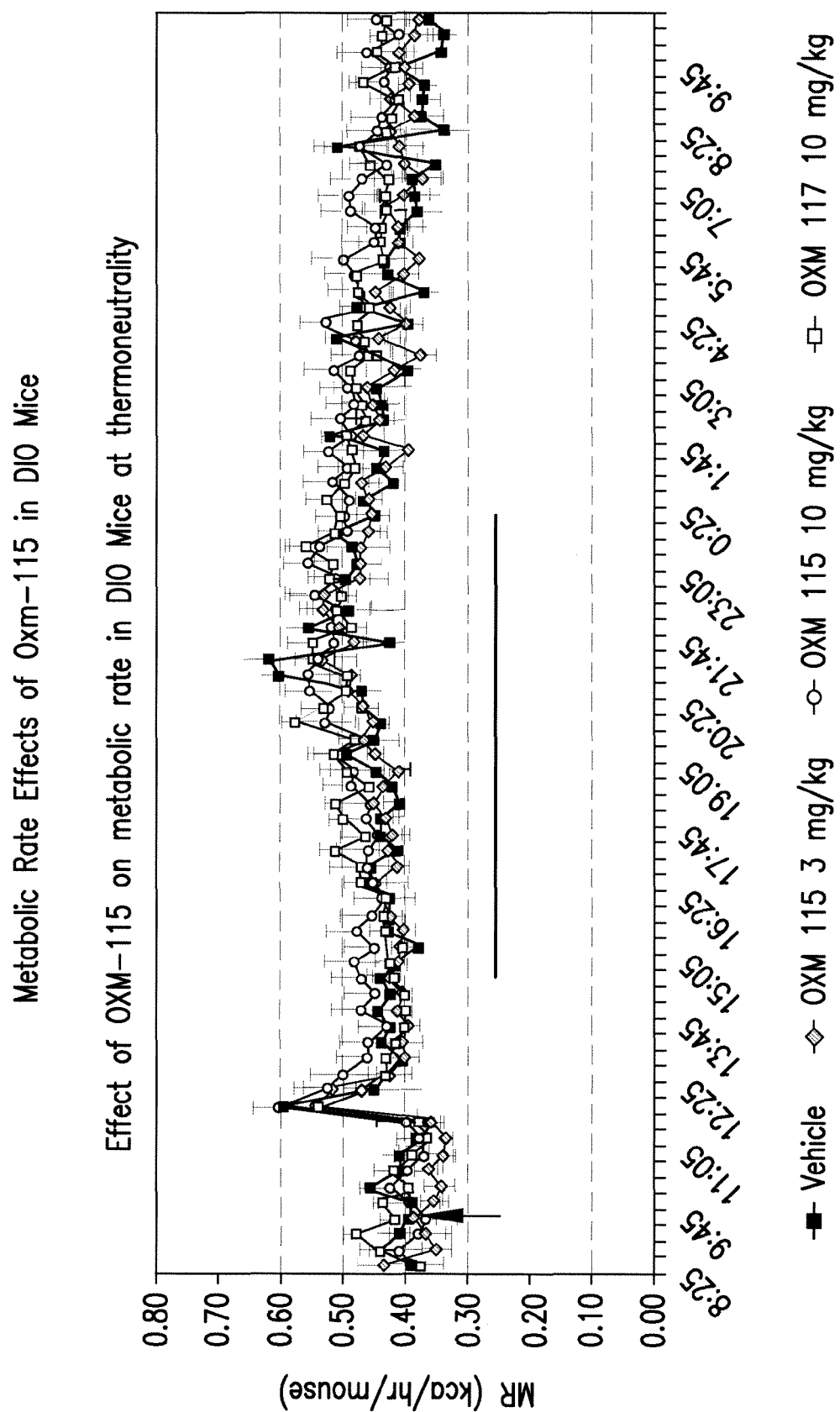
FIG. 14A shows the metabolic rate effects of OXM115 in DIO Mice over time.
Figure 14B:
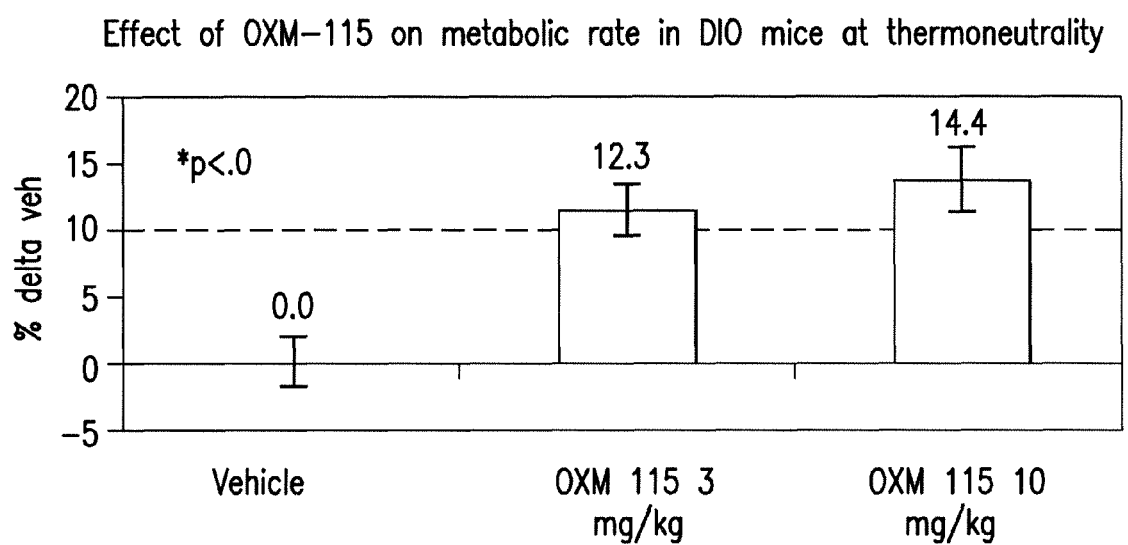
FIG. 14B shows the percent change in metabolic rate caused by OXM115 in the DIO Mice.

In order to establish whether administration of the tetra-ethoxy-linked cholestroylated OXM115 analog confers a metabolic rate, a chronic study was performed, with a single injection of OXM115. Male B6 DIO mice (average starting body weight 55 g) were acclimated to metabolic rate chambers without food at thermoneutrality (T 29° C.). A three hour period from 6:00 to 9:00 am was used to calculate resting metabolic rate. Three hours into the light phase (9:00 am), vehicle (dH$_2$O), OXM115 at 3 or 10 mg/kg was administered subcutaneously. The total cycle time was set for 20 minutes, consisting of a reference reading with a 70 second settling time and a 10 second measure period as well as 60 second settle time and 10 second measure time for each of the 16 cages. Results shown in FIGS. 14A and B show that administration of OXM115 dose dependently increased the acute metabolic rate in DIO mice.

Figure 15:
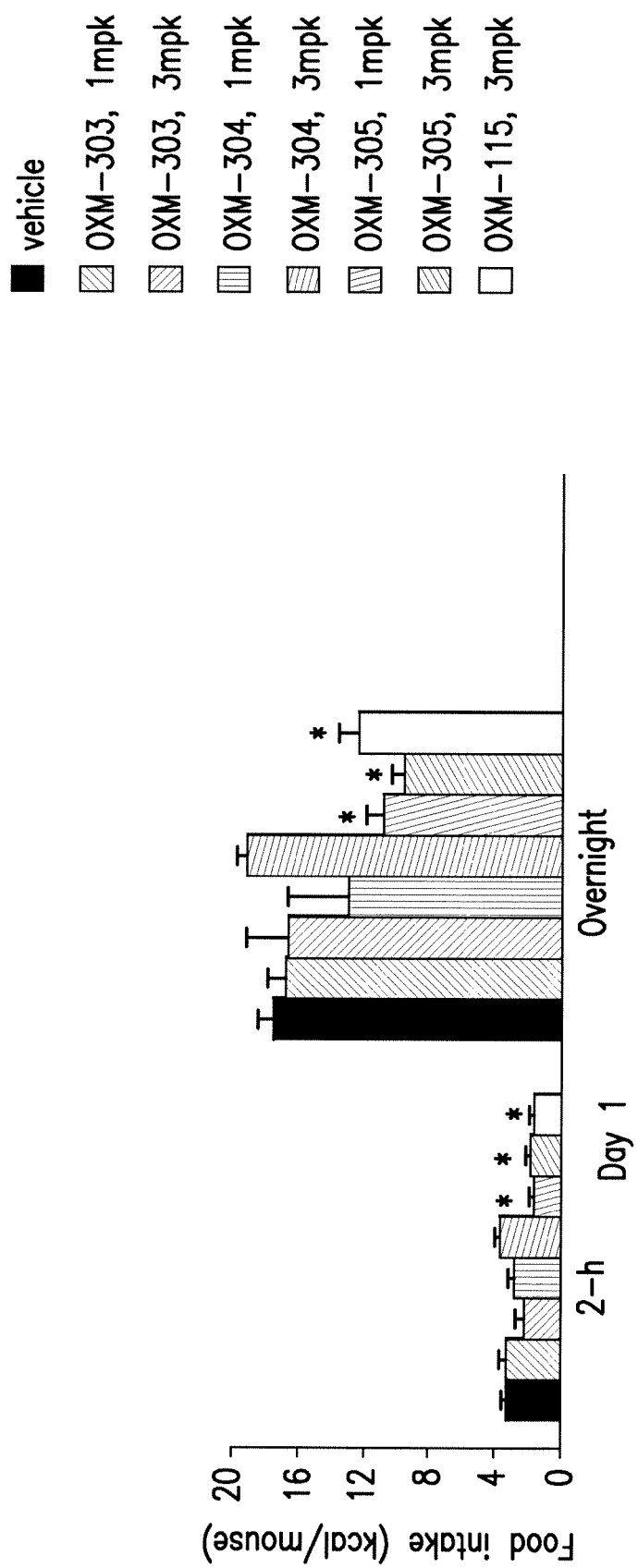
FIG. 15 summarizes the acute in vivo efficacy of several +/+ peptides on reducing food intake and body weight in established DIO mice.

FIG. 15 summarizes the acute in vivo efficacy of OXM303, OXM304, and OXM305 on reducing food intake and body weight in established DIO mice and shows OXM305 as being particularly efficacious at reducing food intake and reducing body weight. Ad libitum fed, DIO male C57BL/6 mice (about 50 g each) were weighed and dosed s.c. with either vehicle (water) or OXM analogs 30 minutes prior to the onset of the dark phase. Food intake was measured two hours, 18, and 42 hours later. Body weight changes at 18 and 42 hours (overnight) were also measured (*P<0.05 vs. vehicle, n=5-6 per group).

Figure 16:
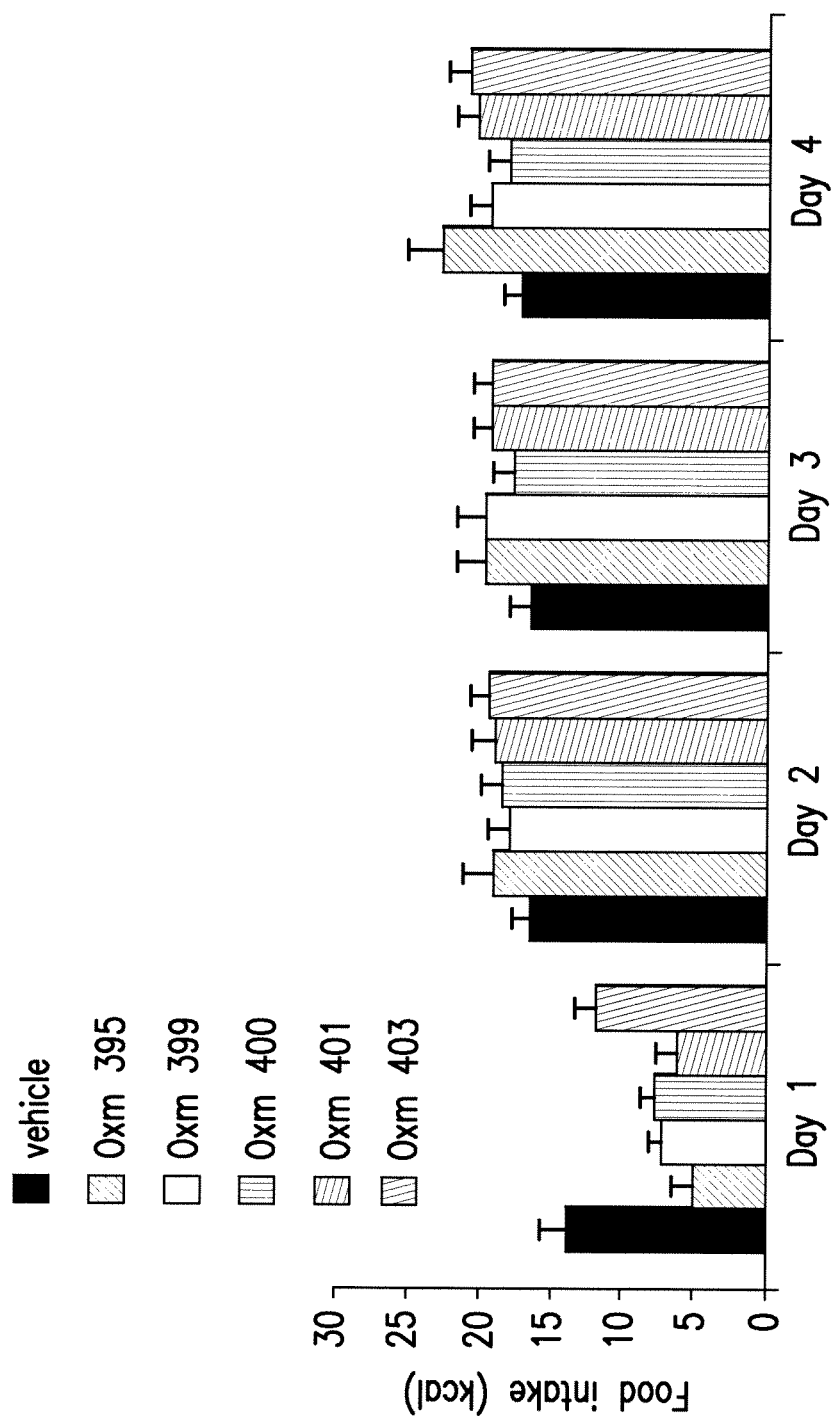
FIG. 16 shows single dose of several +/+ peptides on food intake on reducing food intake and body weight in established DIO mice.

FIG. 16 summarizes the acute in vivo efficacy of OXM395, OXM399, OXM400, and OXM401 on reducing food intake and body weight in established DIO mice. OXM401 is a 0/+ control peptide having the sequence HAibEGTFTSDYSKYLDSRRAQDFVQWLmNTK-γEγE-C(Oxa$_{12}$Chol) (SEQ ID NO:99). Established DIO mice (~52 g each) were dosed sc with vehicle (30% HBC) or peptide 1 mg/kg about 30 minutes prior to the onset of the dark phase. Food intake and body weight changes were measured over a four day time period (*P<0.05 vs. vehicle, n=5 per group).

Example 11

This example shows that lipidated peptides with a pI above 7 based on the OXM sequence stimulate mast cell degranulation while lipidated peptides with a pI of about 5 appears not to stimulate mast degranulation.

To assess the histamine releasing potential of oxyntomodulin analogs, we established an in vitro counterscreening assay using the human mast cell line LAD2. LAD2 cells (50,000 cells/well, 96-well plate) were incubated with compounds for 30 minutes. The degranulation of LAD2 cells was determined by quantification of the β-hexosaminidase released into the supernatants and in cell lysates after hydrolysis of 4-methylumbelliferyl-N-acetyl-β-D-glucosaminide. Results are expressed as percentage of β-hexosaminidase release, calculated as percent of total content. Table 1 summarizes the degranulation potency (EC$_{50}$) of OXM analogues in LAD2 cells. The results suggest that to reduce the likelihood of stimulating degranulation of mast cells, the pI for lipidated based analogues should be around 5.

TABLE 9

Degranulation potency of native OXM and OXM analogues

| Peptide | EC$_{50}$ (μM) |
| --- | --- |
| OXM | >10 |
| OXM115 | 0.01-0.04 |
| OXM238 | 1.5 |
| OXM303 | 0.1 |
| OXM305 | 0.1 |
| OXM392 | 0.3 |
| OXM399 | 0.3 |
| OXM400 | >10 |
| OXM401 | >10 |
| OXM404 | >10 |
| OXM408 | >10 |
| OXM409 | >10 |
| OXM410 | >10 |
| OXM411 | >10 |

Example 12

This example presents tables showing the in vitro potencies of various peptide analogs at the human GLP-1 receptor (hGLP-1R) and the human glucagon receptor (hGCGR). The in vitro potencies shown in Table 10 or Table 11 were determined from the results of assays that were similar to either the cell-based cAMP assays described herein above (Table 10) or the cell-based cAMP assays described in International Published Application No. WO2008101017, which is incorporated herein in its entirety, in particular the cell-based cAMP assays described therein (Table 11).

TABLE 10

In vitro potencies of selected peptide analogs

| Peptide | pI | hGLP-1R EC50 (nM) | hGLP-1R + 20% Plasma EC50 (nM) | hGCGR EC50 (nM) | hGCGR + 20% plasma EC50 (nM) |
| --- | --- | --- | --- | --- | --- |
| OXM345 | 5.4 | 5.1 | >1000 | 0.1 | >1000 |
| OXM380 | 5.4 | 0.3 | 30.7 | 0.1 | 3.4 |
| OXM381 | 5.2 | 0.002; 0.02 | 1.9; 1.9 | 0.0002; 0.006 | 0.8; 0.9 |
| OXM389 | — | 0.03 | — | 0.02 | — |
| OXM392 | 5.4 | 0.03 | 3.0 | 0.03 | 0.3 |
| OXM395 | 5.4 | 0.7 | 3.3 | 10 | 119 |
| OXM399 | 5.4 | 0.05 | 5.7 | 0.01 | 0.4 |
| OXM400 | 5.4 | 0.07 | 1.9 | 0.01 | 0.8 |
| OXM401 | 5.4 | 0.23 | 2.9 | 0.09 | 0.3 |
| OXM409 | 5.5 | — | 0.7 | — | 0.1 |
| OXM411 | 5.4 | — | 0.1 | — | 0.2 |
| OXM414 | 5.4 | — | 0.07 | — | 0.15 |
| OXM416 | 5.5 | — | 0.09 | — | 1.40 |
| OXM417 | 5.5 | — | 0.15 | — | 0.40 |
| OXM418 | 5.5 | — | 0.30 | — | 0.30 |

TABLE 11

In vitro potencies of selected peptide analogs

| Peptide | hGLP-1R EC50 (nM) | hGCGR EC50 (nM) |
|---|---|---|
| MM111 | 0.007 | 0.005 |
| MM102 | 0.034 | 0.003 |
| MM103 | 0.026 | 0.005 |
| MM113 | 0.023 | 0.006 |
| OXM414 | 0.007 | 0.005 |
| MM114 | 0.036 | 0.019 |
| MM115 | 1.083 | 1.313 |
| MM116 | 0.132 | 0.85 |
| MM117 | 0.93 | 0.25 |
| MM121 | 0.131 | 0.006 |
| MM132 | 0.024 | 0.004 |
| OXM418 | 0.026 | 0.002 |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A peptide analog comprising:

Z1-P-M-Z2 wherein P is a peptide having the amino acid sequence (SEQ ID NO: 110)
HX1QGTFTSDX2SX3YLDX4X5X6AX7DFVQWLX8NTKX9X10 wherein X1 is a D-serine, α-aminoisobutyric acid (aib), 1-Amino-1-cyclobutane carboxylic acid (Acb) residue, 1-Amino-1-cyclohexane carboxylic acid (Acx); alpha-aminobutyric acid (Abu); D-alpha-aminobutyric acid (D-Abu); Aminovaleric acid (Nva); beta-cyclopropyl-alanine (Cpa); propargylglycine (Prg); Allylglycine (Alg); 2-Amino-2-cyclohexyl-propanoic acid (2-Cha); D-tertbutylglycine (D-tbg); Vinylglycine (Vg); 1-Amino-1-cyclopropane carboxylic acid (Acp); or 1-Amino-1-cyclopentane carboxylic acid (Acpe) residue;

X2 is a tyrosine (Y) or lysine (K) residue;

X3 is serine (S) or lysine (K) residue;

X4 is serine (S), α-aminoisobutyric acid (aib), or glutamic acid (E) residue;

X5 is an arginine (R) or glutamic acid (E) residue;

X6 is an arginine (R) or alanine (A) residue;

X7 is a glutamine (Q) or lysine (K) residue;

X8 is a methionine (M), norleucine (Nle), methionine sulfoxide (m), or O-methyl-L-homoserine (o) residue;

X9 is a gamma glutamic acid (γGlu) residue;

X10 is a gamma glutamic acid (γGlu) residue or absent;

Z1 is an optionally present protecting group that, if present, is joined to the N-terminal amino group, M is (i) a cysteine residue covalently linked to a cholesterol moiety by a hydrophilic linker, (ii) a lysine residue covalently linked to a lipid moiety by a spacer comprising one or more gamma glutamic acid residues, or (iii) a lipid moiety, wherein M is covalently linked to a C-terminal or internal amino acid of P by a spacer comprising one or more gamma-glutamic acid residues; and Z2 is an optionally present protecting group that, if present, is joined to the C-terminal carboxy group; and pharmaceutically acceptable salts thereof, wherein the peptide analog or salt thereof has a pI of less than 6.0 and is a dual GLP-1 receptor agonist and glucagon receptor agonist.

2. The peptide analog of claim 1, wherein M is a cysteine residue covalently linked to a cholesterol moiety with a hydrophilic linker and the cysteine residue is linked to the C-terminus of P.

3. The peptide analog of claim 1, wherein M is a lysine residue covalently linked to a lipid moiety by a spacer comprising one or more gamma glutamic acid residues and the lysine residue is linked to the C-terminus of P.

4. The peptide analog of claim 1, wherein M is a lysine residue covalently linked to a lipid moiety by a spacer comprising one or more gamma glutamic acid residues and the lysine residue is at position X2 or X7 of P.

5. The peptide analog of claim 1, wherein the hydrophilic linker is an ethoxy polymer that includes one to twenty-four ethoxy units.

6. The peptide analog of claim 1, wherein the hydrophilic linker is an ethoxy polymer that includes four ethoxy units.

7. The peptide analog of claim 1, wherein the lipid moiety is a palmitoyl moiety.

8. The peptide analog of claim 1, wherein the peptide analog is OXM319 (SEQ ID NO:62); OXM327 (SEQ ID NO:66); OXM329 (SEQ ID NO:67); OXM383 (SEQ ID NO:78); or OXM388 (SEQ ID NO:79).

9. The peptide analog of claim 1 wherein M is a lysine residue covalently linked to a lipid moiety by a spacer comprising one or more gamma glutamic acid residues and the lysine residue is linked to the C-terminus of P or M is a lysine residue covalently linked to a lipid moiety by a spacer comprising one or more gamma glutamic acid residues and the lysine residue is at position X2 or X7 of P.

10. The peptide analog of claim 9, wherein the lipid moiety is a palmitoyl, myristoyl, or stearoyl moiety.

* * * * *